US011565999B2

(12) United States Patent
Gordon et al.

(10) Patent No.: US 11,565,999 B2
(45) Date of Patent: Jan. 31, 2023

(54) METHODS OF SYNTHESIZING AZTREONAM DERIVATIVES

(71) Applicant: ARIXA PHARMACEUTICALS, INC., Palo Alto, CA (US)

(72) Inventors: Eric M. Gordon, Palo Alto, CA (US); Matthew A. J. Duncton, Palo Alto, CA (US); John Freund, Palo Alto, CA (US)

(73) Assignee: Arixa Pharmaceuticals, Inc., New York, NY (US)

( * ) Notice: Subject to any disclaimer, the term of this patent is extended or adjusted under 35 U.S.C. 154(b) by 0 days.

(21) Appl. No.: 16/840,675

(22) Filed: Apr. 6, 2020

(65) Prior Publication Data

US 2020/0339507 A1 Oct. 29, 2020

Related U.S. Application Data

(60) Provisional application No. 62/838,880, filed on Apr. 25, 2019.

(51) Int. Cl.
*C07D 417/12* (2006.01)
*C07D 205/095* (2006.01)
*C07D 471/08* (2006.01)
*A61K 45/06* (2006.01)

(52) U.S. Cl.
CPC ....... *C07D 205/095* (2013.01); *C07D 417/12* (2013.01); *C07D 471/08* (2013.01); *A61K 45/06* (2013.01)

(58) Field of Classification Search
CPC .................................................. C07D 417/12
See application file for complete search history.

(56) References Cited

U.S. PATENT DOCUMENTS

| | | | |
|---|---|---|---|
| 3,658,849 | A | 4/1972 | Leffingwell |
| 4,522,811 | A | 6/1985 | Eppstein et al. |
| 4,652,651 | A | 3/1987 | Furlenmeier et al. |
| 4,775,670 | A | 10/1988 | Sykes et al. |
| 5,674,533 | A | 10/1997 | Santus et al. |
| 7,112,592 | B2 | 9/2006 | Lampilas et al. |
| 7,994,218 | B2 | 8/2011 | Jandeleit et al. |
| 8,168,617 | B2 | 5/2012 | Jandeleit et al. |
| 8,772,490 | B2 | 7/2014 | Abe et al. |
| 9,035,062 | B2 | 5/2015 | Abe et al. |
| 9,284,273 | B2 | 3/2016 | Abe et al. |
| 9,340,493 | B2 | 5/2016 | Brown et al. |
| 9,393,239 | B2 | 7/2016 | Maiti et al. |
| 10,280,161 | B2 | 5/2019 | Gordon et al. |
| 2009/0099253 | A1 | 4/2009 | Li et al. |
| 2014/0045943 | A1 | 2/2014 | Khan et al. |
| 2015/0196559 | A1 | 7/2015 | Wang et al. |
| 2015/0225335 | A1 | 8/2015 | Takashima et al. |
| 2017/0165371 | A1 | 6/2017 | Goldberg |
| 2017/0290918 | A1 | 10/2017 | Honda et al. |
| 2017/0296503 | A1 | 10/2017 | Eto et al. |
| 2018/0148448 | A1 | 5/2018 | Wu |

FOREIGN PATENT DOCUMENTS

| | | | |
|---|---|---|---|
| DE | 3045373 | 7/1982 | |
| KR | 10-0472048 B1 * | 3/2005 | ........... C07D 417/12 |
| WO | 2007/116922 | 10/2007 | |
| WO | 2009/033054 | 3/2009 | |
| WO | 2009/033061 | 3/2009 | |
| WO | 2009/033069 | 3/2009 | |
| WO | 2009/033079 | 3/2009 | |
| WO | 2009/092606 | 7/2009 | |
| WO | 2011/046771 | 4/2011 | |
| WO | 2011/150380 | 12/2011 | |
| WO | 2012/086241 | 6/2012 | |
| WO | 2012/165648 | 12/2012 | |
| WO | 2016/116788 | 7/2016 | |
| WO | 2017/045510 | 3/2017 | |
| WO | 2019/070595 | 4/2019 | |

OTHER PUBLICATIONS

A machine generated English translation of KR 10-0472048 B1 (Yeong), 2005. (Year: 2005).*
Examiners report for Australian Application No. 2018 345321, dated Jun. 2, 2020, 3 pages.
International Search Report and Written Opinion for Application No. PCT/US2020/026821, dated Jul. 20, 2020, 22 pages.
Beutner et al., "TCFH-NMI: Direct Access to N-Acyl Imidazoliums for Challenging Amide Bond Formations", Organic Letters, Jul. 2018, vol. 20, No. 14, p. 4218-4222.
Carpino et al., "Tetramethylfluoroformamidinium Hexafluorophosphate: A Rapid-Acting Peptide Coupling Reagent for Solution and Solid Phase Peptide Synthesis", Journal of American Chemical Society, 1995, vol. 117, p. 5401-5402.
International Search Report and Written Opinion for Application No. PCT/US2018/053778, dated Nov. 26, 2018, 11 pages.
International Search Report and Written Opinion for Application No. PCT/US2018/030652, dated Aug. 29, 2018, 13 pages.
Non-Final Office Action for U.S. Appl. No. 16/351,300, dated Mar. 24, 2020, 7 pages.
Beaudoin et al., "Bioanalytical method validation for the simultaneous determination of ceftazidime and avibactam in rat plasma," Bioanalysis, 2016, vol. 8, No. 2, p. 111-122.
Beaudoin et al., "Preparation of Unsymmetrical Sulfonyureas from N,N-Sulfuryldiimidazoles," the Journal of Organic Chemistry, 2003, vol. 68, No. 1, p. 115-119.
Boyd et al., "NMR spectroscopic studies of intermediary metabolites of cyclophosphamide. 2. Direct observation, characterization, and reactivity studies of iminocyclophosphamide and related species," The Journal of Medicinal Chemistry, 1987, vol. 30, No. 2, p. 366-374.
DeBergh et al., "Synthesis of Aryl Sulfonamides via Palladium-Catalyzed Chlorosulfonylation of Arylboronic Acids," Journal of the American Chemical Society, 2013, vol. 135, No. 29, p. 10638-10641.

(Continued)

*Primary Examiner* — Laura L Stockton
(74) *Attorney, Agent, or Firm* — Jason Tebbutt

(57) ABSTRACT

Disclosed herein are aztreonam derivatives, therapeutic methods of using the aztreonam derivatives, and methods of synthesizing aztreonam derivatives. The aztreonam derivatives can be administered orally to provide orally bioavailable aztreonam.

6 Claims, 5 Drawing Sheets

(56) References Cited

OTHER PUBLICATIONS

Hecker et al., "Discovery of a Cyclic Boronic Acid β-Lactamase Inhibitor (RPX7009) with Utility vs Class A Serine Carbapenemases," Journal of Medicinal Chemistry, 2015, vol. 58, p. 3682-3692.

Hutchinson et al., "Inhaled Aztreonam Lysine: An Evidence-Based Review", Expert Opinion on Pharmacotherapy, vol. 14, No. 15, Aug. 31, 2013, pp. 2115-2124, XP055524539, 11 p.

Illa et al., "Practical and Highly Selective Sulfur Ylide-Mediated Asymmetric Expoxidations and Aziridinations Using a Cheap and Readily Available Chiral Sulfide: Extensive Studies to Map Out Scope, Limitations, and Rationalization of Diastereo- and Enantioselectivities," Journal of the American Chemical Society, 2013, vol. 135, No. 32, p. 11951-11966.

King et al., "Structural and Kinetic Characterization of Diazabicyclooctanes as Dual Inhibitors of Both Seratin-B-Lactamase and Penicillin-Binding Proteins," ACS Chemical Biology, 2016, vol. 11, No. 4, p. 864-868.

Klinger-Strobel, Mareike, et al., "Aspects of Pulmonary Drug Delivery Strategies for Infections in Cystic Fibrosis—Where Do We Stand?", Expert Opinion on Drug Delivery, vol. 12, No. 8, Feb. 2, 2015, pp. 1351-1374, XP055524515, 25 pages.

Oger et al., "Lipase-Catalyzed Regioselective Monoacetylation of Unsymmetrical 1,5-Primary Diols," The Journal of Organic Chemistry, 2010, vol. 75, No. 6, p. 1892-1897.

Levasseur et al., "In vitro antibacterial activity of the ceftazidime-avibactam combination against enterobacteriaceae, including strains with well-characterized β-lactamases," Antimicrobial Agents Chemotherapy, 2015, vol. 59, No. 4, p. 1931-1634.

Livermore et al., "Activity of OP0595/β-lactam combinations against Gram-negative bacteria with extended-spectrum, AmpC and carapenem—hydrolysing β-lactamases," Journal of Antimicrobial Chemotherapy, 2015, vol. 70, Issue 11, p. 3032-3041.

Rusha et al., "Design and application of esterase-labile sulfonate protecting groups," Chemical Communications, 2011, vol. 47, p. 2038-2040.

Shi et al., "The Rhodium-Catalyzed Carbene Cyclization Cycload-dition Cascade Reaction of Vinylsulfonates," Advanced Synthesis and Catalysis, 2009, vol. 351, p. 3128-3132.

Simpson et al., "A Comprehensive Approach to the Synthesis of Sulfate Esters," Journal of the American Chemical Society, 2006, vol. 128, No. 5, p. 1605-1610.

Soengas et al., "Convenient Procedure for the Indium-Mediated Hydroxymethylation of Active Bromo Compounds: Transformation of Ketones into a-Hydroxymethyl Nitroalkanes," Synlett, 2010, vol. 17, p. 2625-2627.

Zasowski et al., "The β-Lactams Strike Back: Ceftazidime-Avibactam," Pharmacotherapy, 2015, vol. 35, Issue 8, p. 755-770.

Zhang et al., "Enhanced Photoresponsive Ultrathin Graphitic-Phase C3N4 Nanosheets for Bioimaging," Journal of the American Chemical Society, 2013, vol. 135, No. 1, p. 18-21.

* cited by examiner

METHODS OF SYNTHESIZING AZTREONAM DERIVATIVES

This application claims the benefit under 35 U.S.C. § 119(e) of U.S. Provisional Application No. 62/838,880 filed on Apr. 25, 2019, which is incorporated by reference in its entirety.

FIELD

The present disclosure relates to aztreonam derivatives and pharmaceutical compositions thereof, methods of synthesizing aztreonam derivatives, and the use of the aztreonam derivatives to treat bacterial infections. The aztreonam derivatives can be administered orally to provide orally bioavailable aztreonam.

BACKGROUND

Aztreonam is a monobactam antibiotic used primarily to treat gram negative bacteria. Aztreonam has poor oral bioavailability and therefore is administered intravenously, intramuscularly or by inhalation.

SUMMARY

According to the present invention, method of synthesizing an organyl 3-amino-2-methyl-4-oxoazetidine-1-sulfonate having the structure of Formula (5):

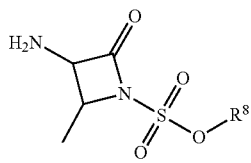

(5)

or a salt thereof, wherein,
R$^8$ is selected from $C_{1-20}$ alkyl, $C_{1-20}$ alkanecycloalkyl, $C_{1-2}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl;
comprise the steps of:
(e) reacting 3-amino-2-tert-butoxycarbonylamino-butyric acid benzyl ester with an organyl sulfurochloridate having the structure of Formula (6):

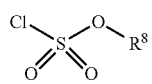

(6)

to provide the corresponding tert-butyl (2S,3S)-2-(((benzyloxy)carbonyl)amino)-3-(((3-organyloxy)sulfonyl)amino)butanoate; and
(f) after removing the benzyl ester, cyclizing the resulting (1-(tert-butoxy)-3-((organyloxysulfonyl)amino)-1-oxobutan-2-yl)carbamic acid in the presence of a cyclization agent to provide the corresponding organyl 3-((tert-butoxycarbonyl)amino)-2-methyl-4-oxoazetidine-1-sulfonate having the structure of Formula (5).

According to the present invention, a compound, organyl 3-amino-2-methyl-4-oxoazetidine-1-sulfonate, having the structure of Formula (5) or a salt thereof is prepared by methods according to the present invention:

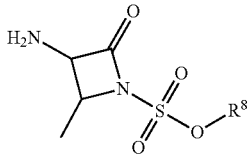

(5)

wherein R$^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl.

According to the present invention, methods of synthesizing an organyl 3-amino-2-methyl-4-oxoazetidine-1-sulfonate having the structure of Formula (5):

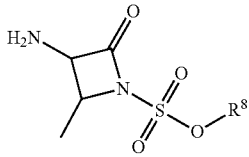

(5)

or a salt thereof, wherein,
R$^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; comprise the steps of:
(e) reacting tert-butyl (2S,3R)-3-amino-2-(((benzyloxy)carbonyl)-amino)butanoate with an organyl sulfurochloridate of Formula (6):

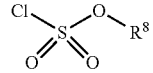

(6)

to provide the corresponding tert-butyl (2S,3S)-2-(((benzyloxy)carbonyl)amino)-3-(((3-organyloxy) sulfonyl)amino)butanoate; and
(f) following removal of the benzyl ester, cyclizing the resulting 2-tert-butoxycarbonylamino-3-(2-organyloxysulfonyl-amino)-butyric acid in the presence of a cyclization agent to provide the corresponding organyl 3-((tert-butoxycarbonyl)amino)-2-methyl-4-oxoazetidine-1-sulfonate having the structure of Formula (5).

According to the present invention, a compound, organyl 3-amino-2-methyl-4-oxoazetidine-1-sulfonate, is synthesized by methods according to the present invention, wherein the compound has the structure of Formula (5):

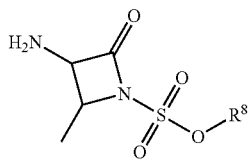

(5)

or a salt thereof, wherein, $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl.

According to the present invention, methods of synthesizing 2-[(2-amino-thiazol-4-yl)-carboxy-methyleneaminooxy]-2-methyl-propionic acid ester, comprise the steps of:

(a) reacting 2-[(2-amino-thiazol-4-yl)-carboxy-methyleneaminooxy]-2-methyl-propionic acid tert-butyl ester and (9H-fluoren-9-yl)-methanol in the presence of a carboxyl activating agent to provide 2-[(2-amino-thiazol-4-yl)-(9H-fluoren-9-ylmethoxycarbonyl)-methyleneaminooxy]-2-methyl-propionic acid tert-butyl ester;

(b) treating the 2-[(2-amino-thiazol-4-yl)-(9H-fluoren-9-ylmethoxycarbonyl)-methyleneaminooxy]-2-methyl-propionic acid tert-butyl ester with an acid to provide the corresponding salt;

(c) reacting the salt with an alcohol in the presence of a carboxyl activating agent to provide the corresponding 2-[(2-amino-thiazol-4-yl)-(9H-fluoren-9-ylmethoxycarbonyl)-methyleneaminooxy]-2-methyl-propionic acid ester; and (d) removing the (9H-fluoren-9-yl)-methyl group by treating the 2-[(2-amino-thiazol-4-yl)-(9H-fluoren-9-ylmethoxycarbonyl)-methyleneaminooxy]-2-methyl-propionic acid ester with pyridine to provide the corresponding 2-[(2-amino-thiazol-4-yl)-carboxy-methyleneaminooxy]-2-methyl-propionic acid ester, wherein the 2-[(2-amino-thiazol-4-yl)-carboxy-methyleneaminooxy]-2-methyl-propionic acid ester has the structure of Formula (7):

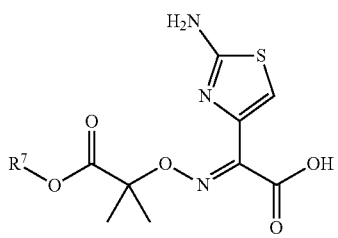

(7)

wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

According to the present invention, a compound, 2-[(2-amino-thiazol-4-yl)-carboxy-methyleneaminooxy]-2-methyl-propionic acid ester, or a salt thereof, is synthesized using methods according to the present invention, wherein the compound has the structure of Formula (7):

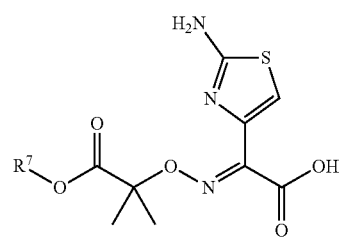

(7)

wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

According to the present invention, methods of synthesizing an aztreonam derivative of Formula (1a):

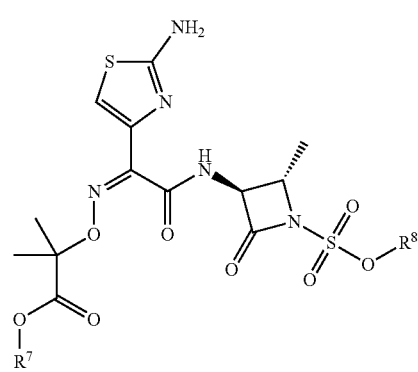

(1a)

or a pharmaceutically acceptable salt thereof, wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl;

comprise (a) reacting an organyl 3-amino-2-methyl-4-oxoazetidine-1-sulfonate salt with a 2-[(2-amino-thiazol-4-yl)-carboxy-methyleneaminooxy]-2-methyl-propionic acid ester in the presence of a carboxyl activating agent to provide the corresponding aztreonam sulfonyloxy organyl ester salt having the structure of Formula (1a), wherein, the organyl 3-amino-2-methyl-4-oxoazetidine-1-sulfonate salt has the structure of Formula (5a):

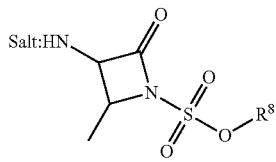

(5a)

wherein, $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; and the 2-[(2-amino-thiazol-4-yl)-carboxy-methyleneaminooxy]-2-methyl-propionic acid ester has the structure of Formula (7):

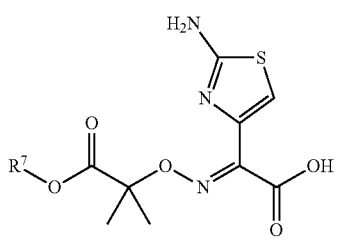

(7)

wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{5-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

According to the present invention, methods of synthesizing an aztreonam derivative of Formula (1a), comprise:

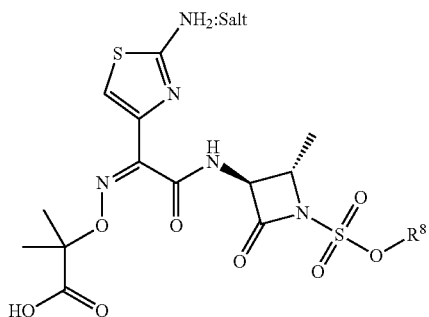

(1a)

or a pharmaceutically acceptable salt thereof, wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl, comprising the steps of; and $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; and (a) reacting an organyl 3-amino-2-methyl-4-oxoazetidine-1-sulfonate salt with a 2-[(2-amino-thiazol-4-yl)-carboxymethyleneaminooxy]-2-methyl-propionic acid tert-butyl ester in the presence of a carboxyl coupling agent to provide the corresponding tert-butoxy protected salt; and (b) treating the tert-butoxy protected salt with an acid to provide the corresponding aztreonam sulfonyloxy organyl ester salt, wherein, the organyl 3-amino-2-methyl-4-oxoazetidine-1-sulfonate salt has the structure of Formula (5a):

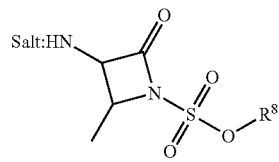

(5a)

wherein, $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; and the 2-[(2-amino-thiazol-4-yl)-carboxy-methyleneaminooxy]-2-methyl-propionic acid tert-butyl ester (7a) has the structure of Formula (7a):

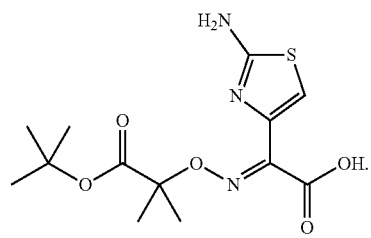

(7a)

According to the present invention, aztreonam derivatives are synthesized using the methods according to the present invention.

Reference is now made to certain compounds and methods. The disclosed embodiments are not intended to be limiting of the claims. To the contrary, the claims are intended to cover all alternatives, modifications, and equivalents.

BRIEF DESCRIPTION OF THE DRAWINGS

Those skilled in the art will understand that the drawings described herein are for illustration purposes only. The drawings are not intended to limit the scope of the present disclosure.

DETAILED DESCRIPTION

Figure 1:
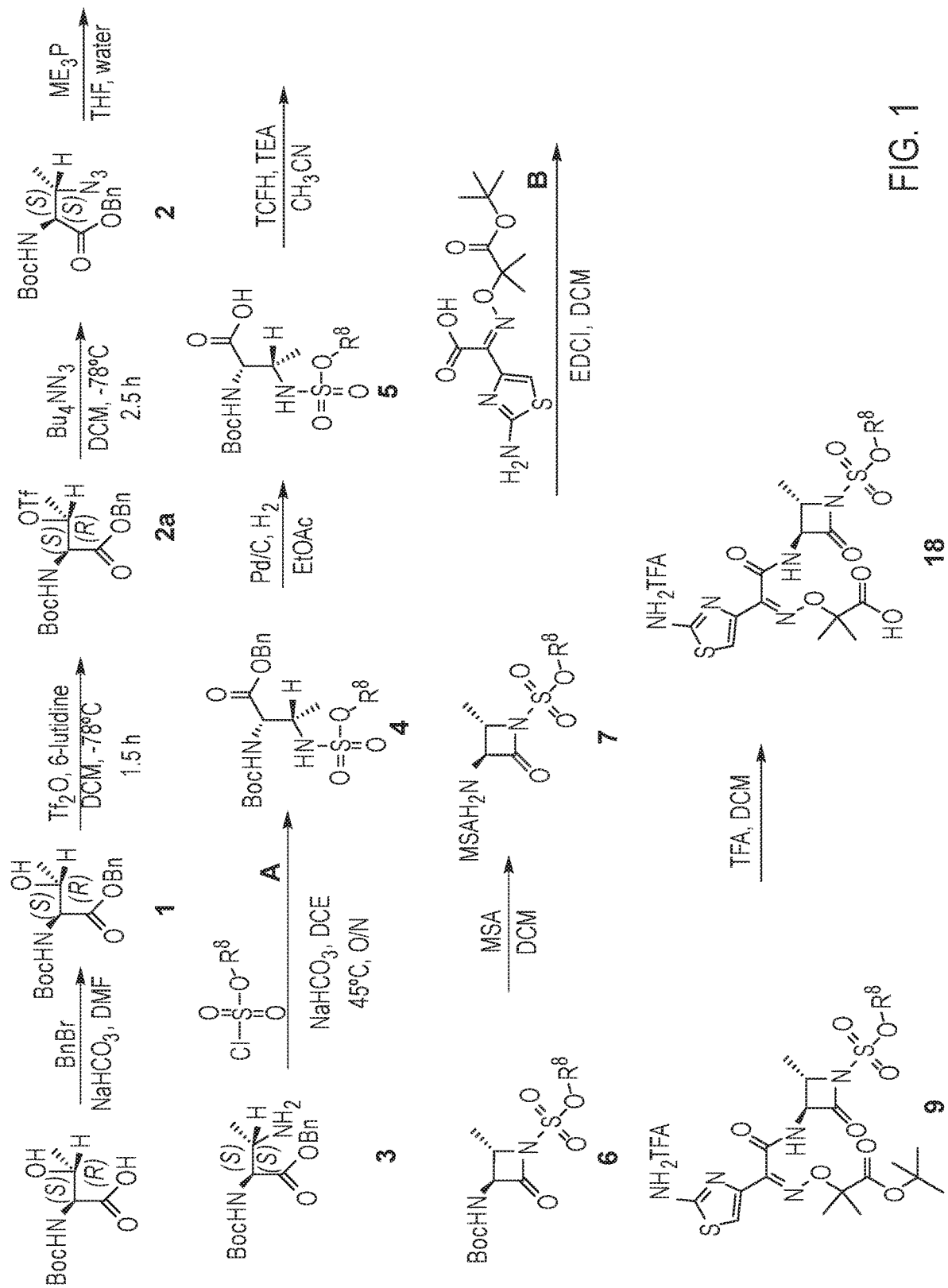
FIG. 1 shows certain steps in synthesizing aztreonam derivatives provided by the present disclosure. The steps correspond to those disclosed in Examples 1-7.

A dash ("-") that is not between two letters or symbols is used to indicate a point of attachment for a moiety or substituent. For example, —CONH$_2$ is attached through the carbon atom.

"Alkyl" refers to a saturated or unsaturated, branched, or straight-chain, monovalent hydrocarbon radical derived by the removal of one hydrogen atom from a single carbon atom of a parent alkane, alkene, or alkyne. Examples of alkyl groups include methyl; ethyls such as ethanyl, ethenyl, and ethynyl; propyls such as propan-1-yl, propan-2-yl, prop-1-en-1-yl, prop-1-en-2-yl, prop-2-en-1-yl (allyl), prop-1-yn-1-yl, prop-2-yn-1-yl, etc.; butyls such as butan-1-yl, butan-2-yl, 2-methyl-propan-1-yl, 2-methyl-propan-2-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, but-1-yn-1-yl, but-1-yn-3-yl, but-3-yn-1-yl, etc.; and the like. The term "alkyl" includes groups having any degree or level of saturation, i.e., groups having exclusively carbon-carbon single bonds, groups having one or more carbon-carbon double bonds, groups having one or more carbon-carbon triple bonds, and groups having combinations of carbon-carbon single, double, and triple bonds. Where a specific level of saturation is intended, the terms alkanyl, alkenyl, and alkynyl are used. An alkyl group can be $C_{1-6}$ alkyl, $C_{1-5}$ alkyl, $C_{1-4}$ alkyl, $C_{1-3}$ alkyl, ethyl or methyl.

"Alkoxy" refers to a radical —OR where R is alkyl as defined herein. Examples of alkoxy groups include methoxy, ethoxy, propoxy, and butoxy. An alkoxy group can be $C_{1-6}$ alkoxy, $C_{1-5}$ alkoxy, $C_{1-4}$ alkoxy, $C_{1-3}$ alkoxy, ethoxy or methoxy.

"Aryl" by itself or as part of another substituent refers to a monovalent aromatic hydrocarbon radical derived by the removal of one hydrogen atom from a single carbon atom of a parent aromatic ring system. Aryl encompasses 5- and 6-membered carbocyclic aromatic rings, for example, benzene; bicyclic ring systems wherein at least one ring is carbocyclic and aromatic, for example, naphthalene, indane, and tetralin; and tricyclic ring systems wherein at least one ring is carbocyclic and aromatic, for example, fluorene. Aryl encompasses multiple ring systems having at least one carbocyclic aromatic ring fused to at least one carbocyclic aromatic ring, cycloalkyl ring, or heterocycloalkyl ring. For example, aryl includes a phenyl ring fused to a 5- to 7-membered heterocycloalkyl ring containing one or more heteroatoms selected from N, O, and S. For such fused, bicyclic ring systems wherein only one of the rings is a carbocyclic aromatic ring, the radical carbon atom may be at the carbocyclic aromatic ring or at the heterocycloalkyl ring. Examples of aryl groups include groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, pentacene, pentalene, pentaphene, perylene, phenalene, phenanthrene, picene, pleiadene, pyrene, pyranthrene, rubicene, triphenylene, trinaphthalene, and the like. An aryl group can be $C_{6-10}$ aryl, $C_{6-9}$ aryl, $C_{6-8}$ aryl, or phenyl. Aryl, however, does not encompass or overlap in any way with heteroaryl, separately defined herein.

"Arylalkyl" refers to an acyclic alkyl radical in which one of the hydrogen atoms bonded to a carbon atom is replaced with an aryl group. Examples of arylalkyl groups include benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl, or arylalkynyl is used. An arylalkyl group can be $C_{7-16}$ arylalkyl, e.g., the alkanyl, alkenyl or alkynyl moiety of the arylalkyl group is $C_1$-6 and the aryl moiety is $C_{6-10}$. An arylalkyl group can be $C_{7-16}$ arylalkyl, e.g., the alkanyl, alkenyl or alkynyl moiety of the arylalkyl group is $C_1$-6 and the aryl moiety is $C_{6-10}$. An arylalkyl group can be $C_{7-9}$ arylalkyl, wherein the alkyl moiety is $C_{1-3}$ alkyl and the aryl moiety is phenyl. An arylalkyl group can be $C_{7-16}$ arylalkyl, $C_{7-14}$ arylalkyl, $C_{7-12}$ arylalkyl, $C_{7-10}$ arylalkyl, $C_{7-8}$ arylalkyl, or benzyl.

"Bioavailability" refers to the rate and amount of a drug that reaches the systemic circulation of a patient following administration of the drug or prodrug thereof to the patient and can be determined by evaluating, for example, the plasma or blood concentration-versus-time profile for a drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or form of drug to the patient, and $T_{max}$ is the time to the maximum concentration ($C_{max}$) of a drug in the plasma or blood of a patient following administration of a dose of the drug or form of drug to the patient.

"Oral bioavailability" (F %) refers to the fraction of an oral administered drug that reaches systemic circulation. Oral bioavailability is a product of fraction absorbed, fraction escaping gut-wall elimination, and fraction escaping hepatic elimination; and the factors that influence bioavailability can be divided into physiological, physicochemical, and biopharmaceutical factors.

"Compounds" and moieties disclosed herein include any specific compounds within the disclosed formula. Compounds may be identified either by chemical structure and/or by chemical name. Compounds are named using the ChemBioDraw Ultra 14.0.0.117 (CambridgeSoft, Cambridge, Mass.) nomenclature program. When the chemical structure and chemical name conflict, the chemical structure is determinative of the identity of the compound. The compounds described herein may comprise one or more stereogenic centers and/or double bonds and therefore may exist as stereoisomers such as double-bond isomers (i.e., geometric isomers), enantiomers, diastereomers, or atropisomers.

Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled in the art.

Compounds and moieties disclosed herein include optical isomers of compounds and moieties, racemates thereof, and other mixtures thereof. In such embodiments, the single enantiomers or diastereomers may be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column with chiral stationary phases. In addition, compounds include (Z)- and (E)-forms (or cis- and trans-forms) of compounds with double bonds either as single geometric isomers or mixtures thereof.

Compounds and moieties may also exist in several tautomeric forms including the enol form, the keto form, and mixtures thereof. Accordingly, the chemical structures depicted herein encompass all possible tautomeric forms of the illustrated compounds. Compounds may exist in unsolvated forms as well as solvated forms, including hydrated forms. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

"Cycloalkyl" refers to a saturated or partially unsaturated cyclic alkyl radical. A cycloalkyl group can be $C_{3-6}$ cycloalkyl, $C_{3-5}$ cycloalkyl, $C_{5-6}$ cycloalkyl, cyclopropyl, cyclopentyl, or cyclohexyl. A cycloalkyl can be selected from cyclopropyl, cyclobutyl, cyclopentyl, and cyclohexyl.

"Cycloalkylalkyl" refers to an acyclic alkyl radical in which one of the hydrogen atoms bonded to a carbon atom is replaced with a cycloalkyl group as defined herein. Where specific alkyl moieties are intended, the nomenclature cycloalkylalkyl, cycloalkylalkenyl, or cycloalkylalkynyl is used. A cycloalkylalkyl group can be $C_{4-30}$ cycloalkylalkyl, e.g., the alkanyl, alkenyl, or alkynyl moiety of the cycloalkylalkyl group is $C_{1-10}$ and the cycloalkyl moiety of the cycloalkylalkyl moiety is $C_{3-20}$. A cycloalkylalkyl group can be $C_{4-20}$ cycloalkylalkyl, e.g., the alkanyl, alkenyl, or alkynyl moiety of the cycloalkylalkyl group is $C_{1-8}$ and the cycloalkyl moiety of the cycloalkylalkyl group is $C_{3-12}$. A cycloalkylalkyl can be $C_{4-9}$ cycloalkylalkyl, wherein the alkyl moiety of the cycloalkylalkyl group is $C_{1-3}$ alkyl, and the cycloalkyl moiety of the cycloalkylalkyl group is $C_{3-6}$ cycloalkyl. A cycloalkylalkyl group can be $C_{4-12}$ cycloalkylalkyl, $C_{4-10}$ cycloalkylalkyl, $C_{4-8}$ cycloalkylalkyl, and $C_{4-6}$ cycloalkylalkyl. A cycloalkylalkyl group can be cyclopropylmethyl (—CH$_2$-cyclo-C$_3$H$_5$), cyclopentylmethyl (—CH$_2$-cyclo-C$_5$H$_9$), or cyclohexylmethyl (—CH$_2$-cyclo-C$_6$H$_{11}$). A cycloalkylalkyl group can be cyclopropylethenyl (—CH=CH-cyclo-C$_3$H$_5$), cyclopentylethynyl (—C≡C-cycl-C$_5$H$_9$), or the like.

"Cycloalkylheteroalkyl" by itself or as part of another substituent refers to a heteroalkyl group in which one or more of the carbon atoms (and certain associated hydrogen atoms) of an alkyl group are independently replaced with the same or different heteroatomic group or groups and in which one of the hydrogen atoms bonded to a carbon atom is replaced with a cycloalkyl group. Where specific alkyl moieties are intended, the nomenclature cycloalkylheteroalkanyl, cycloalkylheteroalkenyl, and cycloalkylheteroalkynyl is used. In a cycloalkylheteroalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group is —O— or —NH—.

"Cycloalkyloxy" refers to a radical —OR where R is cycloalkyl as defined herein. Examples of cycloalkyloxy groups include cyclopropyloxy, cyclobutyloxy, cyclopentyloxy, and cyclohexyloxy. A cycloalkyloxy group can be $C_{3-6}$ cycloalkyloxy, $C_{3-5}$ cycloalkyloxy, $C_{5-6}$ cycloalkyloxy, cyclopropyloxy, cyclobutyloxy, cyclopentyloxy, or cyclohexyloxy.

"Disease" refers to a disease, disorder, condition, or symptom of any of the foregoing.

"Drug" as defined under 21 U.S.C. § 321(g)(1) means "(A) articles recognized in the official United States Pharmacopoeia, official Homeopathic Pharmacopoeia of the United States, or official National Formulary, or any supplement to any of them; and (B) articles intended for use in the diagnosis, cure, mitigation, treatment, or prevention of disease in man or other animals; and (C) articles (other than food) intended to affect the structure or any function of the body of man or other animals . . . .".

"Fluoroalkyl" refers to an alkyl group as defined herein in which one or more of the hydrogen atoms is replaced with a fluoro. A fluoroalkyl group can be $C_{1-6}$ fluoroalkyl, $C_{1-5}$ fluoroalkyl, $C_{1-4}$ fluoroalkyl, or $C_{1-3}$ fluoroalkyl. A fluoroalkyl group can be pentafluoroethyl (—CF$_2$CF$_3$), or trifluoromethyl (—CF$_3$).

"Fluoroalkoxy" refers to an alkoxy group as defined herein in which one or more of the hydrogen atoms is replaced with a fluoro. A fluoroalkoxy group can be $C_{1-6}$ fluoroalkoxy, $C_{1-5}$ fluoroalkoxy, $C_{1-4}$ fluoroalkoxy $C_{1-3}$, fluoroalkoxy, —OCF$_2$CF$_3$ or —OCF$_3$.

"Halogen" refers to a fluoro, chloro, bromo, or iodo group.

"Heteroalkoxy" refers to an alkoxy group in which one or more of the carbon atoms are replaced with a heteroatom. A heteroalkoxy group can be $C_{1-6}$ heteroalkoxy, $C_{1-5}$ heteroalkoxy, $C_{1-4}$ heteroalkoxy, or $C_{1-3}$ heteroalkoxy. In a heteroalkoxy, the heteroatomic group can be selected from —O—, —S—, —NH—, —NR— where R is $C_{1-6}$ alkyl, —SO$_2$—, and —SO$_2$—, or the heteroatomic group can be selected from —O— and —NH—, or the heteroatomic group is —O— and —NH—. A heteroalkoxy group can be $C_{1-6}$ heteroalkoxy, $C_{1-5}$ heteroalkoxy, $C_{1-4}$ heteroalkoxy, or $C_{1-3}$ heteroalkoxy.

"Heteroalkyl" by itself or as part of another substituent refer to an alkyl group in which one or more of the carbon atoms (and certain associated hydrogen atoms) are independently replaced with the same or different heteroatomic group or groups. Examples of heteroatomic groups include —O—, —S—, —NH—, —NR—, —O—O—, —S—S—, =N—N=, —N=N—, —N=N—NR—, —PR—, —P(O)OR—, —P(O)R—, —POR—, —SO—, —SO$_2$—, and —Sn(R)$_2$—, where each R is independently selected from hydrogen, $C_{1-6}$ alkyl, substituted $C_{1-6}$ alkyl, $C_{6-12}$ aryl, substituted $C_{6-12}$ aryl, $C_{7-13}$ arylalkyl, substituted $C_{7-13}$ arylalkyl, $C_{3-7}$ cycloalkyl, substituted $C_{3-7}$ cycloalkyl, $C_{3-7}$ heterocycloalkyl, substituted $C_{3-7}$ heterocycloalkyl, $C_{1-6}$ heteroalkyl, substituted $C_{1-6}$ heteroalkyl, $C_{6-12}$ heteroaryl, substituted $C_{6-12}$ heteroaryl, $C_{7-13}$ heteroarylalkyl, and substituted $C_{7-18}$ heteroarylalkyl. Each R can be independently selected from hydrogen and $C_{1-3}$ alkyl. Reference to, for example, a $C_{1-6}$ heteroalkyl, means a $C_{1-6}$ alkyl group in which at least one of the carbon atoms (and certain associated hydrogen atoms) is replaced with a heteroatom. For example, $C_{1-6}$ heteroalkyl includes groups having five carbon atoms and one heteroatom, groups having four carbon atoms and two heteroatoms, etc. In a heteroalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—. A heteroalkyl group can be $C_{1-6}$ heteroalkyl, $C_{1-5}$ heteroalkyl, or $C_{1-4}$ heteroalkyl, or $C_{1-3}$ heteroalkyl.

"Heteroaryl" by itself or as part of another substituent refers to a monovalent heteroaromatic radical derived by the removal of one hydrogen atom from a single atom of a parent heteroaromatic ring system. Heteroaryl encompasses multiple ring systems having at least one heteroaromatic ring fused to at least one other ring, which may be aromatic or non-aromatic. For example, heteroaryl encompasses bicyclic rings in which one ring is heteroaromatic and the second ring is a heterocycloalkyl ring. For such fused, bicyclic heteroaryl ring systems wherein only one of the rings contains one or more heteroatoms, the radical carbon may be at the aromatic ring or at the heterocycloalkyl ring. When the total number of N, S, and O atoms in the heteroaryl group exceeds one, the heteroatoms may or may not be adjacent to one another. The total number of heteroatoms in the heteroaryl group is not more than two. In a heteroaryl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—. A heteroaryl group can be selected from $C_{5-10}$ heteroaryl, $C_{5-9}$ heteroaryl, $C_{5-8}$ heteroaryl, $C_{5-7}$ heteroaryl, $C_{5-6}$ heteroaryl, $C_5$ heteroaryl or $C_6$ heteroaryl.

Examples of heteroaryl groups include groups derived from acridine, arsindole, carbazole, α-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, thiazolidine, and oxazolidine. A heteroaryl groups can be derived, for example, from thiophene, pyrrole, benzothiophene, benzofuran, indole, pyridine, quinoline, imidazole, oxazole, or pyrazine. For example, a heteroaryl can be $C_5$ heteroaryl and can be selected from furyl, thienyl, pyrrolyl, imidazolyl, pyrazolyl, isothiazolyl, or isoxazolyl. A heteroaryl can be $C_6$ heteroaryl, and can be selected from pyridinyl, pyrazinyl, pyrimidinyl, and pyridazinyl.

"Heteroarylalkyl" refers to an arylalkyl group in which one of the carbon atoms (and certain associated hydrogen atoms) is replaced with a heteroatom. A heteroarylalkyl group can be $C_{6-16}$ heteroarylalkyl, $C_{6-14}$ heteroarylalkyl, $C_{6-12}$ heteroarylalkyl, $C_{6-10}$ heteroarylalkyl, $C_{6-8}$ heteroarylalkyl, or $C_7$ heteroarylalkyl, or $C_6$ heteroarylalkyl. In a heteroarylalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Heterocycloalkyl" by itself or as part of another substituent refers to a saturated or unsaturated cyclic alkyl radical in which one or more carbon atoms (and certain associated hydrogen atoms) are independently replaced with the same or different heteroatom; or to a parent aromatic ring system in which one or more carbon atoms (and certain associated hydrogen atoms) are independently replaced with the same or different heteroatom such that the ring system violates the Hückel-rule. Examples of heteroatoms to replace the carbon atom(s) include N, P, O, S, and Si. Examples of heterocycloalkyl groups include groups derived from epoxides, azirines, thiiranes, imidazolidine, morpholine, piperazine, piperidine, pyrazolidine, pyrrolidine, and quinuclidine. A heterocycloalkyl can be $C_5$ heterocycloalkyl and is selected from pyrrolidinyl, tetrahydrofuranyl, tetrahydrothiophenyl, imidazolidinyl, oxazolidinyl, thiazolidinyl, doxolanyl, and dithiolanyl. A heterocycloalkyl can be $C_6$ heterocycloalkyl and can be selected from piperidinyl, tetrahydropyranyl, piperizinyl, oxazinyl, dithianyl, and dioxanyl. A heterocycloalkyl group can be $C_{3-6}$ heterocycloalkyl, $C_{3-5}$ heterocycloalkyl, $C_{5-6}$ heterocycloalkyl, $C_5$ heterocycloalkyl or $C_6$ heterocycloalkyl. In a heterocycloalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Heterocycloalkylalkyl" refers to a cycloalkylalkyl group in which one or more carbon atoms (and certain associated hydrogen atoms) of the cycloalkyl ring are independently replaced with the same or different heteroatom. A heterocycloalkylalkyl can be $C_{4-12}$ heterocycloalkylalkyl, $C_{4-10}$ heterocycloalkylalkyl, $C_{4-8}$ heterocycloalkylalkyl, $C_{4-6}$ heterocycloalkylalkyl, $C_{6-7}$ heterocycloalkylalkyl, or $C_6$ heterocycloalkylalkyl or $C_7$ heterocycloalkylalkyl. In a heterocycloalkylalkyl, the heteroatomic group can be selected from —O—, —S—, —NH—, —N(—CH$_3$)—, —SO—, and —SO$_2$—, or the heteroatomic group can be selected from —O— and —NH—, or the heteroatomic group can be —O— or —NH—.

"Organyl" refers to an organic substituent group, regardless of functional type, having one free valence electron at a carbon atom.

"Hydrates" refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism.

"Metabolic intermediate" refers to a compound that is formed in vivo by metabolism of a parent compound and that further undergoes reaction in vivo to release an active agent. Compounds of Formula (1) are protected sulfonate nucleophile prodrugs of aztreonam that are metabolized in vivo to provide the corresponding metabolic intermediates. Metabolic intermediates undergo nucleophilic cyclization to release aztreonam and one or more reaction products. It is desirable that the reaction products or metabolites thereof not be toxic.

"Neopentyl" refers to a radical in which a methylene carbon is bonded to a carbon atom, which is bonded to three non-hydrogen substituents. Examples of non-hydrogen substituents include carbon, oxygen, nitrogen, and sulfur. Each of the three non-hydrogen substituents can be carbon. Two of the three non-hydrogen substituents can be carbon, and the third non-hydrogen substituent can be selected from oxygen and nitrogen. A neopentyl group can have the structure:

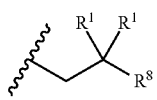

where each $R^1$ and $R^8$ are as defined herein.

"Parent aromatic ring system" refers to an unsaturated cyclic or polycyclic ring system having a conjugated n electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Examples of parent aromatic ring systems include aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene.

"Parent heteroaromatic ring system" refers to an aromatic ring system in which one or more carbon atoms (and any associated hydrogen atoms) are independently replaced with the same or different heteroatom in such a way as to maintain the continuous n-electron system characteristic of aromatic systems and a number of n-electrons corresponding to the Hückel rule (4n+2). Examples of heteroatoms to replace the carbon atoms include N, P, O, S, and Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Examples of parent heteroaromatic ring systems include arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiophene, triazole, xanthene, thiazolidine, and oxazolidine.

"Patient" refers to a mammal, for example, a human.

"Pharmaceutically acceptable" refers to approved or approvable by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound, which possesses the desired pharmacological activity of the parent compound. Such salts include acid addition salts, formed with inorganic acids and one or more protonable functional groups such as primary, secondary, or tertiary amines within the parent compound. Examples of suitable inorganic acids include hydrochloric acid, hydrobromic acid, sulfuric acid, nitric acid, phosphoric acid, and the like. A salt can be formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like. A salt can be formed when one or more acidic protons present in the parent compound are replaced by a metal ion, e.g., an alkali metal ion, an alkaline earth ion, or an aluminum ion, or combinations thereof; or coordinates with an organic base such as ethanolamine, diethanolamine, triethanolamine, N-methylglucamine, and the like. A pharmaceutically acceptable salt can be the hydrochloride salt. A pharmaceutically acceptable salt can be the sodium salt. In compounds having two or more ionizable groups, a pharmaceutically acceptable salt can comprise one or more counterions, such as a bi-salt, for example, a dihydrochloride salt.

The term "pharmaceutically acceptable salt" includes hydrates and other solvates, as well as salts in crystalline or non-crystalline form. Where a particular pharmaceutically acceptable salt is disclosed, it is understood that the particular salt (e.g., a hydrochloride salt) is an example of a salt, and that other salts may be formed using techniques known to one of skill in the art. Additionally, one of skill in the art would be able to convert the pharmaceutically acceptable salt to the corresponding compound, free base and/or free acid, using techniques generally known in the art.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (1a)-(1d) or a pharmaceutically acceptable salt thereof and at least one pharmaceutically acceptable vehicle, with which the compound of Formula (1a)-(1d) or a pharmaceutically acceptable salt thereof is administered to a patient. Pharmaceutically acceptable vehicles are known in the art.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease). In some embodiments, "preventing" or "prevention" refers to reducing symptoms of the disease by administering a compound provided by the present disclosure in a preventative fashion. The application of a therapeutic agent for preventing or prevention of a disease of disorder is known as 'prophylaxis.' Compounds provided by the present disclosure can provide superior prophylaxis because of lower long-term side effects over long time periods.

"Prodrug" refers to a derivative of a drug molecule that requires a transformation within the body to release the active drug. Prodrugs are frequently, although not necessarily, pharmacologically inactive until converted to the parent drug. Prodrugs may be obtained by bonding a promoiety (defined herein) typically via a functional group, to a drug. For example, referring to compounds of Formula (1a)-(1d), promoieties bonded to the drug aztreonam, via the sulfate group aztreonam of Compounds of Formula (1a)-(1d) are prodrugs of aztreonam that can be metabolized within a patient's body to release aztreonam.

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or it may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation of a patient to which the prodrug is administered or the acidic conditions of the stomach or the agent may be supplied exogenously. For example, for a compound of Formula (2), a promoiety can have the structure:

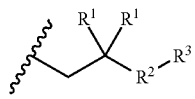

where $R^1$, $R^2$, and $R^3$ can be defined herein.

"Single bond" as in the expression "$R^2$ is selected from a single bond" refers to a moiety in which $R^2$ and two of the bonds to $R^2$ correspond to a single bond. For example, in a moiety having the structure —$C(R^1)_2$—$R^2$-$R^3$, where $R^2$ is a single bond, —$R^2$— corresponds to a single bond (—), and the moiety has the structure —$C(R')_2$—$R^3$.

"Solvate" refers to a molecular complex of a compound with one or more solvent molecules in a stoichiometric or non-stoichiometric amount. Such solvent molecules are those commonly used in the pharmaceutical arts, which are known to be innocuous to a patient, such as water or ethanol. A molecular complex of a compound or moiety of a compound and a solvent can be stabilized by non-covalent intra-molecular forces such as, for example, electrostatic forces, van der Waals forces, or hydrogen bonds. The term "hydrate" refers to a solvate in which the one or more solvent molecules is water.

"Solvates" refers to incorporation of solvents into to the crystal lattice of a compound described herein, in stoichiometric proportions, resulting in the formation of an adduct. Methods of making solvates include, for example, storage in an atmosphere containing a solvent, dosage forms that include the solvent, or routine pharmaceutical processing steps such as, for example, crystallization (i.e., from solvent or mixed solvents) vapor diffusion. Solvates may also be formed, under certain circumstances, from other crystalline solvates or hydrates upon exposure to the solvent or upon suspension material in solvent. Solvates may crystallize in more than one form resulting in solvate polymorphism.

"Substituted" refers to a group in which one or more hydrogen atoms are independently replaced with the same or different substituent(s). Each substituent can be independently selected from deuterio, halogen, —OH, —CN, —$CF_3$, —$OCF_3$, =O, —$NO_2$, $C_{1-6}$ alkoxy, $C_{1-6}$ alkyl, —COOR, —$NR_2$, and —$CONR_2$; wherein each R is independently selected from hydrogen and $C_{1-6}$ alkyl. Each substituent can be independently selected from deuterio, halogen, —$NH_2$, —OH, $C_{1-3}$ alkoxy, and $C_{1-3}$ alkyl, trifluoromethoxy, and trifluoromethyl. Each substituent can be independently selected from deuterio, —OH, methyl, ethyl, trifluoromethyl, methoxy, ethoxy, and trifluoromethoxy. Each substituent can be selected from deuterio, $C_{1-3}$ alkyl, =O, $C_{1-3}$ alkyl, $C_{1-3}$ alkoxy, and phenyl. Each substituent can be selected from deuterio, —OH, —$NH_2$, $C_{1-3}$ alkyl, and $C_{1-3}$ alkoxy.

"Sustained release" refers to release of a compound from a dosage form of a pharmaceutical composition at a rate effective to achieve a therapeutic or prophylactic concentration of the compound or active metabolite thereof, in the systemic circulation of a patient over a prolonged period of time relative to that achieved by administration of an immediate release formulation of the same compound by the same route of administration. In some embodiments, release of a compound occurs over a time period of at least about 4 hours, such as at least about 8 hours, at least about 12 hours, at least about 16 hours, at least about 20 hours, and in some embodiments, at least about 24 hours.

"Treating" or "treatment" of a disease refers to arresting or ameliorating a disease or at least one of the clinical symptoms of a disease or disorder, reducing the risk of acquiring a disease or at least one of the clinical symptoms of a disease, reducing the development of a disease or at least one of the clinical symptoms of the disease or reducing the risk of developing a disease or at least one of the clinical symptoms of a disease. "Treating" or "treatment" also refers to inhibiting the disease, either physically, (e.g., stabilization of a discernible symptom), physiologically, (e.g., stabilization of a physical parameter), or both, and to inhibiting at least one physical parameter or manifestation that may or may not be discernible to the patient. "Treating" or "treatment" also refers to delaying the onset of the disease or delaying the onset of at least one or more symptoms thereof in a patient who may be exposed to or predisposed to a disease or disorder even though that patient does not yet experience or display symptoms of the disease.

"Therapeutically effective amount" refers to the amount of a compound that, when administered to a patient for treating a disease, or at least one of the clinical symptoms of a disease, is sufficient to affect such treatment of the disease or symptom thereof. The "therapeutically effective amount" may vary depending, for example, on the compound, the disease and/or symptoms of the disease, severity of the disease and/or symptoms of the disease or disorder, the age, weight, and/or health of the patient to be treated, and the judgment of the prescribing physician. An appropriate amount in any given instance may be ascertained by those skilled in the art or capable of determination by routine experimentation.

"Therapeutically effective dose" refers to a dose that provides effective treatment of a disease or disorder in a patient. A therapeutically effective dose may vary from compound to compound, and from patient to patient, and may depend upon factors such as the condition of the patient and the route of delivery. A therapeutically effective dose may be determined in accordance with routine pharmacological procedures known to those skilled in the art.

"Vehicle" refers to a diluent, excipient or carrier with which a compound is administered to a patient. A vehicle can be a pharmaceutically acceptable vehicle. Pharmaceutically acceptable vehicles are known in the art.

Reference is now made in detail to certain embodiments of compounds, compositions, and methods. The disclosed embodiments are not intended to be limiting of the claims. To the contrary, the claims are intended to cover all alternatives, modifications, and equivalents.

Aztreonam is a monobactam antibiotic used to treat infections caused primarily by gram-negative bacteria. Aztreonam has poor oral bioavailability. Compounds provided by the present disclosure are N-sulfonate ester prodrugs of aztreonam. The aztreonam N-sulfonate ester prodrugs exhibit enhanced oral bioavailability compared to aztreonam. In the aztreonam prodrugs a nucleophilic moiety is positioned proximate the sulfonyl group. In vivo, the nucleophilic moiety reacts to release aztreonam in the systemic circulation. Aztreonam, (2-((((E)-1-(2-aminothiazol-4-yl)-2-(((2S,3S)-2-methyl-4-oxo-1-sulfoazetidin-3-yl)amino)-2-oxoethylidene)amino)oxy)-2-methylpropanoic acid), has the structure of Formula (1):

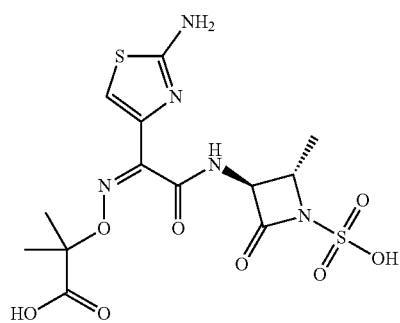

Compounds provided by the present disclosure include aztreonam derivatives having the structure of Formula (1a):

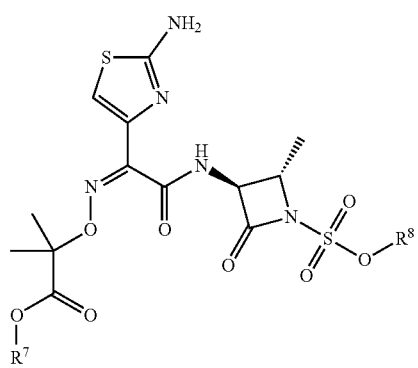

or a pharmaceutically acceptable salt thereof, wherein,
R$^7$ is selected from hydrogen, C$_{1-6}$ alkyl, C$_{5-8}$ cycloalkyl, C$_{6-12}$ cycloalkylalkyl, C$_{2-6}$ heteroalkyl, C$_{5-8}$ heterocycloalkyl, C$_{6-12}$ heterocycloalkylalkyl, substituted C$_{1-6}$ alkyl, substituted C$_{5-8}$ cycloalkyl, substituted C$_{6-12}$ cycloalkylalkyl, substituted C$_{2-6}$ heteroalkyl, substituted C$_{5-8}$ heterocycloalkyl, and substituted C$_{6-12}$ heterocycloalkylalkyl; and R$^8$ is selected from C$_{1-20}$ alkyl, C$_{1-20}$ alkanecycloalkyl, C$_{1-20}$ alkanearyl, C$_{1-20}$ heteroalkyl, C$_{1-20}$ heteroalkanecycloalkyl, C$_{1-20}$ heteroalkanearyl, substituted C$_{1-20}$ alkyl, substituted C$_{1-20}$ alkanecycloalkyl, substituted C$_{1-20}$ alkanearyl, substituted C$_{1-20}$ heteroalkyl, substituted C$_{1-20}$ heteroalkanecycloalkyl, and substituted C$_{1-20}$ heteroalkanearyl.

In compounds of Formula (1a), R$^8$ can have the structure of Formula (2):

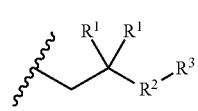

wherein,
each R$^1$ is independently C$_{1-6}$ alkyl, or each R$^1$ and the geminal carbon atom to which each R$^1$ is bonded forms a C$_{3-6}$ cycloalkyl ring, a C$_{3-6}$ heterocycloalkyl ring, a substituted C$_{3-6}$ cycloalkyl ring, or a substituted C$_{3-6}$ heterocycloalkyl ring;

R$^2$ is selected from a single bond, C$_{1-6}$ alkanediyl, C$_{1-6}$ heteroalkanediyl, C$_{5-6}$ cycloalkanediyl, C$_{5-6}$ heterocycloalkanediyl, C$_6$ arenediyl, C$_{5-6}$ heteroarenediyl, substituted C$_{1-6}$ alkanediyl, substituted C$_{1-6}$ heteroalkanediyl, substituted C$_{5-6}$ cycloalkanediyl, substituted C$_{5-6}$ heterocycloalkanediyl, substituted C$_6$ arenediyl, and substituted C$_{5-6}$ heteroarenediyl; and R$^3$ is selected from C$_{1-6}$ alkyl, —O—C(O)—R$^4$, —S—C(O)—R$^4$, —NH—C(O)—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—C(O)—S—R$^4$, —O—C(O)—NH—R$^4$, —S—S—R$^4$, —S—R$^4$, —NH—R$^4$, —CH(—NH$_2$)(—R$^4$), C$_{5-6}$ heterocycloalkyl, C$_{5-6}$ heteroaryl, substituted C$_{5-6}$ cycloalkyl, substituted C$_{5-6}$ heterocycloalkyl, substituted C$_{5-6}$ aryl, and substituted C$_{5-6}$ heteroaryl, wherein,
R$^4$ is selected from hydrogen, C$_{1-8}$ alkyl, C$_{1-8}$ heteroalkyl, C$_{5-8}$ cycloalkyl, C$_{5-8}$ heterocycloalkyl, C$_{5-10}$ cycloalkylalkyl, C$_{5-10}$ heterocycloalkylalkyl, C$_{6-8}$ aryl, C$_{5-8}$ heteroaryl, C$_{7-10}$ arylalkyl, C$_{5-10}$ heteroarylalkyl, substituted C$_{1-8}$ alkyl, substituted C$_{1-8}$ heteroalkyl, substituted C$_{5-8}$ cycloalkyl, substituted C$_{5-8}$ heterocycloalkyl, substituted C$_{5-10}$ cycloalkylalkyl, substituted C$_{5-10}$ heterocycloalkylalkyl, substituted C$_{6-8}$ aryl, substituted C$_{5-8}$ heteroaryl, substituted C$_{7-10}$ arylalkyl, and substituted C$_{5-10}$ heteroarylalkyl.

Compounds provided by the present disclosure can have the structure of Formula (1b):

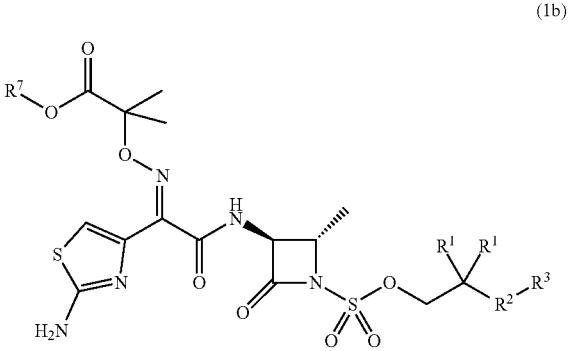

or a pharmaceutically acceptable salt thereof, wherein each $R^1$, $R^2$, $R^3$, and $R^7$ are defined as for Formula (1a) and Formula (2).

In compounds of Formula (1a)-(1b), each substituent can independently be selected from deuterio, —OH, —CN, —CF$_3$, —OCF$_3$, =O, —NO$_2$, $C_{1-6}$ alkoxy, $C_{1-6}$ alkyl, —COOR, —NR$_2$, and —CONR$_2$; wherein each R can be independently selected from hydrogen and $C_{1-6}$ alkyl, such has methyl, ethyl, n-propyl, isopropyl, n-butyl, tert-butyl, or iso-butyl.

In compounds of Formula (1a)-(1b), a substituent group can be a nucleophilic group. Nucleophilic groups are functional group having a reactive pair of electrons and having the ability of forming a chemical bond by donating electrons. Examples of suitable nucleophilic groups include esters, carboxylates, sulfonates, substituted or unsubstituted amines, alcohols (hydroxyl), thiols, sulfides, hydroxylamines, and imines. Other examples of suitable nucleophilic groups include —OH, —CF$_3$, —O—CF$_3$, —NO$_2$, —O—C(O)—R$^4$, —S—C(O)—R$^4$, —NH—C(O)—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—C(O)—S—R$^4$, —O—C(O)—NH—R$^4$, —S—S—R$^4$, —S—R$^4$, —NH—R$^4$, —CH(—NH$_2$)(—R$^4$), where each R$^4$ can be independently selected from hydrogen, $C_{1-6}$ alkyl, $C_{1-6}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{6-8}$ heteroaryl, $C_{5-10}$ arylalkyl, $C_{10}$ heteroarylalkyl, substituted $C_{1-6}$ alkyl, substituted $C_{1-6}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{6-8}$ heteroaryl, substituted $C_{5-10}$ arylalkyl, and substituted $C_{5-10}$ heteroarylalkyl.

In compounds of Formula (1a)-(1b), each substituent can independently be selected from —OH, —CF$_3$, —O—CF$_3$, —NO$_2$, —O—C(O)—R$^4$, —S—C(O)—R$^4$, —NH—C(O)—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—C(O)—S—R$^4$, —O—C(O)—NH—R$^4$, —S—S—R$^4$, —S—R$^4$, —NH—R$^4$, —CH(—NH$_2$)(—R$^4$), wherein each R$^4$ can be selected from hydrogen, $C_{1-8}$alkyl, and $C_{1-8}$ heteroalkyl.

In compounds of Formula (1a)-(1b), $R^7$ can be hydrogen.

In compounds of Formula (1a)-(1b), $R^7$ can be $C_{1-3}$ alkyl, such as methyl, ethyl, n-propyl, or iso-propyl.

In compounds of Formula (1a)-(1b), $R^7$ can be selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl.

In compounds of Formula (1a)-(1b), $R^7$ can be selected from hydrogen, $C_{1-6}$ alkyl, $C_{5-8}$ cycloalkyl, and $C_{6-12}$ cycloalkylalkyl.

In compounds of Formula (1a)-(1b), $R^7$ can be selected from hydrogen, ethyl, tert-butyl, hexyl, —(CH$_2$)$_2$O—CH$_3$, and

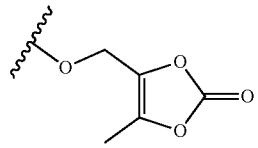 [SMILES: *OCc1oc(=O)oc1C]

(4-(yl-methyl)-5-methyl-1,3-dioxol-2-one).

In compounds of Formula (1a)-(1b), R can be selected from hydrogen and $C_{1-6}$ alkyl.

In moieties of Formula (2) and compounds of Formula (1b), each $R^1$ can independently be $C_{1-6}$ alkyl.

In moieties of Formula (2) and compounds of Formula (1b), each $R^1$ can independently be methyl, ethyl, or n-propyl.

In moieties of Formula (2) and compounds of Formula (1b), each $R^1$ can be the same and can be methyl, ethyl, or n-propyl.

In moieties of Formula (2) and compounds of Formula (1b), each $R^1$ can be methyl.

In moieties of Formula (2) and compounds of Formula (1b), each $R^1$ together with the geminal carbon atom to which each $R^1$ can be bonded can form a $C_{3-6}$ cycloalkyl ring or a substituted $C_{3-6}$ cycloalkyl ring.

In moieties of Formula (2) and compounds of Formula (1b), each $R^1$ together with the geminal carbon atom to which each $R^1$ is bonded can form a $C_{3-6}$ cycloalkyl ring. For example, each $R^1$ together with the geminal carbon atom to which each $R^1$ is bonded can form a cyclopropyl ring, a cyclobutyl ring, a cyclopentyl ring, or a cyclohexyl ring.

In moieties of Formula (2) and compounds of Formula (1b), each $R^1$ together with the geminal carbon atom to which each $R^1$ is bonded can form a $C_{3-6}$ heterocycloalkyl ring or a substituted $C_{3-6}$ heterocycloalkyl ring.

In moieties of Formula (2) and compounds of Formula (1b), $R^2$ can be selected from a single bond, $C_{1-2}$ alkanediyl, and substituted $C_{1-2}$ alkanediyl.

In moieties of Formula (2) and compounds of Formula (1b), $R^2$ can be a single bond.

In moieties of Formula (2) and compounds of Formula (1b), $R^2$ can be a single bond; and $R^3$ can be $C_{1-6}$ alkyl.

In moieties of Formula (2) and compounds of Formula (1b), $R^2$ can be selected from $C_{1-2}$ alkanediyl and substituted $C_{1-2}$ alkanediyl.

In moieties of Formula (2) and compounds of Formula (1b), $R^2$ can be methanediyl, ethanediyl, substituted methanediyl, or substituted ethanediyl.

In moieties of Formula (2) and compounds of Formula (1b), $R^2$ can be substituted $C_{1-2}$ alkanediyl where the substituent group can be selected from —OH, —CN, —CF$_3$, —OCF$_3$, =O, —NO$_2$, $C_{1-6}$ alkoxy, $C_{1-6}$ alkyl, —COOR, —NR$_2$, and —CONR$_2$; wherein each R can be independently selected from hydrogen and $C_{1-6}$ alkyl.

In moieties of Formula (2) and compounds of Formula (1b), $R^2$ can be substituted $C_{1-2}$ alkanediyl where the substituent group can be a nucleophilic group. For example, $R^2$ can be substituted $C_{1-2}$ alkanediyl where the substituent group can be selected from —OH, —CF$_3$, —O—CF$_3$, —NO$_2$, —O—C(O)—R$^4$, —S—C(O)—R$^4$, —NH—C(O)—R$^4$, —S—C(O)—O—R$^4$, —NH—C(O)—O—R$^4$, —C(O)—O—R$^4$, —C(O)—S—R$^4$, —C(O)—NH—R$^4$, —O—C(O)—O—R$^4$, —O—C(O)—S—R$^4$, —O—C(O)—NH—R$^4$, —S—S—R$^4$, —S—R$^4$, —NH—R$^4$, —CH(—NH$_2$)(—R$^4$), where each R$^4$ is defined as for Formula (1a), or each R$^4$ can be selected from hydrogen and $C_{1-8}$ alkyl.

In moieties of Formula (2) and compounds of Formula (1b), $R^2$ can be substituted $C_{1-2}$ alkanediyl where the substituent group can be selected from —OH, —O—C(O)—R$^4$, —S—C(O)—R$^4$, —NH—C(O)—R$^4$, —C(O)—O—R$^4$, —C(O)—S—R$^4$, —C(O)—NH—R$^4$, —S—S—R$^4$, —S—R$^4$, —NH—R$^4$, —CH(—NH$_2$)(—R$^4$), substituted $C_{5-6}$ aryl, —NHR$^4$, and —CH(—NH$_2$)(—R$^4$), where R$^4$ is defined as for Formula (1a), or each R$^4$ can be selected from hydrogen and $C_{1-8}$ alkyl.

In moieties of Formula (2) and compounds of Formula (1b), where $R^2$ can be substituted $C_{1-6}$ alkanediyl, substituted $C_{1-6}$ heteroalkanediyl, or substituted $C_5$-$_6$ arenediyl, the stereochemistry of the carbon atom to which the substituent group is bonded can be of the (S) configuration.

In moieties of Formula (2) and compounds of Formula (1b), where $R^2$ can be substituted $C_{1-6}$ alkanediyl, substituted $C_{1-6}$ heteroalkanediyl, or substituted $C_{5-6}$ arenediyl, the stereochemistry of the carbon atom to which the substituent group is bonded can be of the (R) configuration.

In moieties of Formula (2) and compounds of Formula (1b), $R^2$ can be selected from $C_{5-6}$ cycloalkanediyl, $C_{5-6}$ heterocycloalkanediyl, $C_{5-6}$ arenediyl, and $C_{5-6}$ heterocycloalkanediyl.

In moieties of Formula (2) and compounds of Formula (1b), $R^2$ can be cyclopenta-1,3-diene-diyl, substituted cyclopenta-1,3-diene-diyl, benzene-diyl or substituted benzene-diyl. For example, $R^2$ can be 1,2-benzene-diyl or substituted 1,2-benzene-diyl.

In moieties of Formula (2) and compounds of Formula (1b), $R^3$ can be selected from —O—C(O)—$R^4$, —S—C(O)—$R^4$, —NH—C(O)—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, and —CH(—NH$_2$)(—$R^4$), where $R^4$ is defined as for Formula (1), or each $R^4$ can be selected from hydrogen and $C_{1-8}$ alkyl.

In moieties of Formula (2) and compounds of Formula (1b), $R^3$ can be selected from —O—C(O)—$R^4$, —C(O)—O—$R^4$, —S—C(O)—$R^4$, —C(O)—S—$R^4$, —S—S—$R^4$, —NH—$R^4$, and —CH(—NH$_2$)(—$R^4$); where $R^4$ is defined as for Formula (1), or each $R^4$ can be selected from hydrogen and $C_{1-8}$ alkyl.

In moieties of Formula (2) and compounds of Formula (1b), $R^3$ can be —C(O)—O—$R^4$, where $R^4$ is defined as for Formula (1), or each $R^4$ can be selected from hydrogen and $C_{1-8}$ alkyl.

In compounds of Formula (1a)-(1b), $R^4$ can be selected from hydrogen, $C_{1-3}$ alkyl, $C_{5-6}$ cycloalkyl, $C_{5-6}$ heterocycloalkyl, $C_{5-6}$ aryl, substituted $C_{1-3}$ alkyl, substituted $C_{5-6}$ cycloalkyl, substituted $C_{5-6}$ heterocycloalkyl, and substituted $C_{5-6}$ aryl.

In compounds of Formula (1a)-(1b), $R^4$ can be selected from methyl, ethyl, phenyl, and benzyl.

In compounds of Formula (1a)-(1b), $R^4$ can be selected from hydrogen and $C_{1-8}$ alkyl.

In compounds of Formula (1a)-(1b), $R^4$ can be selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In compounds of Formula (1a)-(1b), $R^4$ can be selected from $C_{1-8}$ alkyl, $C_{1-8}$ heteroalkyl, $C_{7-9}$ arylalkyl, and $C_{5-7}$ heterocycloalkyl.

In compounds of Formula (1a)-(1b), $R^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In moieties of Formula (2) and compounds of Formula (1b), $R^3$ can be —C(O)—O—$R^4$; and $R^4$ can be selected from $C_{1-8}$ alkyl, $C_{1-3}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl, In moieties of Formula (2) and compounds of Formula (1b), $R^3$ can be —C(O)—O—$R^4$; and $R^4$ can be selected from $C_{1-8}$ alkyl, $C_{1-3}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In moieties of Formula (2) and compounds of Formula (1b), $R^3$ can be —C(O)—O—$R^4$; and $R^4$ can be selected from $C_{1-8}$ alkyl, $C_{1-3}$ heteroalkyl, $C_{7-9}$ arylalkyl, and $C_{5-7}$ heterocycloalkyl.

In moieties of Formula (2) and compounds of Formula (1b), $R^3$ can be selected from —O—C(O)—$CH_3$, —O—C(O)—$CH_2$—$CH_3$, —O—C(O)-phenyl, —O—C(O)—$CH_2$-phenyl, —S—C(O)—$CH_3$, —S—C(O)—$CH_2$—$CH_3$, —S—C(O)-phenyl, —S—C(O)—$CH_2$-phenyl, —NH—C(O)—$CH_3$, —NH—C(O)—$CH_2$—$CH_3$, —NH—C(O)-phenyl, —NH—C(O)—$CH_2$-phenyl, —O—C(O)—O—$CH_3$, —O—C(O)—O—$CH_2$—$CH_3$, —O—C(O)—O-phenyl, —O—C(O)—O—$CH_2$-phenyl, —S—C(O)—O—$CH_3$, —S—C(O)—O—$CH_2$—$CH_3$, —S—C(O)—O-phenyl, —S—C(O)—O—$CH_2$-phenyl, —NH—C(O)—O—$CH_3$, —NH—C(O)—O—$CH_2$—$CH_3$, —NH—C(O)—O-phenyl, —NH—C(O)—O—$CH_2$-phenyl, —C(O)—O—$CH_3$, —C(O)—O—$CH_2$—$CH_3$, —C(O)—O-phenyl, —C(O)—O—$CH_2$-phenyl, —C(O)—S—$CH_3$, —C(O)—S—$CH_2$—$CH_3$, —C(O)—S-phenyl, —C(O)—S—$CH_2$-phenyl, —C(O)—NH—$CH_3$, —C(O)—NH—$CH_2$—$CH_3$, —C(O)—NH-phenyl, —C(O)—NH—$CH_2$-phenyl, —O—C(O)—O—$CH_3$, —O—C(O)—O—$CH_2$—$CH_3$, —O—C(O)—O-phenyl, —O—C(O)—O—$CH_2$-phenyl, —O—C(O)—S—$CH_3$, —O—C(O)—S—$CH_2$—$CH_3$, —O—C(O)—S-phenyl, —O—C(O)—S—$CH_2$-phenyl, —O—C(O)—NH—$CH_3$, —O—C(O)—NH—$CH_2$—$CH_3$, —O—C(O)—NH-phenyl, —O—C(O)—NH—$CH_2$-phenyl, —S—SH, —S—S—$CH_3$, —S—S—$CH_2$—$CH_3$, —S—S-phenyl, —S—S—$CH_2$-phenyl, —SH, —S—$CH_3$, —S—$CH_2$—$CH_3$, —S-phenyl, —S—$CH_2$-phenyl, —$NH_2$, —NH—$CH_3$, —NH—$CH_2$—$CH_3$, —NH-phenyl, —NH—$CH_2$-phenyl, —CH(—$NH_2$)(—$CH_3$), —CH(—$NH_2$)(—$CH_2$—$CH_3$), —CH(—$NH_2$)(-phenyl), and —CH(—$NH_2$)(—$CH_2$-phenyl).

In moieties of Formula (2) and compounds of Formula (1b), $R^3$ can be selected from $C_{5-6}$ cycloalkyl, $C_{5-6}$ heterocycloalkyl, $C_{5-6}$ aryl, $C_{5-6}$ heteroaryl, substituted $C_{5-6}$ cycloalkyl, substituted $C_{5-6}$ heterocycloalkyl, and substituted $C_{5-6}$ aryl, and substituted $C_{5-6}$ heteroaryl, comprising at least one nucleophilic group. For example, $R^3$ can have the structure of Formula (3a) or Formula (3b):

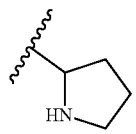

(3a)

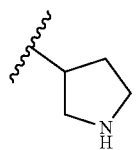

(3b)

In compounds of Formula (1a)-(1b), $R^4$ can be selected from $C_{1-3}$ alkyl, $C_{5-6}$ cycloalkyl, $C_{5-6}$ heterocycloalkyl, $C_{5-6}$ aryl, substituted $C_{1-3}$ alkyl, substituted $C_{5-6}$ cycloalkyl, substituted $C_{5-6}$ heterocycloalkyl, and substituted $C_{5-6}$ aryl.

In moieties of Formula (2) and compounds of Formula (1b), $R^3$ can be —O—C(O)—$R^4$, where $R^4$ is defined as for Formula (1), or each $R^4$ can be selected from hydrogen and $C_{1-8}$ alkyl.

In compounds of Formula (1a)-(1b), $R^3$ can be —O—C(O)—$R^4$ and $R^4$ can be selected from hydrogen, $C_{1-3}$ alkyl, $C_{5-6}$ cycloalkyl, $C_{5-6}$ heterocycloalkyl, $C_{5-6}$ aryl, substituted $C_{1-3}$ alkyl, substituted $C_{5-6}$ cycloalkyl, substituted $C_{5-6}$ heterocycloalkyl, and substituted $C_{5-6}$ aryl.

In compounds of Formula (1a)-(1b), $R^3$ can be —O—C(O)—$R^4$ and $R^4$ can be selected from methyl, ethyl, phenyl, and benzyl.

In compounds of Formula (1a)-(1b), $R^3$ can be —O—C(O)—$R^4$ and $R^4$ can be selected from hydrogen and $C_{1-8}$ alkyl.

In compounds of Formula (1a)-(1b), $R^3$ can be —O—C(O)—$R^4$ and $R^4$ can be selected from $C_{1-8}$ alkyl, $C_{1-3}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In compounds of Formula (1a)-(1b), $R^3$ can be —O—C(O)—$R^4$ and $R^4$ can be selected from $C_{1-8}$ alkyl, $C_{1-3}$ heteroalkyl, $C_{7-9}$ arylalkyl, and $C_{5-7}$ heterocycloalkyl.

In compounds of Formula (1a)-(1b), $R^3$ can be —O—C(O)—$R^4$ and $R^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In moieties of Formula (2) and compounds of Formula (1b), $R^3$ can be —O—C(O)—$R^4$; and $R^4$ can be selected from $C_{1-8}$ alkyl, $C_{1-3}$ heteroalkyl, $C_{5-7}$ cycloalkyl, $C_{5-7}$ heterocycloalkyl, $C_6$ aryl, $C_{7-9}$ arylalkyl, substituted $C_{1-8}$ alkyl, substituted $C_{1-8}$ heteroalkyl, substituted $C_{5-6}$ cycloalkyl, substituted $C_{5-6}$ heterocycloalkyl, substituted $C_6$ aryl, and $C_{7-9}$ arylalkyl.

In moieties of Formula (2) and compounds of Formula (1b), $R^3$ can be —O—C(O)—$R^4$; and $R^4$ can be selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In moieties of Formula (2) and compounds of Formula (1b), $R^3$ can be —O—C(O)—$R^4$; and $R^4$ can be selected from $C_{1-8}$ alkyl, $C_{1-8}$ heteroalkyl, $C_{7-9}$ arylalkyl, and $C_{5-7}$ heterocycloalkyl.

In moieties of Formula (2) and compounds of Formula (1a)-(1b), each $R^1$ together with the carbon atom to which each $R^1$ is bonded form a $C_{4-6}$ heterocycloalkyl ring comprising two adjacent S atoms or a substituted $C_{4-6}$ heterocycloalkyl ring comprising at least one heteroatom selected from O and S, and a =O substituent group bonded to a carbon atom adjacent the at least one heteroatom.

In moieties of Formula (2) and compounds of Formula (1b), $R^2$ can be a single bond; $R^3$ can be $C_{1-3}$ alkyl; and each $R^1$ together with the carbon atom to which each $R^1$ is bonded form a $C_{4-6}$ heterocycloalkyl ring comprising two adjacent S atoms or a substituted $C_{4-6}$ heterocycloalkyl ring comprising at least one heteroatom selected from O and S, and a =O substituent group bonded to a carbon atom adjacent the heteroatom.

In moieties of Formula (2) and compounds of Formula (1b), each $R^1$ together with the carbon atom to which they are bonded can from a $C_4$-, $C_5$-, or $C_6$-heterocycloalkyl group. The heterocycloalkyl group can have two adjacent sulfur atoms. In moieties of Formula (2) and compounds of Formula (1b), each $R^1$ together with the carbon atom to which they are bonded can from a $C_4$-, $C_5$-, or $C_6$-heterocycloalkyl group, $R^2$ can be a single bond and $R^3$ can be $C_{1-6}$ alkyl, such as $C_{1-4}$ alkyl, such as methyl or ethyl:

In moieties of Formula (2) and compounds of Formula (1b), each $R^1$ together with the carbon atom to which they are bonded can from a substituted $C_4$—, substituted $C_5$—, or substituted $C_6$-heterocycloalkyl group. The substituted heterocycloalkyl group can have a sulfur atom and an adjacent carbonyl (=O) group. The substituted heterocycloalkyl group can have am oxygen atom and an adjacent carbonyl (=O) group.

In moieties of Formula (2) and compounds of Formula (1b), each $R^1$ together with the carbon atom to which they are bonded can from a substituted $C_4$—, substituted $C_5$—, or substituted $C_6$-heterocycloalkyl group, $R^3$ can be a single bond and $R^4$ can be $C_{1-6}$ alkyl, such as $C_{1-4}$ alkyl, such as methyl or ethyl.

In moieties of Formula (2) and compounds of Formula (1b), $R^2$ can be a single bond; $R^3$ can be $C_{1-3}$ alkyl; and each $R^1$ together with the carbon atom to which each $R^1$ is bonded can form a $C_{4-6}$ heterocycloalkyl ring or a substituted $C_{4-6}$ heterocycloalkyl ring.

In moieties of Formula (2) and compounds of Formula (1b), $R^2$ can be a single bond; $R^3$ can be $C_{1-3}$ alkyl; and each $R^1$ together with the carbon atom to which each $R^1$ is bonded can form a $C_{4-6}$ heterocycloalkyl ring comprising two adjacent S atoms or a substituted $C_{4-6}$ heterocycloalkyl ring comprising at least one heteroatom selected from O and S, and a =O substituent group bonded to a carbon atom adjacent the heteroatom.

In moieties of Formula (2) and compounds of Formula (1b), $R^2$ can be a single bond; $R^3$ can be $C_{1-3}$ alkyl; and each $R^1$ together with the carbon atom to which each $R^1$ is bonded can form a 1,2-dithiolante ring, a 1,2-dithane ring, a thietan-2-one ring, a dihydrothiophen-2(3H)-one ring, a tetrahydro-2H-thipyran-2-one ring, an oxetan-2-one ring, a dihydrofuran-2(3H)-one ring, or a tetrahydro-2H-pyran-2-one ring.

In moieties of Formula (2) and compounds of Formula (1b), each $R^1$ can be methyl;

$R^2$ can be selected from a single bond, methanediyl, ethanediyl, —CH(—OH)—, —CH(—O—C(O)—CH$_2$CH$_3$)—, and 1,2-benzene-diyl; and $R^3$ can be selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$), where $R^4$ can be selected from hydrogen, methyl, ethyl, cyclopentyl, cyclohexyl, phenyl, benzyl, and 2-pyrrolidinyl.

In moieties of Formula (2) and compounds of Formula (1b), each $R^1$ and the geminal carbon to which each $R^1$ is bonded can form a $C_{3-6}$ cycloalkyl ring;

$R^2$ can be selected from a single bond, methanediyl, ethanediyl, —CH(—OH)—, —CH(—O—C(O)—CH$_2$CH$_3$)—, and 1,2-benzene-diyl; and $R^3$ can be selected from —O—C(O)—$R^4$, —C(O)—O—$R^4$, —S—C(O)—$R^4$, —C(O)—S—$R^4$, —S—S—$R^4$, —NHR$^4$, and —CH(—NH$_2$)(—$R^4$), where $R^4$ can be selected from hydrogen, methyl, ethyl, cyclopentyl, cyclohexyl, phenyl, benzyl, and 2-pyrrolidinyl.

In moieties of Formula (2) and compounds of Formula (1b), $R^2$ can be a single bond;

$R^3$ be $C_{1-3}$ alkyl; and each $R^1$ together with the carbon atom to which each $R^1$ is bonded can form a 1,2-dithiolante ring, a 1,2-dithane ring, a thietan-2-one ring, a dihydrothiophen-2(3H)-one ring, a tetrahydro-2H-thipyran-2-one ring, an oxetan-2-one ring, a dihydrofuran-2(3H)-one ring, or a tetrahydro-2H-pyran-2-one ring.

In moieties of Formula (2) and compounds of Formula (1b),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NH$R^4$, and —CH(—NH$_2$)(—$R^4$); wherein $R^4$ can be selected from $C_{1-8}$ alkyl, $C_{1-8}$ heteroalkyl, $C_{7-9}$ arylalkyl, and $C_{5-7}$ heterocycloalkyl.

In moieties of Formula (2) and compounds of Formula (1b),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be —C(O)—O—$R^4$; wherein $R^4$ can be selected from $C_{1-8}$ alkyl, $C_{1-8}$ heteroalkyl, $C_{7-9}$ arylalkyl, and $C_{5-7}$ heterocycloalkyl.

In moieties of Formula (2) and compounds of Formula (1b),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be selected from —O—C(O)—$R^4$, —C(O)—O—$R^4$, —S—C(O)—$R^4$, —C(O)—S—$R^4$, —S—S—$R^4$, —NH$R^4$, and —CH(—NH$_2$)(—$R^4$); wherein $R^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In moieties of Formula (2) and compounds of Formula (1b),
each $R^1$ can be methyl;
$R^2$ can be selected from a single bond, methanediyl, ethanediyl, —CH(—OH)—, —CH(—O—C(O)—CH$_2$CH$_3$)—, and 1,2-benzene-diyl; and
$R^3$ can be —C(O)—O—$R^4$; wherein $R^4$ can be selected from methyl, ethyl, n-propyl, isopropyl, n-butyl, sec-butyl isobutyl, tert-butyl, 2-methoxyethyl, methylbenzene, oxetane-3-oxy-yl, cyclopentyl, cyclohexyl, and 2-pyrrolidinyl.

In moieties of Formula (2) and compounds of Formula (1b),
each $R^1$ can be methyl;
$R^2$ can be a single bond; and
$R^3$ can be —C(O)—O—$R^4$;
wherein $R^4$ can be selected from $C_{1-10}$ alkyl, $C_{1-10}$ heteroalkyl, $C_{7-10}$ alkylarene, and $C_{5-10}$ heteroalkylcycloalkyl.

In moieties of Formula (2) and compounds of Formula (1b),
each $R^1$ can be methyl;
$R^2$ can be a single bond;
$R^3$ can be —C(O)—O—$R^4$; wherein $R^4$ can be selected from $C_{1-10}$ alkyl, $C_{1-10}$ heteroalkyl, $C_{7-10}$ alkylarene, and $C_{5-10}$ heteroalkylcycloalkyl; and
$R^7$ can be hydrogen.

In moieties of Formula (2) and compounds of Formula (1b), $R^7$ can be hydrogen.

In moieties of Formula (2) and compounds of Formula (1b), each $R^1$ can be independently $C_{1-3}$ alkyl; each $R^2$ can be a single bond; and $R^7$ can be hydrogen.

In moieties of Formula (2) and compounds of Formula (1b), each $R^1$ can be independently $C_{1-3}$ alkyl; and each $R^2$ can be a single bond.

In moieties of Formula (2) and compounds of Formula (1b),
each $R^1$ can be independently selected from $C_{1-3}$ alkyl, or each $R^1$ together with the geminal carbon atom to which they are bonded form a $C_{3-6}$ cycloalkyl ring, a substituted $C_{3-6}$ cycloalkyl ring, a $C_{3-6}$ heterocycloalkyl ring, or a substituted $C_{3-6}$ heterocycloalkyl ring;
$R^2$ can be a single bond;
$R^3$ can be —C(O)—O—$R^4$; and
$R^4$ can be selected from $C_{1-8}$ alkyl, $C_{1-8}$ heteroalkyl, $C_{7-9}$ arylalkyl, $C_{5-7}$ heterocycloalkyl, substituted $C_{1-8}$ alkyl, substituted $C_{1-8}$ heteroalkyl, substituted $C_{7-9}$ arylalkyl, and substituted $C_{5-7}$ heterocycloalkyl.

In moieties of Formula (2) and compounds of Formula (1b),
each $R^1$ can be independently selected from $C_{1-3}$ alkyl, or each $R^1$ together with the carbon atom to which they are bonded form a $C_{3-6}$ cycloalkyl ring;
$R^2$ can be selected from single bond, methane-diyl, and ethane-diyl; and
$R^3$ can be selected from —C(O)—O—$R^4$ and —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In moieties of Formula (2) and compounds of Formula (1b),
each $R^1$ can be independently selected from $C_{1-3}$ alkyl, or each $R^1$ together with the carbon atom to which they are bonded form a $C_{3-6}$ cycloalkyl ring;
$R^2$ can be a single bond; and
$R^3$ can be —C(O)—O—$R^4$, where $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In moieties of Formula (2) and compounds of Formula (1b),
each $R^1$ can be independently selected from $C_{1-3}$ alkyl, or each $R^1$ together with the carbon atom to which they are bonded form a $C_{3-6}$ cycloalkyl ring;
$R^2$ can be —(CH$_2$)$_2$—; and
$R^3$ can be —C(O)—O—$R^4$ wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In moieties of Formula (2) and compounds of Formula (1b),
each $R^1$ can be selected from $C_{1-3}$ alkyl, or each $R^1$ together with the carbon atom to which they are bonded form a $C_{3-6}$ cycloalkyl ring;
$R^2$ can be —CH$_2$—; and
$R^3$ can be —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In moieties of Formula (2) and compounds of Formula (1b),
each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;
$R^2$ can be a single bond; and
$R^3$ can be $C_{1-3}$ alkyl.

In moieties of Formula (2) and compounds of Formula (1b),
each $R^1$ can be independently selected from $C_{1-3}$ alkyl;
$R^2$ can be selected from a single bond and methanediyl; and R$^3$ can be selected from —O—C(O)—R$^4$ and —C(O)—O—R$^4$, wherein R$^4$ can be selected from C$_{1-10}$ alkyl and substituted phenyl.

In moieties of Formula (2) and compounds of Formula (1b),
each R$^1$ can be independently selected from C$_{1-3}$ alkyl;
R$^2$ can be a single bond;
R$^3$ can be —CH=C(R$^9$)$_2$, wherein each R$^9$ can be —C(O)—O—R$^1$, or each R$^9$ together with the carbon atom to which they are bonded from a substituted heterocyclohexyl ring; and
each R$^1$ can be C$_{1-4}$ alkyl.

In moieties of Formula (2) and compounds of Formula (1b),
each R$^1$ can be independently selected from C$_{1-3}$ alkyl;
R$^2$ can be selected from a single bond and methanediyl; and
R$^3$ can be substituted phenyl, wherein the one or more substituents can be independently selected from —CH$_2$—O—C(O)—R$^4$ and —O—C(O)—R$^4$, wherein R$^4$ can be selected from C$_{1-10}$ alkyl and phenyl.

In moieties of Formula (2) and compounds of Formula (1b),
each R$^1$ can be independently selected from C$_{1-3}$ alkyl;
R$^2$ can be selected from —C(R$^9$)$_2$— and —CH$_2$—C(R$^9$)$_2$—, wherein each R$^9$ can be independently selected from C$_{1-3}$ alkyl; and
R$^3$ can be selected from —C(O)—O—R$^4$ and —O—C(O)—R$^4$, wherein R$^4$ can be selected from C$_{1-10}$ alkyl, C$_{1-10}$ heteroalkyl, substituted C$_{1-10}$ alkyl, substituted C$_{1-10}$ heteroalkyl, and 4(yl-methyl)-5-methyl-1,3-dioxol-2-one.

In moieties of Formula (2) and compounds of Formula (1b),
each R$^1$ together with the carbon atom to which they are bonded form a substituted C$_{5-6}$ heterocyclic ring;
R$^2$ can be a single bond; and
R$^3$ can be C$_{1-3}$ alkyl.

In moieties of Formula (2) and compounds of Formula (1b),
R$^7$ can be selected from hydrogen, C$_{1-6}$ alkyl, C$_{1-6}$ heteroalkyl, and 4-(yl-methyl)-5-methyl-1,3-dioxol-2-one;
each R$^1$ can be independently selected from C$_{1-3}$ alkyl;
R$^2$ can be a single bond; and
R$^3$ can be —C(O)—O—R$^4$, where R$^4$ can be selected from C$_{1-6}$ alkyl.

A compound of Formula (1b) can be a compound of sub-genus (1A), or a pharmaceutically acceptable salt thereof, wherein,
R$^7$ can be selected from hydrogen, C$_{1-6}$ alkyl, C$_{1-6}$ heteroalkyl, and 4-(yl-methyl)-5-methyl-1,3-dioxol-2-one;
each R$^1$ can be independently selected from C$_{1-3}$ alkyl, or each R$^1$ together with the carbon atom to which they are bonded form a C$_{3-6}$ cycloalkyl ring;
R$^2$ can be selected from single bond, methane-diyl, and ethane-diyl; and
R$^3$ can be selected from —C(O)—O—R$^4$ and —S—C(O)—R$^4$, wherein R$^4$ can be selected from C$_{1-10}$ alkyl, C$_{1-10}$ heteroalkyl, C$_{5-10}$ arylalkyl, C$_{3-6}$ heterocycloalkyl, and substituted C$_{4-10}$ heterocycloalkylalkyl.

In compounds of subgenus (1A), R$^7$ can be hydrogen.
In compounds of subgenus (1A), R$^7$ can be selected from C$_{1-6}$ alkyl and C$_{1-6}$ heteroalkyl.
In compounds of subgenus (1A), each R$^1$ can be independently selected from C$_{1-3}$ alkyl.
In compounds of subgenus (1A), each R$^1$ together with the carbon atom to which they are bonded form a C$_{3-6}$ cycloalkyl ring.

In compounds of subgenus (1A), R$^2$ can be a single bond.
In compounds of subgenus (1A), R$^2$ can be methane-diyl.
In compounds of subgenus (1A), R$^2$ can be ethane-diyl.
In compounds of subgenus (1A), R$^3$ can be —C(O)—O—R$^4$.
In compounds of subgenus (1A), R$^3$ can be —S—C(O)—R$^4$.
In compounds of subgenus (1A), R$^4$ can be C$_{1-10}$ alkyl.
In compounds of subgenus (1A), R$^4$ can be C$_{1-10}$ heteroalkyl.
In compounds of subgenus (1A), R$^4$ can be C$_{5-10}$ arylalkyl.
In compounds of subgenus (1A), R$^4$ can be C$_{3-6}$ heterocycloalkyl.
In compounds of subgenus (1A), R$^4$ can be substituted C$_{4-10}$ heterocycloalkylalkyl.

A compound of Formula (1b) can be a compound of sub-genus (1B), or a pharmaceutically acceptable salt thereof, wherein,
R$^7$ can be selected from hydrogen, C$_{1-6}$ alkyl, C$_{1-6}$ heteroalkyl, and 4-(yl-methyl)-5-methyl-1,3-dioxol-2-one;
each R$^1$ can be independently selected from C$_{1-3}$ alkyl, or each R$^1$ together with the carbon atom to which they are bonded form a C$_{3-6}$ cycloalkyl ring;
R$^2$ can be a single bond; and
R$^3$ can be —C(O)—O—R$^4$, where R$^4$ can be selected from C$_{1-10}$ alkyl, C$_{1-10}$ heteroalkyl, C$_{5-10}$ arylalkyl, C$_{3-6}$ heterocycloalkyl, and substituted C$_{4-10}$ heterocycloalkylalkyl.

In compounds of subgenus (1B), R$^7$ can be hydrogen.
In compounds of subgenus (1B), R$^7$ can be selected from C$_{1-6}$ alkyl and C$_{1-6}$ heteroalkyl.
In compounds of subgenus (1B), each R$^1$ can be independently selected from C$_{1-3}$ alkyl.
In compounds of subgenus (1B), each R$^1$ together with the carbon atom to which they are bonded form a C$_{3-6}$ cycloalkyl ring.
In compounds of subgenus (1B), R$^4$ can be selected from C$_{1-7}$ alkyl, C$_{1-10}$ heteroalkyl wherein the one or more heteroatoms can be oxygen, —CH$_2$—C$_{4-6}$ cycloalkyl, —(CH$_2$)$_2$—C$_{4-6}$ cycloalkyl, C$_{3-6}$ heterocycloalkyl wherein the one or more heteroatoms can be oxygen, and —CH$_2$—C$_{3-6}$ substituted heterocycloalkyl, and —(CH$_2$)$_2$—C$_{3-6}$ substituted heterocycloalkyl.

In compounds of subgenus (1B), in the substituted C$_{3-6}$ heterocycloalkyl the one or more heteroatoms can be oxygen, and the one or more substituents can be independently selected from C$_{1-3}$ alkyl and =O.
In compounds of subgenus (1B), each R$^1$ can be methyl, or each R$^1$ together with the carbon atom to which they are bonded form a cyclohexyl ring or a cyclopentyl ring.
In compounds of subgenus (1B), R$^4$ can be selected from methyl, ethyl, n-propyl, iso-propyl, n-butyl, n-hexyl, n-heptyl, —CH$_2$—CH$_2$—O—CH$_3$, benzyl, 3-oxetanyl, and methyl-5-methyl-1,3-dioxol-2-one.

In compounds of subgenus (1B), R$^7$ can be selected from hydrogen, C$_{1-6}$ alkyl, C$_{1-6}$ heteroalkyl, and 4-(yl-methyl)-5-methyl-1,3-dioxol-2-one;
each R$^1$ can be methyl, or each R$^1$ together with the carbon atom to which they are bonded form a cyclohexyl ring or a cyclopentyl ring;
R$^2$ can be a single bond; and
R$^3$ can be —C(O)—O—R$^4$, wherein R$^4$ can be selected from methyl, ethyl, n-propyl, iso-propyl, n-butyl, n-hexyl, n-heptyl, —CH$_2$—CH$_2$—O—CH$_3$, —CH$_2$-phenyl (benzyl), 3-oxetanyl, and methyl-5-methyl-1,3-dioxol-2-one.

A compound of Formula (1b) can be a compound of sub-genus (1C), or a pharmaceutically acceptable salt thereof, wherein, $R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl, or each $R^1$ together with the carbon atom to which they are bonded form a $C_{3-6}$ cycloalkyl ring;

$R^2$ can be —$(CH_2)_2$—; and $R^3$ can be —C(O)—O—$R^4$ wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of subgenus (1C), $R^7$ can be hydrogen.

In compounds of subgenus (1C), $R^7$ can be selected from $C_{1-6}$ alkyl and $C_{1-6}$ heteroalkyl.

In compounds of subgenus (1C), each $R^1$ can be independently selected from $C_{1-3}$ alkyl.

In compounds of subgenus (1C), each $R^1$ together with the carbon atom to which they are bonded form a $C_{3-6}$ cycloalkyl ring.

In compounds of subgenus (1C), $R^4$ can be selected from $C_{1-7}$ alkyl, $C_{1-10}$ heteroalkyl wherein the one or more heteroatoms can be oxygen, —$CH_2$—$C_{4-6}$ cycloalkyl, —$(CH_2)_2$—$C_{4-6}$ cycloalkyl, $C_{3-6}$ heterocycloalkyl wherein the one or more heteroatoms can be oxygen, —$CH_2$—$C_{3-6}$ substituted heterocycloalkyl, and —$(CH_2)_2$—$C_{3-6}$ substituted heterocycloalkyl.

In compounds of subgenus (1C), in the substituted $C_{3-6}$ heterocycloalkyl the one or more heteroatoms can be oxygen, and the one or more substituents can be independently selected from $C_{1-3}$ alkyl and =O.

In compounds of subgenus (1C), $R^4$ can be $C_{1-10}$ alkyl.

In compounds of subgenus (1C), $R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be methyl;

$R^2$ can be —$(CH_2)_2$—; and $R^3$ can be —C(O)—O—$R^4$ wherein $R^4$ can be selected from n-hexyl and n-heptyl.

A compound of Formula (1b) can be a compound of sub-genus (1D), or a pharmaceutically acceptable salt thereof, wherein, $R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be selected from $C_{1-3}$ alkyl, or each $R^1$ together with the carbon atom to which they are bonded form a $C_{3-6}$ cycloalkyl ring;

$R^2$ can be —$CH_2$—; and $R^3$ can be —S—C(O)—$R^4$, wherein $R^4$ can be selected from $C_{1-10}$ alkyl, $C_{1-10}$ heteroalkyl, $C_{5-10}$ arylalkyl, $C_{3-6}$ heterocycloalkyl, and substituted $C_{4-10}$ heterocycloalkylalkyl.

In compounds of subgenus (1D), $R^7$ can be hydrogen.

In compounds of subgenus (1D), $R^7$ can be selected from $C_{1-6}$ alkyl and $C_{1-6}$ heteroalkyl.

In compounds of subgenus (1D), each $R^1$ can be independently selected from $C_{1-3}$ alkyl.

In compounds of subgenus (1D), each $R^1$ together with the carbon atom to which they are bonded form a $C_{3-6}$ cycloalkyl ring.

In compounds of subgenus (1D), $R^4$ can be selected from $C_{1-7}$ alkyl, $C_{1-10}$ heteroalkyl wherein the one or more heteroatoms can be oxygen, —$CH_2$—$C_{4-6}$ cycloalkyl, —$(CH_2)_2$—$C_{4-6}$ cycloalkyl, $C_{3-6}$ heterocycloalkyl wherein the one or more heteroatoms can be oxygen, —$CH_2$—$C_{3-6}$ substituted heterocycloalkyl, and —$(CH_2)_2$—$C_{3-6}$ substituted heterocycloalkyl.

In compounds of subgenus (1D), in the substituted $C_{3-6}$ heterocycloalkyl the one or more heteroatoms can be oxygen, and the one or more substituents can be independently selected from $C_{1-3}$ alkyl and =O.

In compounds of subgenus (1D), $R^4$ can be $C_{1-10}$ alkyl.

In compounds of subgenus (1D), $R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be methyl;

$R^2$ can be —$CH_2$—; and $R^3$ can be —S—C(O)—$R^4$, wherein $R^4$ can be methyl.

A compound of Formula (1b) can be a compound of sub-genus (IE), or a pharmaceutically acceptable salt thereof, wherein, $R^7$ can be hydrogen;

each $R^1$ together with the carbon atom to which they are bonded form a $C_{3-6}$ cycloalkyl ring, a $C_{3-6}$ heterocycloalkyl ring, a $C_{3-6}$ cycloalkyl ring, or a $C_{3-6}$ heterocycloalkyl ring;

$R^2$ can be a single bond; and $R^3$ can be $C_{1-3}$ alkyl.

In compounds of subgenus (IE), $R^7$ can be hydrogen.

In compounds of subgenus (IE), $R^7$ can be selected from $C_{1-6}$ alkyl and $C_{1-6}$ heteroalkyl.

In compounds of subgenus (IE), each $R^1$ together with the carbon atom to which they are bonded form a $C_{3-6}$ heterocycloalkyl ring or a $C_{3-6}$ heterocycloalkyl ring;

In compounds of subgenus (IE), the one or more heteroatoms can be oxygen and the one or more substituents can be =O.

In compounds of subgenus (IE), each $R^1$ together with the carbon atom to which they are bonded form a dihydrofuran-2(3H)-one ring;

$R^2$ can be a single bond; and $R^3$ can be methyl.

A compound of Formula (1b) can be a compound of sub-genus (1F), or a pharmaceutically acceptable salt thereof, wherein, $R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl;

$R^2$ can be selected from a single bond and methanediyl; and $R^3$ can be selected from —O—C(O)—$R^4$ and —C(O)—O—$R^4$, wherein $R^4$ can be selected from $C_{1-10}$ alkyl and substituted phenyl.

In compounds of subgenus (1F), $R^7$ can be hydrogen.

In compounds of subgenus (1F), $R^7$ can be selected from $C_{1-6}$ alkyl and $C_{1-6}$ heteroalkyl.

In compounds of subgenus (1F), $R^2$ can be a single bond.

In compounds of subgenus (1F), $R^2$ can be methanediyl.

In compounds of subgenus (1F), $R^3$ can be —O—C(O)—$R^4$.

In compounds of subgenus (1F), $R^2$ can be methanediyl; and $R^3$ can be —O—C(O)—$R^4$.

In compounds of subgenus (1F), $R^3$ can be —C(O)—O—$R^4$.

In compounds of subgenus (1F), $R^2$ can be a single bond; and $R^3$ can be —C(O)—O—$R^4$.

In compounds of subgenus (1F), $R^2$ can be a single bond; $R^3$ can be —C(O)—O—$R^4$; and $R^4$ can be $C_{1-3}$ alkyl.

In compounds of subgenus (1F), $R^4$ can be $C_{1-10}$ alkyl.

In compounds of subgenus (1F), $R^4$ can be $C_{1-4}$ alkyl.

In compounds of subgenus (1F), $R^4$ can be substituted phenyl.

In compounds of subgenus (1F), $R^2$ can be methanediyl; $R^3$ can be —O—C(O)—$R^4$; and $R^4$ can be substituted phenyl.

In compounds of subgenus (1F), the one or more substituents can be independently selected from halogen, $C_{1-3}$ alkyl, and $C_{1-3}$ alkoxy.

In compounds of subgenus (1F), the substituted phenyl can be 2,6-substituted phenyl.

In compounds of subgenus (1F), each of the substituents can be selected from $C_{1-3}$ alkyl and $C_{1-3}$ alkoxy.

In compounds of subgenus (1F), the substituted phenyl can be 2,5,6-substituted phenyl.

In compounds of subgenus (1F), each of the substituents at the 2 and 6 positions can be independently selected from $C_{1-3}$ alkyl and $C_{1-3}$ alkoxy; and the substituent at the 5 position can be halogen.

A compound of Formula (1b) can be a compound of sub-genus (1G), or a pharmaceutically acceptable salt thereof, wherein, $R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl;

$R^2$ can be a single bond; and $R^3$ can be —CH=C($R^9$)$_2$, wherein each $R^9$ can be —C(O)—O—$R^1$, or each $R^9$ together with the carbon atom to which they are bonded from a substituted heterocyclohexyl ring; and each $R^1$ can be $C_{1-4}$ alkyl.

In compounds of subgenus (1G), $R^7$ can be hydrogen.

In compounds of subgenus (1G), $R^7$ can be selected from $C_{1-6}$ alkyl and $C_{1-6}$ heteroalkyl.

In compounds of subgenus (1G), each $R^4$ can be —C(O)—O—$R^1$.

In compounds of subgenus (1G), each $R^4$ can be —C(O)—O—R, or each $R^4$ together with the carbon atom to which they are bonded from a substituted heterocyclohexyl ring.

In compounds of subgenus (1G), in the substituted heterocyclohexyl ring, the one or more heteroatoms can be oxygen.

In compounds of subgenus (1G), in the substituted heterocyclohexyl ring, the one or more substituents can be independently selected from $C_{1-3}$ alkyl and =O.

In compounds of subgenus (1G), the substituted heterocycloalkyl ring can be 2,2-dimethyl-5-yl-1,3-dioxane-4,6-dione.

A compound of Formula (1b) can be a compound of sub-genus (1H), or a pharmaceutically acceptable salt thereof, wherein, $R^7$ can be selected from hydrogen, $C_{1-6}$ alkyl, $C_{1-6}$ heteroalkyl, and 4-(yl-methyl)-5-methyl-1,3-dioxol-2-one;

$R^7$ can be hydrogen;

each $R^1$ can be independently selected from $C_{1-3}$ alkyl;

$R^2$ can be selected from a single bond and methanediyl; and $R^3$ can be substituted phenyl, wherein the one or more substituents can be independently selected from —CH$_2$—O—C(O)—$R^4$ and —O—C(O)—$R^4$, wherein $R^4$ can be selected from $C_{1-10}$ alkyl and phenyl.

In compounds of subgenus (1H), $R^7$ can be hydrogen.

In compounds of subgenus (1H), $R^7$ can be selected from $C_{1-6}$ alkyl and $C_{1-6}$ heteroalkyl.

In compounds of subgenus (1H), $R^2$ can be a single bond.

In compounds of subgenus (1H), $R^2$ can be 2-substituted phenyl.

In compounds of subgenus (1H), the one or more substituents can be —CH$_2$—O—C(O)—$R^4$.

In compounds of subgenus (1H), the one or more substituents can be —O—C(O)—$R^4$.

In compounds of subgenus (1H), $R^4$ can be $C_{1-10}$ alkyl.

In compounds of subgenus (1H), $R^4$ can be selected from methyl, ethyl, iso-propyl, pivalolyl, and phenyl.

A compound of Formula (1b) can be a compound of sub-genus (11), or a pharmaceutically acceptable salt thereof, wherein, $R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl;

$R^2$ can be selected from —C($R^9$)$_2$— and —CH$_2$—C($R^9$)$_2$—, wherein each $R^9$ can be independently selected from $C_{1-3}$ alkyl; and $R^3$ can be selected from —C(O)—O—$R^4$ and —O—C(O)—$R^4$, wherein $R^4$ can be selected from $C_{1-10}$ alkyl, $C_{1-10}$ heteroalkyl, substituted $C_{1-10}$ alkyl, substituted $C_{1-10}$ heteroalkyl, and 4(yl-methyl)-5-methyl-1,3-dioxol-2-one.

In compounds of subgenus (11), $R^7$ can be hydrogen.

In compounds of subgenus (11), $R^7$ can be selected from $C_{1-6}$ alkyl and $C_{1-6}$ heteroalkyl.

In compounds of subgenus (11), each $R^1$ can be methyl.

In compounds of subgenus (11), $R^2$ can be —C($R^9$)$_2$—.

In compounds of subgenus (11), $R^2$ can be —CH$_2$—C(R)$_2$—.

In compounds of subgenus (11), each $R^9$ can be methyl.

In compounds of subgenus (11), each $R^1$ can be methyl; and each $R^9$ can be methyl.

In compounds of subgenus (11), $R^3$ can be —C(O)—O—$R^4$.

In compounds of subgenus (11), $R^3$ can be —O—C(O)—$R^4$.

A compound of Formula (1b) can be a compound of sub-genus (1J), or a pharmaceutically acceptable salt thereof, wherein, $R^7$ can be selected from hydrogen, $C_{1-6}$ alkyl, $C_{1-6}$ heteroalkyl, and 4-(yl-methyl)-5-methyl-1,3-dioxol-2-one;

each $R^1$ together with the carbon atom to which they are bonded form a substituted $C_{5-6}$ heterocyclic ring;

$R^2$ can be a single bond; and $R^3$ can be $C_{1-3}$ alkyl.

In compounds of subgenus (1J), in the substituted $C_{5-6}$ heterocyclic ring, the one or more heteroatoms can be oxygen; and the one or more substituents can be independently selected from $C_{1-3}$ alkyl and =O.

In compounds of subgenus (1J), each $R^1$ together with the carbon atom to which they are bonded form a tetrahydro-2H-pyran-2-one ring.

In compounds of subgenus (1J), $R^7$ can be selected from hydrogen, $C_{1-6}$ alkyl, $C_{1-6}$ heteroalkyl, and 4-(yl-methyl)-5-methyl-1,3-dioxol-2-one;

each $R^1$ can be independently selected from $C_{1-3}$ alkyl;

$R^2$ can be selected from $C_{2-4}$ alkanediyl; and $R^3$ can be substituted $C_{5-6}$ heterocycloalkyl, wherein the one or more heteroatoms can be independently selected from N and O; and the one or more substituents can be independently selected from $C_{1-3}$ alkyl and =O.

In compounds of subgenus (1J), $R^7$ can be hydrogen.

In compounds of subgenus (1J), $R^7$ can be selected from $C_{1-6}$ alky, and $C_{1-6}$ heteroalkyl.

In compounds of subgenus (1J), $R^3$ can have the structure of Formula (4):

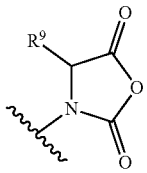

(4)

wherein $R^9$ can be selected from hydrogen, $C_{1-6}$ alkyl, $C_{4-6}$ cycloalkyl, $C_{1-6}$ heteroalkyl, $C_{4-6}$ heterocycloalkyl, substituted $C_{1-6}$ alkyl, substituted $C_{4-6}$ cycloalkyl, substituted $C_{1-6}$ heteroalkyl, and substituted $C_{4-6}$ heterocycloalkyl.

In compounds of subgenus (1J), $R^9$ can be selected from hydrogen and $C_{1-6}$ alkyl such as $C_{1-4}$ alkyl such as methyl or ethyl.

A compound of Formula (1a) can have the structure of Formula (1c):

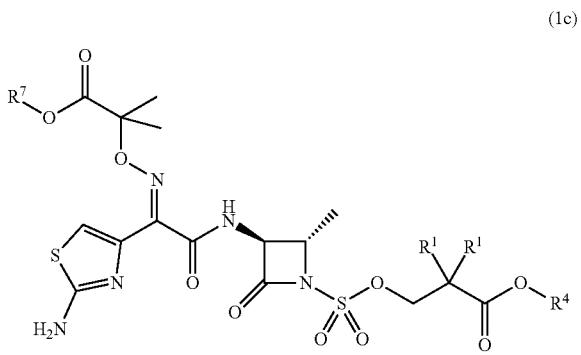

(1c)

wherein each $R^1$, $R^4$, and $R^7$ is defined as for Formula (1a).

In compounds of Formula (1c),
each $R^1$ can be selected from $C_{1-6}$ alkyl;
$R^4$ can be selected from $C_{1-6}$ alkyl, $C_{1-6}$ heteroalkyl, $C_{5-6}$ cycloalkyl, and $C_{5-6}$ heterocycloalkyl; and
$R^7$ can be selected from hydrogen, $C_{1-6}$ alkyl, $C_{1-6}$ heteroalkyl, and 4-(yl-methyl)-5-methyl-1,3-dioxol-2-one.

In compounds of Formula (1c), each $R^1$ can be selected from $C_{1-3}$ alkyl; $R^4$ can be selected from $C_{1-6}$ alkyl and $C_{5-6}$ cycloalkyl; and $R^7$ can be selected from hydrogen and $C_{1-6}$ alkyl.

In compounds of Formula (1a)-(1b), the compound can be selected from:
2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-ethoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((2,2-dimethyl-3-oxo-3-propoxypropoxy)sulfonyl)-2-methyl-4-oxoazetidin-3-yl)amino)-2-oxoethylidene)amino)oxy)-2-methylpropanoic acid;
methyl 3-(((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;
ethyl 3-(((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;
propyl 3-(((((2S,3S)-3-((E)-2-(2-aminothiazol-4-yl)-2-(((1-methoxy-2-methyl-1-oxopropan-2-yl)oxy)imino)acetamido)-2-methyl-4-oxoazetidin-1-yl)sulfonyl)oxy)-2,2-dimethylpropanoate;
methyl 3-(((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;
ethyl 3-(((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;
propyl 3-(((((2S,3S)-3-((E)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate;
methyl 3-(((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;
ethyl 3-(((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;
propyl 3-(((((2S,3S)-3-((E)-2-(2-aminothiazol-4-yl)-2-(((1-(tert-butoxy)-2-methyl-1-oxopropan-2-yl)oxy)imino)acetamido)-2-methyl-4-oxoazetidin-1-yl)sulfonyl)oxy)-2,2-dimethylpropanoate;
a pharmaceutically acceptable salt of any of the foregoing; and
a combination of any of the foregoing.

In compounds of Formula (1a)-(1b), the compound can be selected from:
2-((((E)-1-(2-aminothiazol-4-yl)-2-(((2S,3S)-1-((3-(benzoyloxy)-2,2-dimethylpropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-methoxy-2,2-dimethyl-3-oxopropoxy)sulfonyl)-2-methyl-4-oxoazetidin-3-yl)amino)-2-oxoethylidene) amino)oxy)-2-methylpropanoic acid;
2-((((E)-1-(2-aminothiazol-4-yl)-2-(((2S,3S)-1-((3-ethoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((4-(benzoyloxy)-2,2-dimethylbutoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((2,2-dimethyl-4-(propionyloxy)butoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((4-((6-(benzyloxy)-6-oxohexanoyl)oxy)-2,2-dimethylbutoxy)sulfonyl)-2-methyl-4-oxoazetidin-3-yl)amino)-2-oxoethylidene)amino)oxy)-2-methylpropanoic acid;
6-(4-(((((2S,3S)-3-((E)-2-(2-aminothiazol-4-yl)-2-(((2-carboxypropan-2-yl)oxy)imino)acetamido)-2-methyl-4-oxoazetidin-1-yl)sulfonyl)oxy)-3,3-dimethylbutoxy)-6-oxohexanoic acid;
2-((((E)-1-(2-aminothiazol-4-yl)-2-(((2S,3S)-1-((3-methoxy-2,2-dimethyl-3-oxopropoxy)sulfonyl)-2- methyl-4-oxoazetidin-3-yl)amino)-2-oxoethylidene)
amino)oxy)-2-methylpropanoic acid;
2-((((E)-1-(2-aminothiazol-4-yl)-2-(((2S,3S)-1-((3-isopropoxy-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(hexyloxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(heptyloxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(tert-butoxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((3-(2-methoxyethoxy)-2,2-dimethyl-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-((2,2-dimethyl-3-(oxetan-3-yloxy)-3-oxopropoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-(((1-(ethoxycarbonyl)cyclohexyl)methoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-(((1-(ethoxycarbonyl)cyclopentyl)methoxy)sulfonyl)-2-methyl-4-oxoazetidin-3-yl)amino)-2-oxoethylidene)amino)oxy)-2-methylpropanoic acid;
2-((((E)-1-(2-aminothiazol-4-yl)-2-(((2S,3S)-1-(((1-(ethoxycarbonyl)cyclobutyl)methoxy)sulfonyl)-2-methyl-4-oxoazetidin-3-yl)amino)-2-oxoethylidene)amino)oxy)-2-methylpropanoic acid;
a pharmaceutically acceptable salt of any of the foregoing; and
a combination of any of the foregoing.

A compound of Formula (1a) can have the structure of Formula (1d):

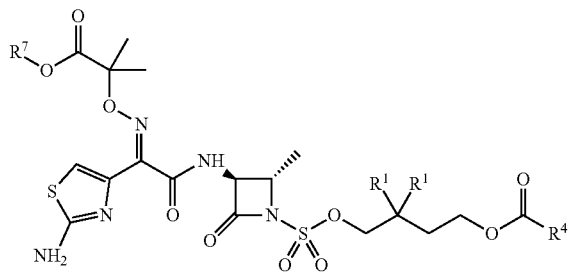

(1d)

wherein each $R^1$, $R^4$, and $R^7$ is defined as for Formula (1a).

In compounds of Formula (1d),
each $R^1$ can be selected from $C_{1-6}$ alkyl;
$R^4$ can be selected from $C_{1-6}$ alkyl, $C_{1-6}$ heteroalkyl, $C_{5-6}$ cycloalkyl, and $C_{5-6}$ heterocycloalkyl; and
$R^7$ can be selected from hydrogen, $C_{1-6}$ alkyl, $C_{1-6}$ heteroalkyl, and 4-(yl-methyl)-5-methyl-1,3-dioxol-2-one.

In compounds of Formula (1d),
each $R^1$ can be selected from $C_{1-6}$ alkyl;
$R^4$ can be selected from $C_{1-6}$ alkyl, $C_{1-6}$ heteroalkyl, $C_{5-6}$ cycloalkyl, and $C_{5-6}$ heterocycloalkyl; and
$R^7$ can be hydrogen.

In compounds of Formula (1d),
each $R^1$ can be methyl;
$R^4$ can be selected from $C_{1-6}$ alkyl, $C_{1-6}$ heteroalkyl, $C_{5-6}$ cycloalkyl, and $C_{5-6}$ heterocycloalkyl; and
$R^7$ can be hydrogen.

In compounds of Formula (1d),
each $R^1$ can be methyl;
$R^4$ can be selected from $C_{1-6}$ alkyl and $C_{1-6}$ heteroalkyl; and
$R^7$ can be hydrogen.

In compounds of Formula (1d),
each $R^1$ can be methyl;
$R^4$ can be selected from $C_{1-6}$ alkyl; and
$R^7$ can be hydrogen.

In compounds of Formula (1d),
each $R^1$ can be methyl;
$R^4$ can be selected from methyl, ethyl, n-propyl, iso-propyl, and tert-butyl.
$R^7$ can be hydrogen.

A compound of Formula (1d) can be 2-((((E)-2-(((2S,3S)-1-((4-acetoxy-2,2-dimethylbutoxy)sulfonyl)-2-methyl-4-oxoazetidin-3-yl)amino)-1-(2-aminothiazol-4-yl)-2-oxoethylidene)amino)oxy)-2-methylpropanoic acid:

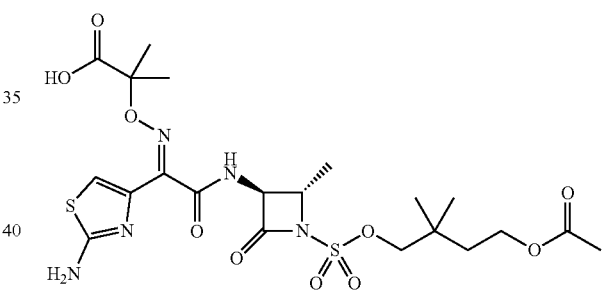

A compound of Formula (1d) can be 2-((((E)-1-(2-aminothiazol-4-yl)-2-(((2S,3S)-1-((2,2-dimethyl-4-(propionyloxy)butoxy)sulfonyl)-2-methyl-4-oxoazetidin-3-yl)amino)-2-oxoethylidene)amino)oxy)-2-methylpropanoic acid:

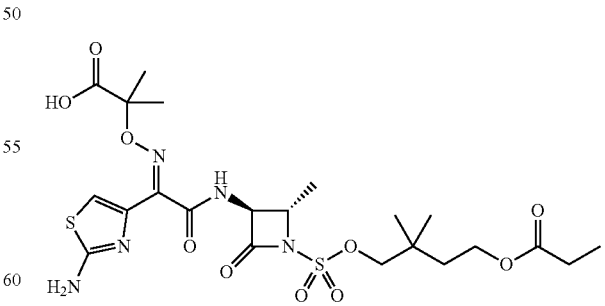

A compound of Formula (1d) can be 2-((((E)-1-(2-aminothiazol-4-yl)-2-(((2S,3S)-1-((2,2-dimethyl-4-(pivaloyloxy)butoxy)sulfonyl)-2-methyl-4-oxoazetidin-3-yl)amino)-2-oxoethylidene)amino)oxy)-2-methylpropanoic acid:

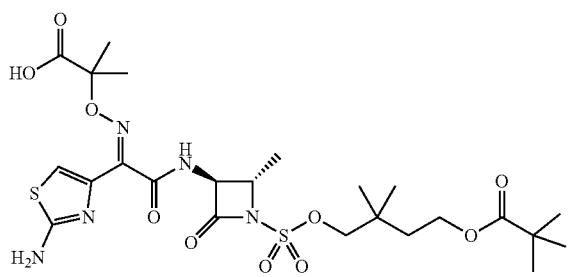 [SMILES: C[C@H]1[C@H](NC(=O)/C(=N/OC(C)(C)C(=O)O)c2csc(N)n2)C(=O)N1S(=O)(=O)OCC(C)(C)CCOC(=O)C(C)(C)C]

A compound of Formula (d) can be 2-((((E)-1-(2-aminothiazol-4-yl)-2-(((2S,3S)-1-((4-(isobutyryloxy)-2,2-dimethylbutoxy)sulfonyl)-2-methyl-4-oxoazetidin-3-yl)amino)-2-oxoethylidene)amino)oxy)-2-methylpropanoic acid:

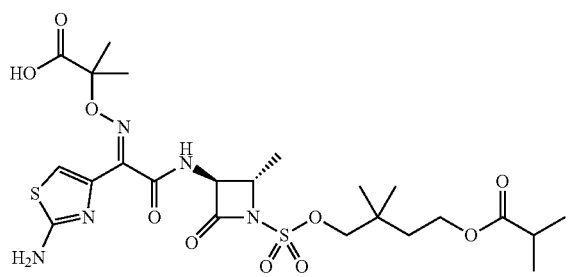

A compound of Formula (d) can be 2-((((E)-1-(2-aminothiazol-4-yl)-2-(((2S,3S)-1-((4-(butyryloxy)-2,2-dimethylbutoxy)sulfonyl)-2-methyl-4-oxoazetidin-3-yl)amino)-2-oxoethylidene)amino)oxy)-2-methylpropanoic acid:

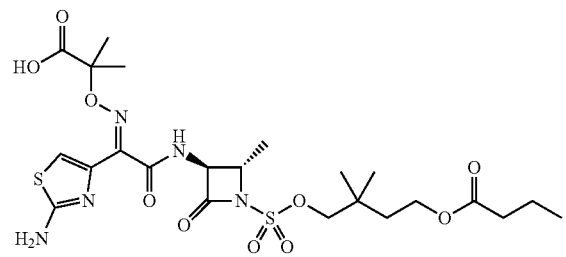 [SMILES: CCCC(=O)OCCC(C)(C)COS(=O)(=O)N1C(=O)[C@@H](NC(=O)/C(=N/OC(C)(C)C(=O)O)c2csc(N)n2)[C@@H]1C]

A compound of Formula (1a)-(1d) can be a solvate, a pharmaceutically acceptable salt, or a combination thereof.

In compounds of Formula (1a)-(1d), a pharmaceutically acceptable salt can be the hydrochloride salt.

In compounds of Formula (1a)-(1d), a pharmaceutically acceptable salt can be the dihydrochloride salt.

A compound of Formula (1a)-(1d) can be a pharmaceutically acceptable salt of a compound of Formula (1a)-(1d), a hydrate thereof, or a solvate of any of the foregoing.

Aztreonam derivatives of Formula (1a)-(1d) can be synthesized by the following methods.

An example of a pathway for synthesizing aztreonam derivatives of Formula (1a)-(1d) is shown in FIG. 1.

Referring to FIG. 1, starting with Boc-L-threonine, reacting with benzyl bromide provides Boc-O-benzyl threonine 1. Treatment of Boc-O-benzyl threonine 1 with triflate anhydride to provide the intermediate 2a followed by reaction with tetrabutyl ammonium azide provides the corresponding azide intermediate 2. Trimethylphosphine (Me$_3$P) reduction of the azide intermediate 2 produces the corresponding amino ester 3. N-sulfonylation of the amino ester 3 with a chlorosulfonate (A) provides the corresponding sulfamate 4. Quantitative hydrogenolysis affords the sulfamate acid, which following deprotection to provide intermediate 5, undergoes cyclization to the corresponding β-lactam 6. The β-lactam 6 can be treated with an acid such as methanesulfonic acid to provide the corresponding β-lactam salt 7. The steps are disclosed in Examples 1-7.

Figure 2:
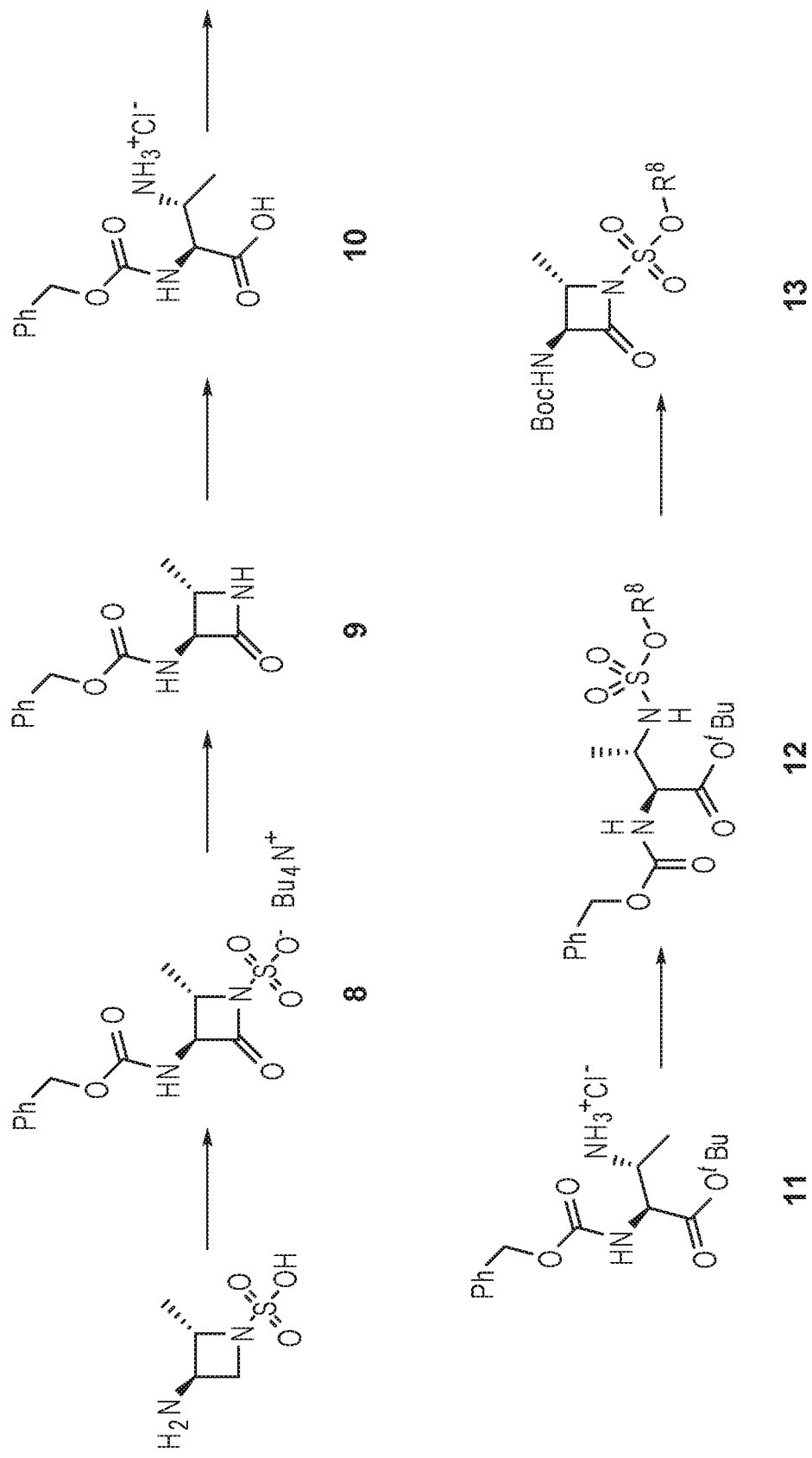
FIG. 2 shows certain steps in synthesizing aztreonam derivatives provided by the present disclosure. The steps correspond to those disclosed in Examples 8-13.

FIG. 2 shows an alternative route for synthesizing the β-lactam 6. Starting from commercially available amino N-sulfonate, formation of the N-Cbz β-lactam 8 followed by desulfation provides the corresponding oxazetidine 9. Treatment of the oxazetidine 9 with aqueous formic acid affords the crystalline amino acid 10. In this case the sulfonylation proceeds from acid 10 to the corresponding to tert-butyl ester 11. The acid can be treated with iso-butylene (Method 1 in Example 11) or with tert-butyl acetate (Method 2 in Example 11) to provide the tert-butyl ester 11. Treatment of the tert-butyl ester with a chlorosulfonate (A) as shown in FIG. 1 provides acid N-sulfonate ester 12. Cyclization of the sulfonate ester 12 gives corresponding β-lactam 13. The amine group of the β-lactam 13 can the be deprotected to provide the corresponding oxoazetidine N-sulfonate ester salt. The steps are provided in Examples 8-13.

Figure 3:
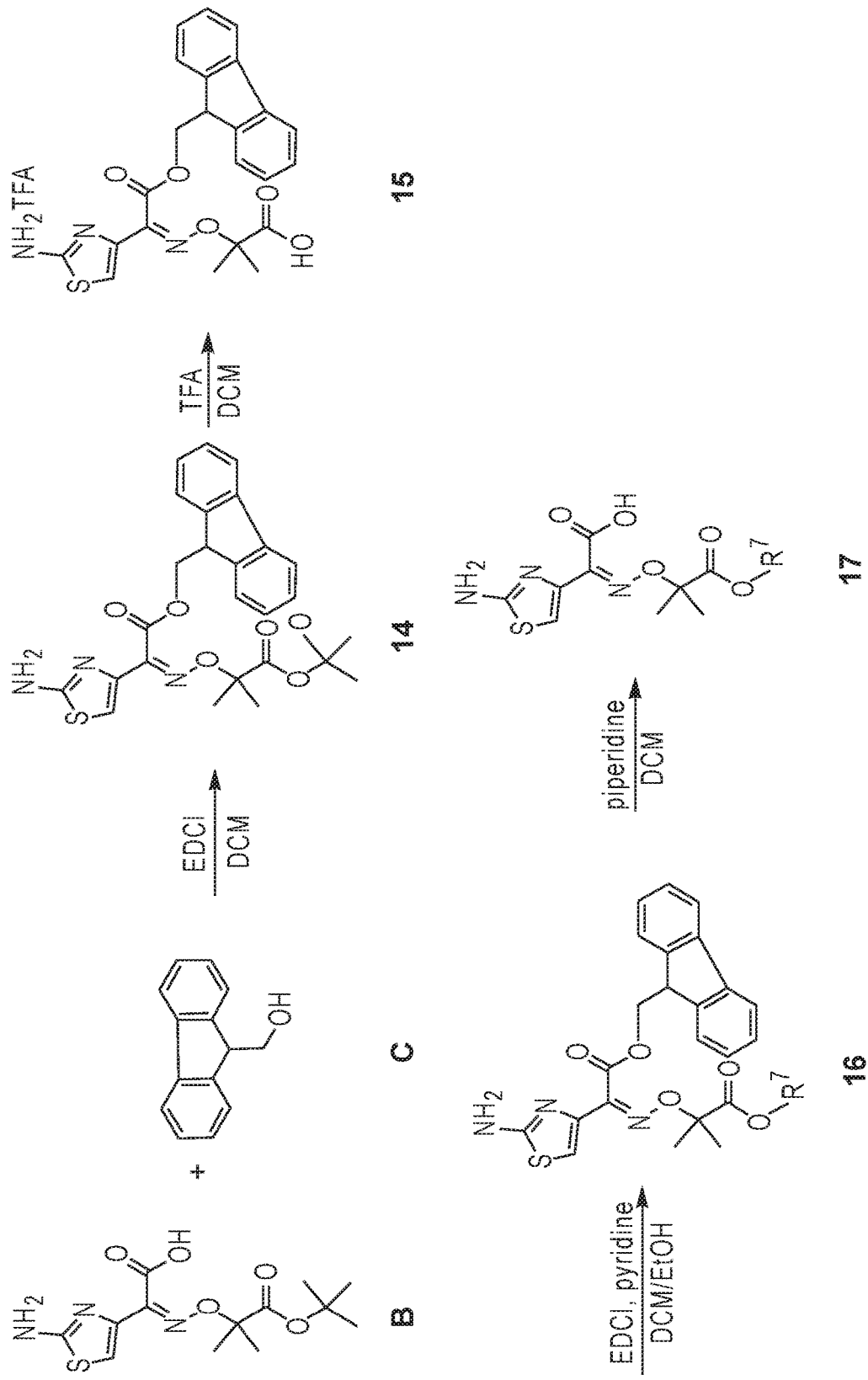
FIG. 3 shows certain steps in synthesizing aztreonam derivatives provided by the present disclosure. The steps correspond to those disclosed in Examples 2 and 27.

FIG. 3 shows a method for preparing a precursor for attaching a 2-((((2-aminothiazol-4-yl)(carboxy)methylene)amino)oxy)-2-methylpropanoic acid sidechain to the N-sulfonated oxazetidine ring. 2-[(2-Amino-thiazol-4-yl)-carboxy-methyleneaminooxy]-2-methyl-propionic acid tert-butyl ester (B) is reacted with (9H-fluoren-9-yl)-methanol (C) to provide the (9H-fluoren-9-yl)-methoxycarbonyl 14. The tert-butoxy group is removed by treating the (9H-fluoren-9-yl)-methoxycarbonyl 14 with an acid to provide the corresponding propionic acid salt 15, which is reacted with an alcohol to provide corresponding propionic acid ester 16. The (9H-fluoren-9-yl) group is removed by treating the propionic acid ester 16 with piperidine to provide the corresponding 2-[(2-amino-thiazol-4-yl)-carboxy-methyleneaminooxy]-2-methyl-propionic acid ester 17. The steps are disclosed in Examples 14-17.

Figure 4:
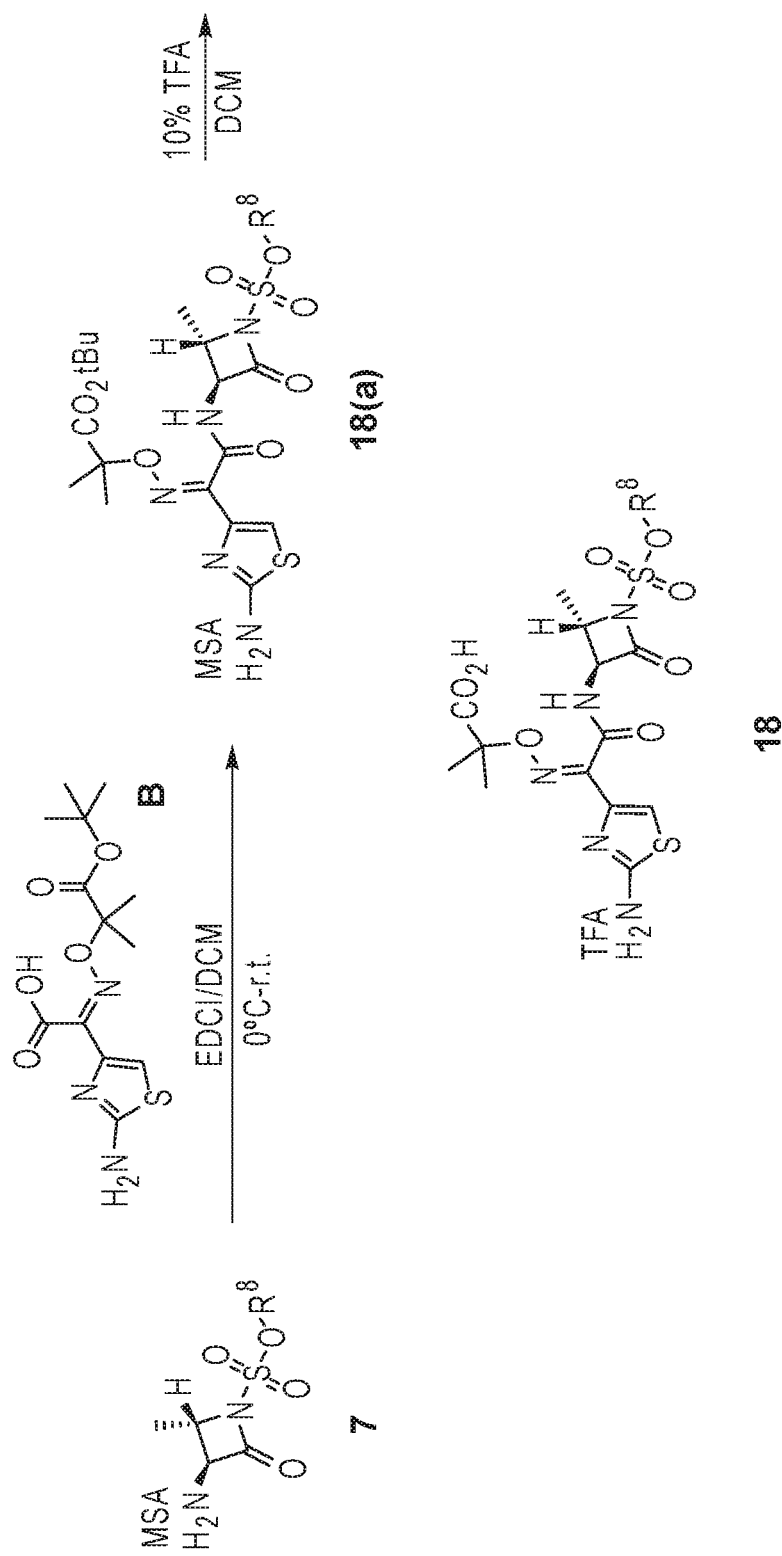
FIG. 4 shows certain steps in synthesizing aztreonam derivatives provided by the present disclosure. The steps correspond to those disclosed in Examples 2 and 27.

FIG. 4 shows a method for attaching a 2-((((2-aminothiazol-4-yl)(carboxy)methylene)amino)oxy)-2-methylpropanoic acid sidechain to the N-sulfonated oxazetidine ring. The β-lactam salt 7 is reacted with the 2-[(2-amino-thiazol-4-yl)-carboxy-methyleneaminooxy]-2-methyl-propionic acid tert-butyl ester (B) in the presence of a carboxyl activating agent to provide the corresponding sulfonyloxy ester 18 (Method 1 in Example 18). Alternatively, as shown in FIG. 4, the β-lactam salt 7 and (Z)-2-(2-aminothiazol-4-yl)-2-(((1-(tert-butoxy)-2-methyl-1-oxopropan-2-yl)oxy)imino)acetic acid are reacted in the presence of a carboxyl coupling agent to provide the tert-butoxy protected β-lactam salt (18a). Deprotection provides the β-lactam salt 18. The steps are disclosed in Example 18 and in FIG. 1 and in FIG. 4.

Figure 5:
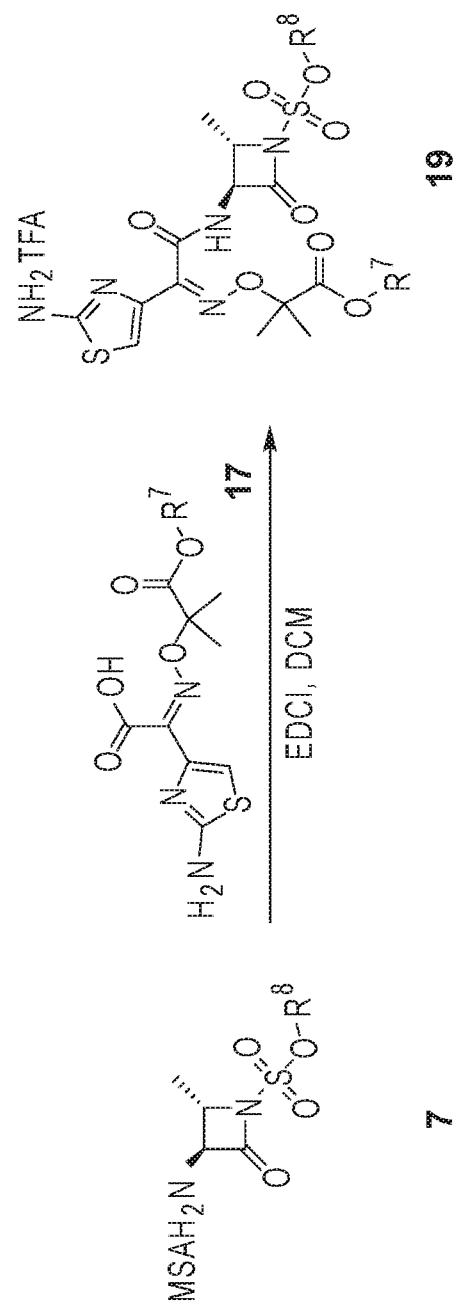
FIG. 5 shows certain steps in synthesizing aztreonam derivatives provided by the present disclosure.

A shown in FIG. 5 and in disclosed in Example 19, a double prodrug can be prepared by reacting the β-lactam salt 7 with a 2-[(2-amino-thiazol-4-yl)-carboxy-methyleneaminooxy]-2-methyl-propionic acid ester 17 in the presence of a carboxyl coupling agent to provide the β-lactam double ester 19.

Methods of synthesizing an organyl 3-amino-2-methyl-4-oxoazetidine-1-sulfonate having the structure of Formula (5):

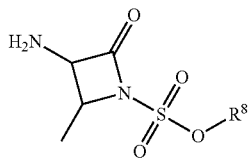

(5)

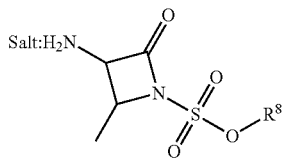

(5a)

or a pharmaceutically acceptable salt thereof, wherein, $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl;

provided by the present disclosure can comprise the steps of:

(e) reacting 3-amino-2-tert-butoxycarbonylamino-butyric acid benzyl ester with an organyl sulfurochloridate having the structure of Formula (6):

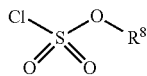

(6)

where $R^8$ is defined as for a compound of Formula (1a), to provide the corresponding tert-butyl (2S,3S)-2-(((benzyloxy)carbonyl)amino)-3-(((3-organyloxy)sulfonyl)amino) butanoate; and (f) after removing the benzyl ester, cyclizing the resulting (1-(tert-butoxy)-3-((organyloxysulfonyl)amino)-1-oxobutan-2-yl)carbamic acid in the presence of a cyclization agent to provide the corresponding organyl 3-((tert-butoxycarbonyl)amino)-2-methyl-4-oxoazetidine-1-sulfonate having the structure of Formula (5).

Methods of synthesizing an organyl 3-amino-2-methyl-4-oxoazetidine-1-sulfonate provided by the present disclosure can further comprising the steps of:

(a) reacting Boc-L-threonine with benzyl bromide to provide 2-tert-butoxycarbonylamino-3-hydroxy-butyric acid benzyl ester;

(b) reacting the 2-tert-butoxycarbonylamino-3-hydroxybutyric acid benzyl ester with trifluoromethane sulfonic anhydride to provide the corresponding trifluoro ester;

(c) reacting the trifluoro ester with $Bu_4NN_3$ to provide 3-azido-2-tert-butoxycarbonylamino-butyric acid benzyl ester; and (d) reacting the 3-azido-2-tert-butoxycarbonylamino-butyric acid benzyl ester with trimethylphosphine to provide 3-amino-2-tert-butoxycarbonylamino-butyric acid benzyl ester.

A salt can comprise the methanesulfonic acid salt, the triethylamine salt, the trifluoroacetic acid salt, or a combination of any of the foregoing.

A salt can comprise a pharmaceutically acceptable salt.

Methods of synthesizing an organyl 3-amino-2-methyl-4-oxoazetidine-1-sulfonate provided by the present disclosure can further comprise the step of:

(g) treating the organyl 3-((tert-butoxycarbonyl)amino)-2-methyl-4-oxoazetidine-1-sulfonate with an acid to provide the corresponding organyl 3-amino-2-methyl-4-oxoazetidine-1-sulfonate salt having the structure of Formula (5a):

wherein $R^8$ is defined as for a compound of Formula (4). The acid can comprise, for example, methanesulfonic acid, triethylamine, trifluoroacetic acid, or a combination of any of the foregoing; and the salt can comprise, for example the methanesulfonic acid salt, the triethylamine salt, the trifluoroacetic acid salt, or a combination of any of the foregoing, respectively.

In compounds of Formula (1a), the organyl group $R^8$ can comprise a neopentyl moiety and $R^8$ can have the structure of Formula (2):

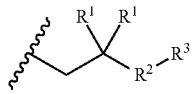

(2)

wherein, each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—O—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

In methods provided by the present disclosure the organyl 3-amino-2-methyl-4-oxoazetidine-1-sulfonate methanesulfonic acid can have the structure of Formula (5a) and the organyl sulfurochloridate can be a neopentyl sulfurochloridate having the structure of Formula (5b):

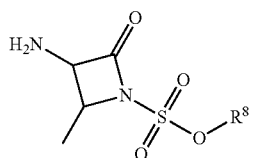

(5b)

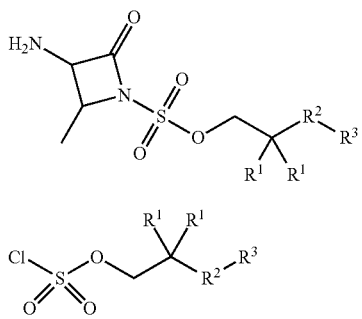

(6a)

wherein, each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

In step (f), removing the benzyl ester can comprise, for example, treating the tert-butyl (2S,3S)-2-(((benzyloxy)carbonyl)amino)-3-(((3-organyloxy)sulfonyl)amino)butanoate with Pd/C.

In methods provided by the present disclosure a cyclization agent can comprise, for example, N,N,N',N'-tetramethylchloroformamidinium hexafluorophosphate (TCFH), dicyclohexylcarbodiimide (DCC), diisopropylcarbondimide (DIC), ethyl-(N',N'-dimethylamino)propylcarbodiimide hydrochloride (EDC), or a combination of any of the foregoing.

Compounds provided by the present disclosure include an organyl 3-amino-2-methyl-4-oxoazetidine-1-sulfonate having the structure of Formula (5) or a salt thereof prepared by a method provided by the present disclosure.

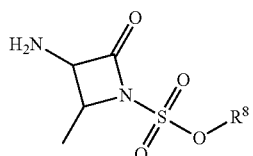

(5)

wherein $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl.

A salt of a compound of Formula (5) can comprise the methanesulfonic acid salt, the triethylamine salt, the trifluoroacetic acid salt, or a combination of any of the foregoing.

In compounds of Formula (5), $R^8$ can be a neopentyl group having the structure of Formula (2):

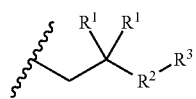

(2)

wherein, each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Thus, compounds provided by the present disclosure or salts thereof prepared by methods provided by the present disclosure can have the structure of Formula (5b):

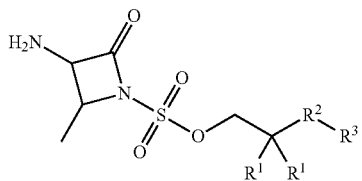

(5b)

wherein,
each $R^1$ is independently $C_{1-6}$ alkyl, or each R and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

A method of synthesizing an organyl 3-amino-2-methyl-4-oxoazetidine-1-sulfonate having the structure of Formula (5):

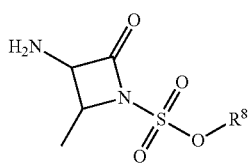

(5)

or a salt thereof, wherein,
$R^8$ is selected from $C_{1-2}$ alkyl, $C_{1-2}$ alkanecycloalkyl, $C_{1-2}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl;

provided by the present disclosure can comprise the steps of:

(e) reacting tert-butyl (2S,3R)-3-amino-2-(((benzyloxy)carbonyl)-amino)butanoate with an organyl sulfurochloridate of Formula (6):

(6)

to provide the corresponding tert-butyl (2S,3S)-2-(((benzyloxy)carbonyl)amino)-3-(((3-organyloxy) sulfonyl)amino) butanoate; and (f) following removal of the benzyl ester, cyclizing the resulting 2-tert-butoxycarbonylamino-3-(2-organyloxysulfonyl-amino)-butyric acid in the presence of a cyclization agent to provide the corresponding organyl 3-((tert-butoxycarbonyl)amino)-2-methyl-4-oxoazetidine-1-sulfonate having the structure of Formula (5).

Methods of synthesizing an organyl 3-amino-2-methyl-4-oxoazetidine-1-sulfonate can further comprise the steps of:

(a) reacting (2S,3S)-3-amino-2-methyl-4-oxo-1-azetidinesulfonic acid with benzyloxycarbonyl N-succinimide in the presence of Et$_3$N to provide tetrabutylammonium (2S,3S)-3-(((benzyloxy)carbonyl)amino)-2-methyl-4-oxoazetidine-1-sulfonate TEA salt;

(b) treating the TEA salt with trifluoroacetic acid to provide benzyl ((2S,3S)-2-methyl-4-oxoazetidin-3-yl)carbamate;

(c) treating the benzyl ((2S,3S)-2-methyl-4-oxoazetidin-3-yl)carbamate with formic acid followed by hydrochloric acid to provide (2S,3R)-3-amino-2-(((benzyloxy)carbonyl)amino)butanoic acid HCl salt; and (d) forming the tert-butyl ester.

In step (d), forming the tert-butyl ester can comprise (d1) reacting the (2S,3R)-3-amino-2-(((benzyloxy)carbonyl)amino)butanoic acid HCl salt with iso-butylene.

In step (d), forming the tert-butyl ester can comprise forming the tert-butyl ester comprises (d2) reacting the (2S,3R)-3-amino-2-(((benzyloxy)carbonyl)amino)butanoic acid HCl salt with tert-butyl acetate.

Methods of synthesizing an organyl 3-amino-2-methyl-4-oxoazetidine-1-sulfonate of Formula (5) can further comprise the step of:

(g) treating the corresponding organyl 3-((tert-butoxycarbonyl)amino)-2-methyl-4-oxoazetidine-1-sulfonate with an acid or a base to provide the corresponding organyl 3-amino-2-methyl-4-oxoazetidine-1-sulfonate salt.

The acid can comprise, for example, methanesulfonic acid, triethylamine, trifluoroacetic acid, or a combination of any of the foregoing.

The salt can comprise, for example, the methanesulfonic acid salt, the triethylamine salt, the trifluoroacetic acid salt, or a combination of any of the foregoing.

Methods of synthesizing 2-[(2-amino-thiazol-4-yl)-carboxy-methyleneaminooxy]-2-methyl-propionic acid ester having the structure of Formula (7) provided by the present disclosure can comprise the steps of:

(a) reacting 2-[(2-amino-thiazol-4-yl)-carboxy-methyleneaminooxy]-2-methyl-propionic acid tert-butyl ester (B) and (9H-fluoren-9-yl)-methanol (C) in the presence of a carboxyl activating agent to provide 2-[(2-amino-thiazol-4-yl)-(9H-fluoren-9-ylmethoxycarbonyl)-methyleneaminooxy]-2-methyl-propionic acid tert-butyl ester;

(b) treating the 2-[(2-amino-thiazol-4-yl)-(9H-fluoren-9-ylmethoxycarbonyl)-methyleneaminooxy]-2-methyl-propionic acid tert-butyl ester with an acid to provide the corresponding salt;

(c) reacting the salt with an alcohol in the presence of a carboxyl activating agent to provide the corresponding 2-[(2-amino-thiazol-4-yl)-(9H-fluoren-9-ylmethoxycarbonyl)-methyleneaminooxy]-2-methyl-propionic acid ester; and (d) removing the (9H-fluoren-9-yl)-methyl group by treating the 2-[(2-amino-thiazol-4-yl)-(9H-fluoren-9-ylmethoxycarbonyl)-methyleneaminooxy]-2-methyl-propionic acid ester with pyridine to provide the corresponding 2-[(2-amino-thiazol-4-yl)-carboxy-methyleneaminooxy]-2-methyl-propionic acid ester, wherein the 2-[(2-amino-thiazol-4-yl)-carboxy-methyleneaminooxy]-2-methyl-propionic acid ester has the structure of Formula (7):

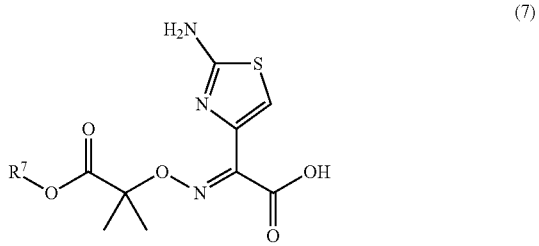

(7)

wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{10}$ heterocycloalkylalkyl, $C_{6-8}$ aryl, $C_{5-8}$ heteroaryl, $C_{7-10}$ arylalkyl, $C_{10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

The acid can comprise trifluoroacetic acid and the salt can be the trifluoroacetic acid salt.

Examples of suitable carboxyl activating agents include N-(3-dimethylaminopropyl)-N'-ethylcarbodiimide hydrochloride (EDCI), 1-[bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), N,N,N',N'-tetramethyl-O-(benzotriazol-1-yl)uronium tetrafluoroborate (TBTU), 1-propanephosphonic anhydride solution, 2,4,6-tripropyl-1,3,5,2,4,6-trioxatriphosphorinane-2,4,6-trioxide (T3P), and a combination of any of the foregoing.

A suitable alcohol can have the structure of Formula (8):

$R^7$—OH (8)

wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

In alcohols of Formula (8), $R^7$ can be selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, and $C_{5-10}$ heteroarylalkyl.

In alcohols of Formula (8), $R^7$ can be selected from $C_{1-8}$ alkyl and $C_{1-8}$ heteroalkyl.

In alcohols of Formula (8), $R^7$ can be selected from $C_{5-8}$ cycloalkyl and $C_{5-8}$ heterocycloalkyl.

In alcohols of Formula (8), $R^7$ can be selected from $C_{5-10}$ cycloalkylalkyl and $C_{5-10}$ heterocycloalkylalkyl.

In alcohols of Formula (8), $R^7$ can be selected from $C_{6-8}$ aryl and $C_{5-8}$ heteroaryl.

In alcohols of Formula (8), $R^7$ can be selected from $C_{7-10}$ arylalkyl and $C_{5-10}$ heteroarylalkyl.

In alcohols of Formula (8), $R^7$ can be selected from methyl, ethyl, n-propyl, n-butyl, n-pentyl, and n-hexyl.

For example, in methods of synthesizing 2-[(2-amino-thiazol-4-yl)-carboxy-methyleneaminooxy]-2-methyl-propionic acid ester (7): the acid ester (7) can be the ethyl ester and the alcohol in step (c) can be ethanol; the acid ester (7) can be the benzyl ester and the alcohol in step (c) can be benzyl alcohol; the acid ester (7) can be 2-methoxy ethyl ester and the alcohol in step (c) is 2-methoxyethanol; the acid ester (7) can be the hexyl ester and the alcohol in step (c) is 1-hexanol; or the acid ester (7) can be the medoxamil ester and the alcohol in step (c) can be 4-(hydroxymethyl)-5-methyl-1,3-dioxol-2-one.

Compounds provided by the present disclosure include 2-[(2-amino-thiazol-4-yl)-carboxy-methyleneaminooxy]-2-methyl-propionic acid ester, or a salt thereof, synthesized using the methods provided by the present disclosure, wherein the compound has the structure of Formula (7):

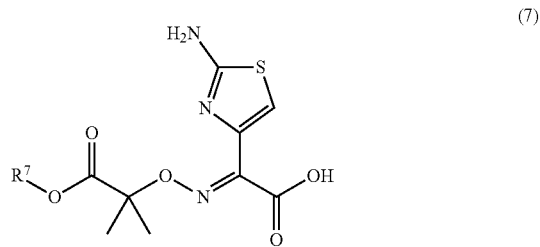

(7)

wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Methods provided by the present disclosure include reacting an organyl 3-amino-2-methyl-4-oxoazetidine-1-sulfonate salt with a 2-[(2-amino-thiazol-4-yl)-carboxy-methyleneaminooxy]-2-methyl-propionic acid ester in the presence of a carboxyl activating agent to provide the corresponding aztreonam derivative of Formula (1a):

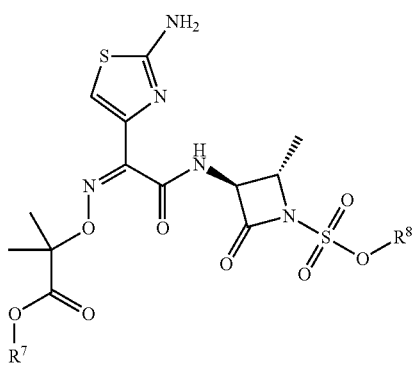

(1a)

or a pharmaceutically acceptable salt thereof, wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl.

The organyl 3-amino-2-methyl-4-oxoazetidine-1-sulfonate salt can have the structure of Formula (5a):

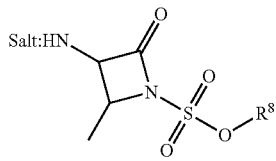

(5a)

wherein, $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; and the 2-[(2-amino-thiazol-4-yl)-carboxy-methyleneaminooxy]-2-methyl-propionic acid ester can have the structure of Formula (7):

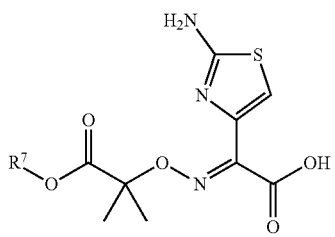

(7)

wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Examples of suitable carboxyl activating agents include N-(3-dimethylaminopropyl)-N'-ethylcarbodiimide hydrochloride (EDCI), 1-[bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), N,N,N',N'-tetramethyl-O-(benzotriazol-1-yl)uronium tetrafluoroborate (TBTU), 1-propanephosphonic anhydride solution, 2,4,6-tripropyl-1,3,5,2,4,6-trioxatriphosphorinane-2,4,6-trioxide (T3P), or a combination of any of the foregoing.

A salt can comprise, for example, the methanesulfonic acid salt, the triethylamine salt, the trifluoroacetic acid salt, or a combination of any of the foregoing.

In organyl 3-amino-2-methyl-4-oxoazetidine-1-sulfonate salts of Formula (5a), $R^8$ can be a neopentyl group and can have the structure of Formula (2):

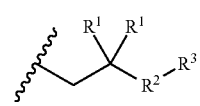

(2)

wherein, each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

A method of synthesizing an aztreonam derivative can further comprise (b) treating the tert-butoxy protected ester salt (1a) with an acid to provide the corresponding aztreonam sulfonyloxy organyl ester salt having the structure of Formula (1a):

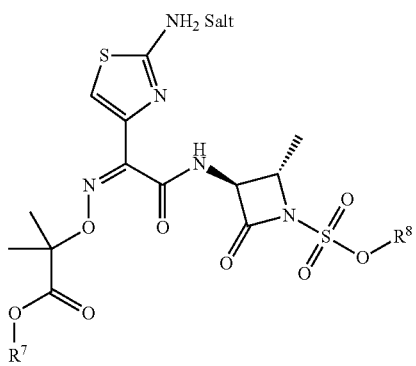

(1a)

Methods of synthesizing an aztreonam derivative of Formula (1a) can comprise:

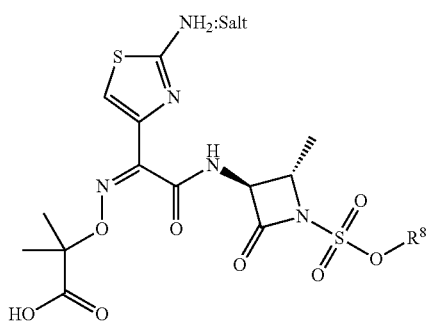

(1a)

or a pharmaceutically acceptable salt thereof wherein, $R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl;

(a) reacting an organyl 3-amino-2-methyl-4-oxoazetidine-1-sulfonate salt with a 2-[(2-amino-thiazol-4-yl)-carboxy-methyleneaminooxy]-2-methyl-propionic acid tert-butyl ester in the presence of a carboxyl coupling agent to provide the corresponding tert-butoxy protected salt; and (b) treating the tert-butoxy protected salt with an acid to provide the corresponding aztreonam sulfonyloxy organyl ester salt (1c), wherein, the organyl 3-amino-2-methyl-4-oxoazetidine-1-sulfonate salt has the structure of Formula (5):

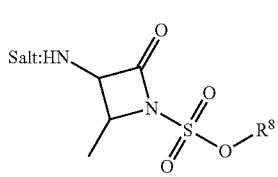

(5)

wherein, $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; and the 2-[(2-amino-thiazol-4-yl)-carboxy-methyleneaminooxy]-2-methyl-propionic acid tert-butyl ester can have the structure of Formula (7a):

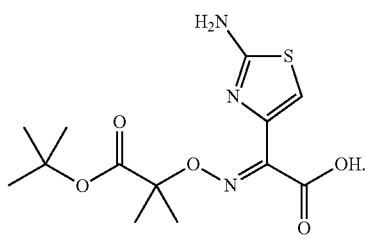

(7a)

Examples of suitable carboxyl activating agents include N-(3-dimethylaminopropyl)-N'-ethylcarbodiimide hydrochloride (EDCI), 1-[bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), N,N,N',N'-tetramethyl-O-(benzotriazol-1-yl)uronium tetrafluoroborate (TBTU), 1-propanephosphonic anhydride solution, 2,4,6-tripropyl-1,3,5,2,4,6-trioxatriphosphorinane-2,4,6-trioxide (T3P), or a combination of any of the foregoing.

A salt of an aztreonam derivative of Formula (1a) or Formula (1b) can comprise the methanesulfonic acid salt, the triethylamine salt, the trifluoroacetic acid salt, or a combination of any of the foregoing.

In methods of preparing an aztreonam derivative (a) reacting can comprise reacting at a temperature from 20° C. to 30° C.

In methods of preparing an aztreonam derivative treating the tert-butoxy protected aztreonam salt (7a) can comprise treating at a temperature from 20° C. to 30° C.

In methods of preparing an aztreonam derivative the organyl 3-amino-2-methyl-4-oxoazetidine-1-sulfonate methanesulfonic acid salt (5) is prepared by a method provided by the present disclosure.

In methods of preparing an aztreonam derivative the 2-[(2-amino-thiazol-4-yl)-carboxy-methyleneaminooxy]-2-methyl-propionic acid ester (7) is prepared by a method provided by the present disclosure.

An aztreonam sulfonyloxy organyl ester salt prepared by methods provided by the present disclosure can have the structure of Formula (1b):

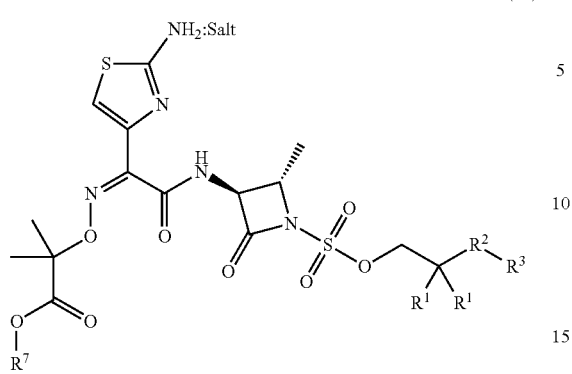

(1b)

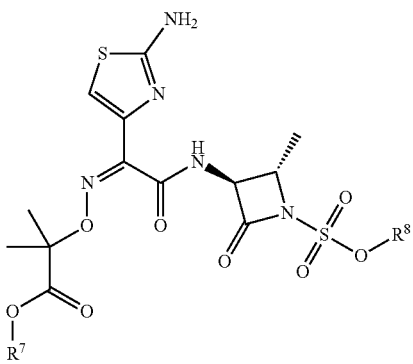

(1a)

wherein, each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^7$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl.

An aztreonam sulfonyloxy organyl ester salt prepared by methods provided by the present disclosure can have the structure of Formula (1a):

or a pharmaceutically acceptable salt thereof, wherein, $R^7$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl.

Aztreonam derivatives provided by the present disclosure or pharmaceutically acceptable salts thereof including aztreonam derivatives of Formula (1a)-(1d) may be incorporated into pharmaceutical compositions to be administered to a patient by any appropriate route of administration including intradermal, intramuscular, intraperitoneal, intravenous, subcutaneous, intranasal, epidural, oral, peroral, sublingual, intracerebral, intravaginal, transdermal, rectal, inhalation, or topical. Pharmaceutical compositions provided by the present disclosure can be provided as oral formulations. Oral formulations may be oral dosage forms.

Pharmaceutical compositions provided by the present disclosure may comprise a therapeutically-effective amount of a compound of Formula (1a)-(1d) or a pharmaceutically acceptable salt thereof together with a suitable amount of one or more pharmaceutically acceptable vehicles so as to provide a composition for proper administration to a patient. Suitable pharmaceutical vehicles and methods of preparing pharmaceutical compositions are described in the art. Examples of suitable pharmaceutical vehicles are described in the art.

Pharmaceutical compositions provided by the present disclosure can comprise a β-lactamase inhibitor. A β-lactamase inhibitor can comprise an orally bioavailable β-lactamase inhibitor. A β-lactamase inhibitor can comprise a derivative of a β-lactamase inhibitor, which when orally administered to a patient provides the β-lactamase inhibitor in the systemic circulation of the patient.

Examples of orally bioavailable β-lactamase inhibitors include derivatives having the structure of Formula (8):

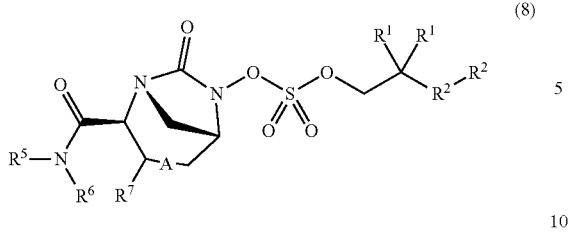

(8)

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl;

$R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and A is a single bond (—) and $R^7$ is hydrogen, or A is a double bond (═) and $R^7$ is $C_{1-3}$ alkyl.

Derivatives of β-lactamase inhibitors within the scope of Formula (8) include derivatives of avibactam, derivatives of relebactam, and derivatives of nacubactam.

Derivatives encompassed by Formula (8) can have the structure of Formula (8a), a derivative of relebactam can have the structure of Formula (9), and a derivative of nacubactam can have the structure of Formula (10):

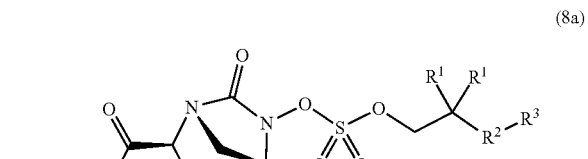

(8a)

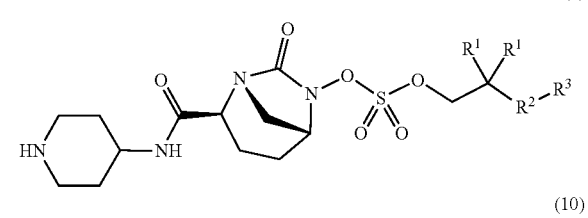

(9)

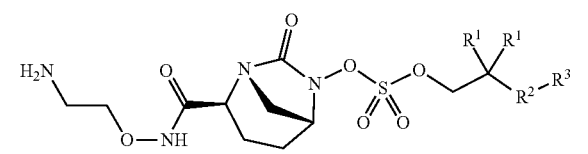

(10)

or a pharmaceutically acceptable salt thereof, wherein, each $R^1$ is independently selected from $C_{1-6}$ alkyl, or each $R^1$ and the geminal carbon atom to which they are bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl;

$R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, substituted $C_{5-6}$ heteroaryl, and —CH=C($R^4$)$_2$, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl;

$R^5$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^6$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl.

Aztreonam derivatives provided by the present disclosure are prodrugs of aztreonam that are metabolized in vivo to produce the β-lactam antibiotic, aztreonam. The aztreonam derivatives provided by the present disclosure can be used to treat any disease or condition for which aztreonam is effective in treating. Aztreonam derivatives provided by the present disclosure can be used to treat bacterial infections.

Methods of treating a bacterial infection in a patient comprise administering to a patient in need of such treatment a therapeutically effective amount of a compound of Formula (1a)-(1d). Administering an aztreonam derivative of Formula (1a)-(1d) can comprise orally administering.

Administering can comprise orally administering such as administering an oral dosage form comprising an aztreonam derivative of Formula (1a)-(1d).

Methods of treating a bacterial infection further comprise administering one or more additional antibiotics to the patient in addition to the aztreonam derivative. The one or more additional antibiotics can comprise a β-lactam antibiotic.

Methods of treating a bacterial infection can further comprise administering a β-lactamase inhibitor to the patient.

Administering the β-lactamase inhibitor can comprise orally administering a β-lactamase inhibitor.

Administering a β-lactamase inhibitor can comprise orally administering a compound that provides a therapeutically effective amount of a β-lactamase inhibitor to a site of a bacterial infection in a patient.

The β-lactamase inhibitor can comprise a derivative of a β-lactamase inhibitor, which when orally administered to a patient, provides the β-lactamase inhibitor at the site of a bacterial infection in the patient.

It should be understood that any suitable combination of the compounds and pharmaceutical compositions provided herein with one or more of the above therapeutic agents and optionally one or more further pharmacologically active substances are considered to be within the scope of the present disclosure. In some embodiments, the compounds and pharmaceutical compositions provided by the present disclosure are administered prior to or subsequent to the one or more additional active ingredients.

ASPECTS OF THE INVENTION

The invention is further defined by the following aspects.

Aspect 1. A method of synthesizing an organyl 3-amino-2-methyl-4-oxoazetidine-1-sulfonate having the structure of Formula (5):

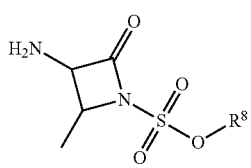

(5)

or a salt thereof, wherein, $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl;

comprising the steps of:

(e) reacting 3-amino-2-tert-butoxycarbonylamino-butyric acid benzyl ester with an organyl sulfurochloridate having the structure of Formula (6):

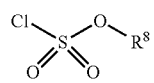

(6)

to provide the corresponding tert-butyl (2S,3S)-2-(((benzyloxy)carbonyl)amino)-3-(((3-organyloxy)sulfonyl)amino)butanoate; and (f) after removing the benzyl ester, cyclizing the resulting (1-(tert-butoxy)-3-((organyloxysulfonyl)amino)-1-oxobutan-2-yl)carbamic acid in the presence of a cyclization agent to provide the corresponding organyl 3-((tert-butoxycarbonyl)amino)-2-methyl-4-oxoazetidine-1-sulfonate having the structure of Formula (5).

Aspect 2. The method of aspect 1, further comprising the steps of:

(a) reacting Boc-L-threonine with benzyl bromide to provide 2-tert-butoxycarbonylamino-3-hydroxy-butyric acid benzyl ester;

(b) reacting the 2-tert-butoxycarbonylamino-3-hydroxy-butyric acid benzyl ester with trifluoromethane sulfonic anhydride to provide the corresponding trifluoro ester; (c) reacting the trifluoro ester with $Bu_4NN_3$ to provide 3-azido-2-tert-butoxycarbonylamino-butyric acid benzyl ester; and (d) reacting the 3-azido-2-tert-butoxycarbonylamino-butyric acid benzyl ester with trimethylphosphine to provide 3-amino-2-tert-butoxycarbonylamino-butyric acid benzyl ester.

Aspect 3. The method of any one of aspects 1 to 2, wherein the salt comprises the methanesulfonic acid salt, the triethylamine salt, the trifluoroacetic acid salt, or a combination of any of the foregoing.

Aspect 4. The method of any one of aspects 1 to 3, further comprising the step of: (g) treating the organyl 3-((tert-butoxycarbonyl)amino)-2-methyl-4-oxoazetidine-1-sulfonate with an acid to provide the corresponding organyl 3-amino-2-methyl-4-oxoazetidine-1-sulfonate salt having the structure of Formula-(5a):

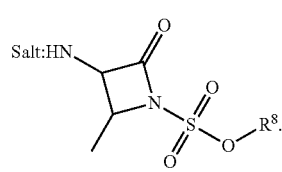

(5a)

Aspect 5. The method of aspect 4, wherein the acid comprises methanesulfonic acid, triethylamine, trifluoroacetic acid, or a combination of any of the foregoing.

Aspect 6. The method of any one of aspects 1 to 5, wherein $R^8$ comprises a neopentyl moiety and the organyl group is a neopentyl group, wherein $R^8$ has the structure of Formula (2):

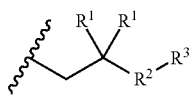
(2)

wherein,
each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein,
$R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 8. The method of any one of aspects 1 to 7, wherein removing the benzyl ester comprises treating the tert-butyl (2S,3S)-2-(((benzyloxy)carbonyl)amino)-3-(((3-organyloxy)sulfonyl)amino)butanoate with Pd/C.

Aspect 9. The method of any one of aspects 1 to 8, wherein the cyclization agent comprises N,N,N',N'-tetramethylchloroformamidinium hexafluorophosphate (TCFH), dicyclohexylcarbodimide (DCC), diisopropylcarbondimide (DIC), ethyl-(N',N'-dimethylamino)propylcarbodiimide hydrochloride (EDC), or a combination of any of the foregoing.

Aspect 10. A compound, organyl 3-amino-2-methyl-4-oxoazetidine-1-sulfonate, having the structure of Formula (5) or a salt thereof prepared by the method of any one of aspects 1 to 9:

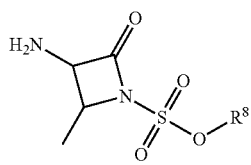
(5)

wherein $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl.

Aspect 11. The compound of aspect 10, wherein the salt comprises the methanesulfonic acid salt, the triethylamine salt, the trifluoroacetic acid salt, or a combination of any of the foregoing.

Aspect 12. The compound of any one of aspects 10 to 11, wherein $R^8$ is a neopentyl group having the structure of Formula (2):

Aspect 7. The method of any one of aspects 1 to 6, wherein the organyl 3-amino-2-methyl-4-oxoazetidine-1-sulfonate methanesulfonic acid has the structure of Formula (5b) and the organyl sulfurochloridate is a neopentyl sulfurochloridate having the structure of Formula (6a):

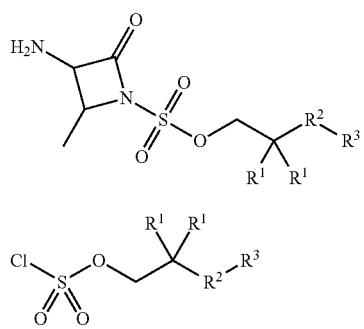
(5b)
(6a)

wherein,
each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

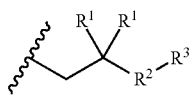

(2)

wherein,
each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 13. The compound of any one of aspects 10 to 12, wherein the compound has the structure of Formula (5b):

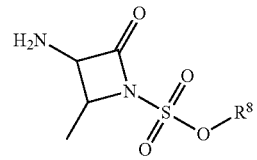

(5b)

wherein,
each $R^1$ is independently $C_{1-6}$ alkyl, or each R and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 14. A method of synthesizing an organyl 3-amino-2-methyl-4-oxoazetidine-1-sulfonate having the structure of Formula (5):

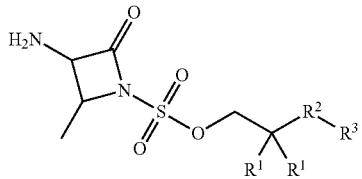

(5)

or a salt thereof, wherein,
$R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; comprising the steps of:

(e) reacting tert-butyl (2S,3R)-3-amino-2-(((benzyloxy)carbonyl)-amino)butanoate with an organyl sulfurochloridate of Formula (6):

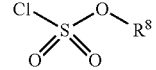

(6)

to provide the corresponding tert-butyl (2S,3S)-2-(((benzyloxy)carbonyl)amino)-3-(((3-organyloxy) sulfonyl)amino) butanoate; and (f) following removal of the benzyl ester, cyclizing the resulting 2-tert-butoxycarbonylamino-3-(2-organyloxysulfonyl-amino)-butyric acid in the presence of a cyclization agent to provide the corresponding organyl 3-((tert-butoxycarbonyl)amino)-2-methyl-4-oxoazetidine-1-sulfonate having the structure of Formula (5).

Aspect 15. The method of aspect 14, further comprising:

(a) reacting (2S,3S)-3-amino-2-methyl-4-oxo-1-azetidinesulfonic acid with benzyloxycarbonyl N-succinimide in the presence of Et$_3$N to provide tetrabutylammonium (2S,3S)-3-(((benzyloxy)carbonyl)amino)-2-methyl-4-oxoazetidine-1-sulfonate TEA salt;

(b) treating the TEA salt with trifluoroacetic acid to provide benzyl ((2S,3S)-2-methyl-4-oxoazetidin-3-yl)carbamate;

(c) treating the benzyl ((2S,3S)-2-methyl-4-oxoazetidin-3-yl)carbamate with formic acid followed by hydrochloric acid to provide (2S,3R)-3-amino-2-(((benzyloxy)carbonyl)amino)butanoic acid HCl salt; and (d) forming the tert-butyl ester.

Aspect 16. The method of aspect 15, wherein forming the tert-butyl ester comprises (d1) reacting the (2S,3R)-3-amino-2-(((benzyloxy)carbonyl)amino)butanoic acid HCl salt with iso-butylene.

Aspect 17. The method of aspect 15, wherein forming the tert-butyl ester comprises (d2) reacting the (2S,3R)-3-amino-2-(((benzyloxy)carbonyl)amino)butanoic acid HCl salt with tert-butyl acetate.

Aspect 18. The method of any one of aspects 14 to 17, further comprising:

(g) treating the corresponding organyl 3-((tert-butoxycarbonyl)amino)-2-methyl-4-oxoazetidine-1-sulfonate with an acid to provide the corresponding organyl 3-amino-2-methyl-4-oxoazetidine-1-sulfonate salt.

Aspect 19. The method of aspect 18, wherein the acid comprises methanesulfonic acid, triethylamine, trifluoroacetic acid, or a combination of any of the foregoing.

Aspect 20. The method of any one of aspects 14 to 19, wherein the salt comprises the methanesulfonic acid salt, the triethylamine salt, the trifluoroacetic acid salt, or a combination of any of the foregoing.

Aspect 21. A compound, organyl 3-amino-2-methyl-4-oxoazetidine-1-sulfonate, prepared by the method of any one of aspects 14 to 20, wherein the compound has the structure of Formula (5):

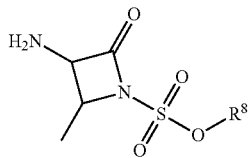

(5)

or a salt thereof, wherein, $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl.

Aspect 22. The compound of aspect 21, wherein $R^8$ is a neopentyl group having the structure of Formula (2):

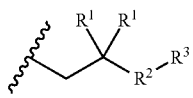

(2)

wherein, each $R^1$ is independently $C_{1-6}$ alkyl, or each R and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 23. The compound of any one of aspects 21 to 22, wherein the compound has the structure of Formula (5b):

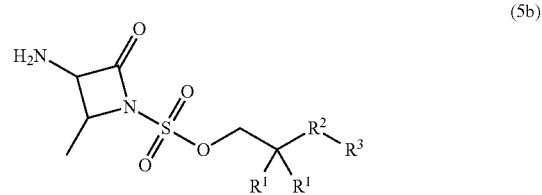

(5b)

or a salt thereof, wherein, each $R^1$ is independently $C_{1-6}$ alkyl, or each R and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroaryllalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 24. The compound of any one of aspects 21 to 23, wherein the salt comprises the methanesulfonic acid salt, the triethylamine salt, the trifluoroacetic acid salt, or a combination of any of the foregoing.

Aspect 25. A method of synthesizing 2-[(2-amino-thiazol-4-yl)-carboxy-methyleneaminooxy]-2-methyl-propionic acid ester, comprising the steps of:

(a) reacting 2-[(2-amino-thiazol-4-yl)-carboxy-methyleneaminooxy]-2-methyl-propionic acid tert-butyl ester and (9H-fluoren-9-yl)-methanol in the presence of a carboxyl activating agent to provide 2-[(2-amino-thiazol-4-yl)-(9H-fluoren-9-ylmethoxycarbonyl)-methyleneaminooxy]-2-methyl-propionic acid tert-butyl ester;

(b) treating the 2-[(2-amino-thiazol-4-yl)-(9H-fluoren-9-ylmethoxycarbonyl)-methyleneaminooxy]-2-methyl-propionic acid tert-butyl ester with an acid to provide the corresponding salt;

(c) reacting the salt with an alcohol in the presence of a carboxyl activating agent to provide the corresponding 2-[(2-amino-thiazol-4-yl)-(9H-fluoren-9-ylmethoxycarbonyl)-methyleneaminooxy]-2-methyl-propionic acid ester; and (d) removing the (9H-fluoren-9-yl)-methyl group by treating the 2-[(2-amino-thiazol-4-yl)-(9H-fluoren-9-ylmethoxycarbonyl)-methyleneaminooxy]-2-methyl-propionic acid ester with pyridine to provide the corresponding 2-[(2-amino-thiazol-4-yl)-carboxy-methyleneaminooxy]-2-methyl-propionic acid ester, wherein the 2-[(2-amino-thiazol-4-yl)-carboxy-methyleneaminooxy]-2-methyl-propionic acid ester has the structure of Formula (7):

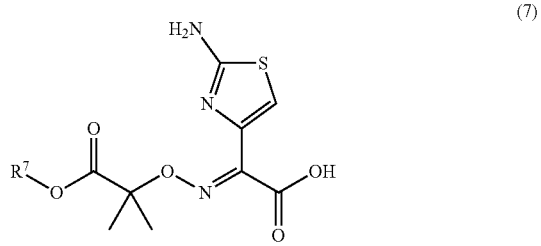

(7)

wherein,
$R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 26. The method of aspect 25, wherein the acid is trifluoroacetic acid and the salt is the trifluoroacetic acid salt.

Aspect 27. The method of any one of aspects 25 to 26, wherein the carboxyl activating agent is selected from N-(3-dimethylaminopropyl)-N'-ethylcarbodiimide hydrochloride (EDCI), 1-[bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), N,N,N',N'-tetramethyl-O-(benzotriazol-1-yl)uronium tetrafluoroborate (TBTU), 1-propanephosphonic anhydride solution, 2,4,6-tripropyl-1,3,5,2,4,6-trioxatriphosphorinane-2,4,6-trioxide (T3P), or a combination of any of the foregoing.

Aspect 28. The method of any one of aspects 25 to 27, wherein the alcohol has the structure of Formula (8):

wherein,
$R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 29. The method of any one of aspects 25 to 28, wherein, the acid ester (7) is the ethyl ester and the alcohol in step (c) is ethanol;

the acid ester (7) is the benzyl ester and the alcohol in step (c) is benzyl alcohol;

the acid ester (7) is 2-methoxy ethyl ester and the alcohol in step (c) is 2-methoxyethanol;

the acid ester (7) is the hexyl ester and the alcohol in step (c) is 1-hexanol; or the acid ester (7) is the medoxamil ester and the alcohol in step (c) is 4-(hydroxymethyl)-5-methyl-1,3-dioxol-2-one.

Aspect 30. A compound, 2-[(2-amino-thiazol-4-yl)-carboxy-methyleneaminooxy]-2-methyl-propionic acid ester, or a salt thereof, synthesized using the method of any one of aspects 25 to 29, wherein the compound has the structure of Formula (7):

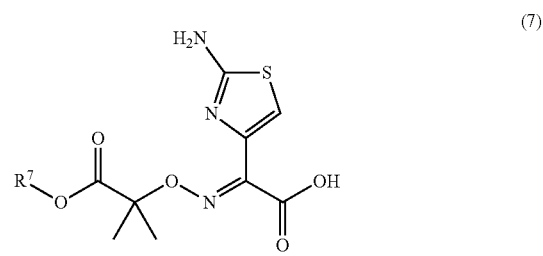

(7)

wherein,
$R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 31. A method of synthesizing an aztreonam derivative of Formula (1a):

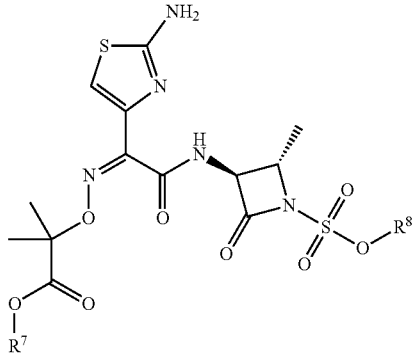

or a pharmaceutically acceptable salt thereof, wherein,
$R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl;

comprising (a) reacting an organyl 3-amino-2-methyl-4-oxoazetidine-1-sulfonate salt with a 2-[(2-amino-thiazol-4-yl)-carboxy-methyleneaminooxy]-2-methyl-propionic acid ester in the presence of a carboxyl activating agent to provide the corresponding aztreonam sulfonyloxy organyl ester salt having the structure of Formula (1a), wherein, the organyl 3-amino-2-methyl-4-oxoazetidine-1-sulfonate salt has the structure of Formula (5a):

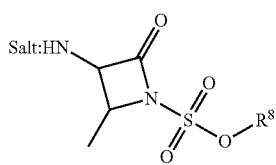

wherein,
$R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; and the 2-[(2-amino-thiazol-4-yl)-carboxy-methyleneaminooxy]-2-methyl-propionic acid ester has the structure of Formula (7):

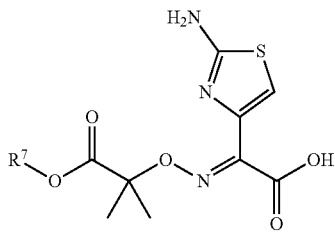

wherein,
$R^7$ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 32. The method of aspect 31, wherein the carboxyl activating agent is selected from N-(3-dimethylaminopropyl)-N'-ethylcarbodiimide hydrochloride (EDCI), 1-[bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), N,N,N',N'-tetramethyl-O-(benzotriazol-1-yl)uronium tetrafluoroborate (TBTU), 1-propanephosphonic anhydride solution, 2,4,6-tripropyl-1,3,5,2,4,6-trioxatriphosphorinane-2,4,6-trioxide (T3P), or a combination of any of the foregoing.

Aspect 33. The method of any one of aspects 31 to 32, wherein the pharmaceutically acceptable salt comprises the methanesulfonic acid salt, the triethylamine salt, the trifluoroacetic acid salt, or a combination of any of the foregoing.

Aspect 34. The method of any one of aspects 31 to 33, wherein $R^8$ is a neopentyl group having the structure of Formula (2):

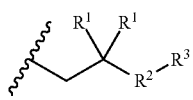

wherein,
each $R^1$ is independently $C_{1-6}$ alkyl, or each R and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—R⁴, —S—R⁴, —NH—R⁴, —CH(—NH₂)(—R⁴), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, R⁴ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

Aspect 35. The method of any one of aspects 31 to 34, further comprising (b) treating the tert-butoxy protected ester salt with an acid to provide the corresponding aztreonam sulfonyloxy organyl ester salt having the structure of Formula (1a):

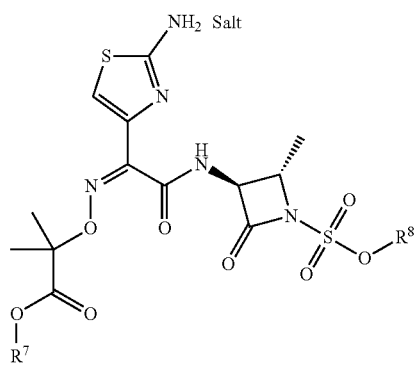

(1a)

Aspect 36. The method of any one of aspects 31 and 35, wherein reacting comprises reacting at a temperature from −10° C. to 10° C.

Aspect 37. A method of synthesizing an aztreonam derivative of Formula (1a), comprising:

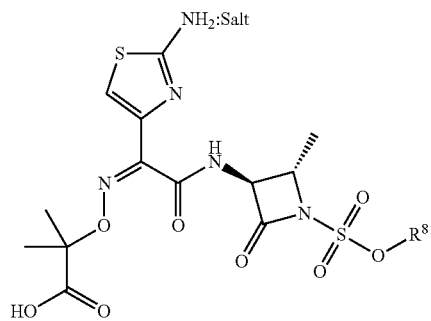

(1a)

or a pharmaceutically acceptable salt thereof, wherein,
R⁷ is selected from $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and R⁸ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; and (a) reacting an organyl 3-amino-2-methyl-4-oxoazetidine-1-sulfonate salt with a 2-[(2-amino-thiazol-4-yl)-carboxy-methyleneaminooxy]-2-methyl-propionic acid tert-butyl ester in the presence of a carboxyl coupling agent to provide the corresponding tert-butoxy protected salt; and (b) treating the tert-butoxy protected salt with an acid to provide the corresponding aztreonam sulfonyloxy organyl ester salt, wherein, the organyl 3-amino-2-methyl-4-oxoazetidine-1-sulfonate salt has the structure of Formula (5a):

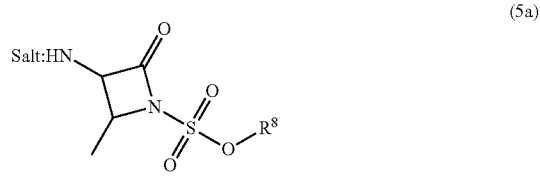

(5a)

wherein,
R⁸ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; and the 2-[(2-amino-thiazol-4-yl)-carboxy-methyleneaminooxy]-2-methyl-propionic acid tert-butyl ester (7a) has the structure of Formula (7a):

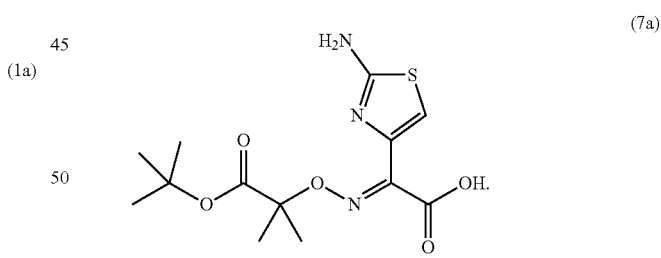

(7a)

Aspect 38. The method of aspect 37, wherein the carboxyl activating agent is selected from N-(3-dimethylaminopropyl)-N'-ethylcarbodiimide hydrochloride (EDCI), 1-[bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), N,N,N',N'-tetramethyl-O-(benzotriazol-1-yl)uronium tetrafluoroborate (TBTU), 1-propanephosphonic anhydride solution, 2,4,6-tripropyl-1,3,5,2,4,6-trioxatriphosphorinane-2,4,6-trioxide (T3P), or a combination of any of the foregoing.

Aspect 39. The method of any one of aspects 37 to 38, wherein the pharmaceutically acceptable salt comprises the methanesulfonic acid salt, the triethylamine salt, the trifluoroacetic acid salt, or a combination of any of the foregoing.

Aspect 40. The method of any one of aspects 25 and 37, wherein (a) reacting comprises reacting at a temperature from 20° C. to 30° C.

Aspect 41. The method of any one of aspects 25 and 37, wherein treating the tert-butoxy protected aztreonam salt comprises treating at a temperature from 20° C. to 30° C.

Aspect 42. The method of any one of aspects 25 and 37, wherein the organyl 3-amino-2-methyl-4-oxoazetidine-1-sulfonate methanesulfonic acid salt (5a) is prepared by the method of any one of aspects 1 to 10.

Aspect 43. The method of any one of aspects 25 and 37, wherein the organyl 3-amino-2-methyl-4-oxoazetidine-1-sulfonate methanesulfonic acid salt (5a) comprises the compound of any one of aspects 10 to 13.

Aspect 44. The method of any one of aspects 25 and 37, wherein the organyl 3-amino-2-methyl-4-oxoazetidine-1-sulfonate methanesulfonic acid salt (5a) is prepared by the method of any one of aspects 14 to 19.

Aspect 45. The method of any one of aspects 25 and 37, wherein the organyl 3-amino-2-methyl-4-oxoazetidine-1-sulfonate methanesulfonic acid salt (5a) comprises the compound of any one of 21 to 24.

Aspect 46. The method of any one of aspects 25 and 37, wherein the 2-[(2-amino-thiazol-4-yl)-carboxy-methyleneaminooxy]-2-methyl-propionic acid ester (7) is prepared by the method of any one of aspects 25 to 29.

Aspect 47. The method of any one of aspects 25 and 37, wherein the 2-[(2-amino-thiazol-4-yl)-carboxy-methyleneaminooxy]-2-methyl-propionic acid ester (7) comprises the compound of aspect 30.

Aspect 48. The method of any one of aspects 25 and 37, wherein the aztreonam sulfonyloxy organyl ester salt has the structure of Formula (1b)

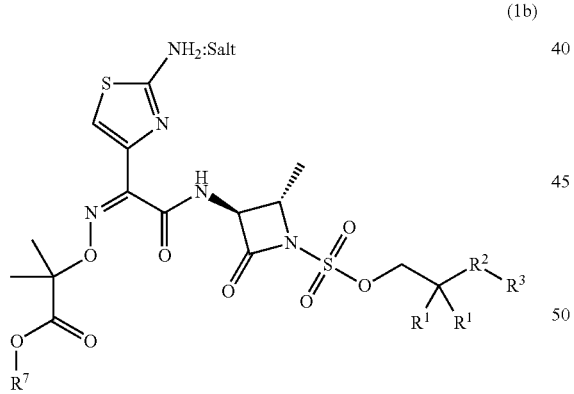

(1b)

wherein,
each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;

$R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein, $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl; and $R^7$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl.

Aspect 49. An aztreonam derivative synthesized using the method of any one of aspects 25 to 48.

Aspect 50. The aztreonam derivative of aspect 49, wherein the aztreonam derivative has the structure of Formula (1a)

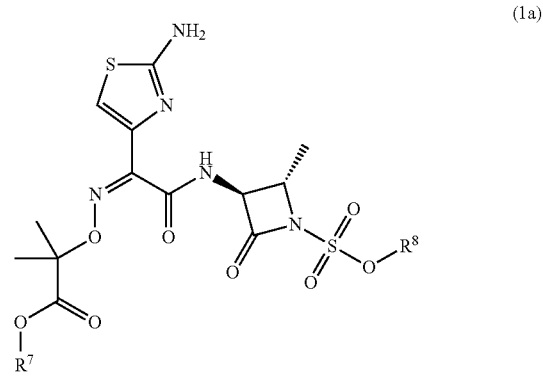

(1a)

or a pharmaceutically acceptable salt thereof, wherein,
$R^7$ is selected from hydrogen, $C_{1-6}$ alkyl, $C_{5-8}$ cycloalkyl, $C_{6-12}$ cycloalkylalkyl, $C_{2-6}$ heteroalkyl, $C_{5-8}$ heterocycloalkyl, $C_{6-12}$ heterocycloalkylalkyl, substituted $C_{1-6}$ alkyl, substituted $C_{5-8}$ cycloalkyl, substituted $C_{6-12}$ cycloalkylalkyl, substituted $C_{2-6}$ heteroalkyl, substituted $C_{5-8}$ heterocycloalkyl, and substituted $C_{6-12}$ heterocycloalkylalkyl; and $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl.

Aspect 51. The aztreonam derivative of aspect 50, wherein $R^8$ has the structure of Formula (2):

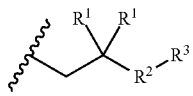
(2)

wherein,
- each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;
- $R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and
- $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl,
wherein,
- $R^4$ is selected from hydrogen, $C_{1-3}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

EXAMPLES

The following examples describe in detail the synthesis of compounds of Formula (1). It will be apparent to those skilled in the art that many modifications, both to materials and methods, may be practiced without departing from the scope of the disclosure.

General Procedures

All reagents were purchased from commercial suppliers and used without further purification. All solvents were reagent, or HPLC grade. Analytical TLC was performed on silica gel 60 F254 plates and visualized by UV, by staining with KMnO$_4$ dip, or by phosphomolybdic acid in EtOH dip. Flash chromatography was carried out using an automated system with pre-packed silica columns. Yields refer to isolated yields of pure compounds. $^1$H-NMR and $^{13}$C-NMR spectra were recorded on a 300 MHz spectrometer at 25° C. Chemical shifts are reported in parts per million (ppm) relative to deuterated solvent, or a TMS internal standard. Multiplicities are reported as follows: s=singlet; d=doublet, t=triplet; m=multiplet; br=broad. High resolution mass spectra were recorded using a time of flight mass spectrometer.

Example 1

Synthesis of 2-tert-butoxycarbonylamino-3-hydroxy-butyric acid benzyl ester (1)

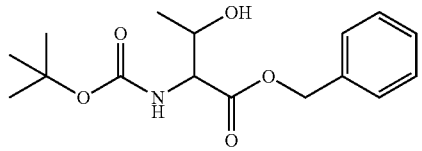 [SMILES: CC(O)C(NC(=O)OC(C)(C)C)C(=O)OCc1ccccc1]

To a solution of Boc-L-threonine (15.0 g, 68.4 mmol) in DMF (465 mL) at 0° C. were added NaHCO$_3$ (16.0 g, 190.2 mmol) and benzyl bromide (40.6 mL, 342.1 mmol). After stirring overnight at 25° C., water was added and the mixture was extracted with EtOAc. The organic layers were washed with water and brine, and concentrated. The dried residue was purified with flash chromatography over silica gel (0-60%, EtOAc/hexanes) to obtain compound (1) (18.8 g, 89% yield) as a colorless oil. $^1$H NMR (300 MHz, CDCl$_3$) δ 7.43-7.29 (m, 5H), 5.35 (d, J=9.2 Hz, 1H), 5.32-5.11 (m, 2H), 4.29 (d, J=9.4 Hz, 2H), 1.44 (s, 9H), 1.31-1.19 (m, 3H). LC-MS: 310 [M+H]$^+$.

Example 2

Synthesis of 3-azido-2-tert-butoxycarbonylamino-butyric acid benzyl ester (2)

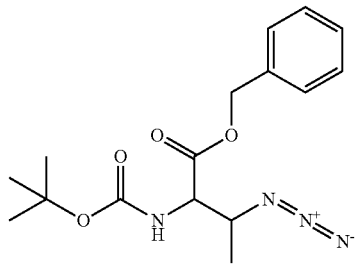 [SMILES: CC(N=[N+]=[N-])C(NC(=O)OC(C)(C)C)C(=O)OCc1ccccc1]

Step 1: Benzyl 2-((tert-butoxycarbonyl)amino)-3-(((trifluoromethyl)sulfonyl)oxy)butanoate (2a)

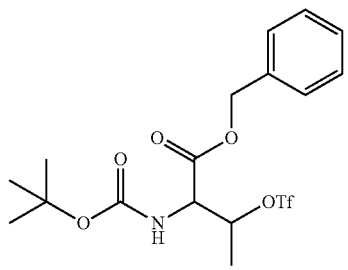 [SMILES: CC(OS(=O)(=O)C(F)(F)F)C(NC(=O)OC(C)(C)C)C(=O)OCc1ccccc1]

To a solution of 2-tert-butoxycarbonylamino-3-hydroxybutyric acid benzyl ester (1) (9.28 g, 30.0 mmol, 1.0 eq) in anhydrous dichloromethane (DCM) (150 mL) at −78° C. were added trifluoromethanesulfonic anhydride (Tf$_2$O) (6.06 mL, 36.0 mmol, 1.2 eq) dropwise and 2,6-lutidine (4.54 mL, 39.0 mL, 1.3 eq), respectively. The mixture was stirred at −78° C. for 1.5 h to provide the trifluoro ester (2a).

Step 2: Synthesis of 3-azido-2-tert-butoxycarbonylamino-butyric acid benzyl ester (2)

Bu$_4$NN$_3$ (21.3 g, 75.0 mmol, 2.5 eq) in anhydrous dichloromethane (30 mL) was added to the trifluoro acid ester (2a). The mixture was stirred at −78° C. for 1 h and the reaction was warmed to room temperature for 1.5 h. The reaction mixture was diluted with dichloromethane and washed with saturated sodium bicarbonate. The organic phase was separated, dried over sodium sulfate, and concentrated to dryness. The residue was purified by flash chromatography (silica, hexanes/EtOAc=4:1) to give the title compound (2) (8.82 g, 88% yield) as a colorless oil. $^1$H NMR (300 MHz, CDCl$_3$) δ 7.61 (s, 1H), 7.36 (d, J=2.6 Hz, 4H), 5.29 (s, 1H), 5.29-5.11 (m, 2H), 4.46 (d, J=8.5 Hz, 1H), 3.84 (d, J=8.1 Hz, 1H), 1.45 (d, J=0.8 Hz, 9H), 1.34-1.16 (m, 3H); $^{13}$C NMR (75 MHz, CDCl$_3$) δ: 169.5, 155.0, 134.9, 128.7, 128.6, 128.5, 80.5, 67.6, 58.8, 57.5, 28.3, 28.3, 15.4.

Example 3

Synthesis of 3-amino-2-tert-butoxycarbonylamino-butyric acid benzyl ester (3)

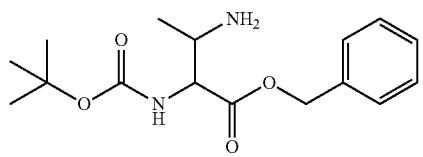 [SMILES: CC(N)C(NC(=O)OC(C)(C)C)C(=O)OCc1ccccc1]

To a solution of 3-azido-2-tert-butoxycarbonylamino-butyric acid benzyl ester (2) (11.3 g, 33.8 mmol, 1.0 eq) in tetrahydrofuran (THF) (40 mL) was added trimethylphosphine (1.0 M in THF, 67.6 mmol, 67.6 mmol, 2.0 eq) at 0° C. The mixture was warmed to 25° C. for 2 h. Water (4 mL) was added to the reaction and the mixture was stirred at 25° C. for 2 h. The reaction mixture was concentrated to dryness. The residue was purified by flash chromatography (silica, EtOAc) to give the title compound (3) (8.05 g, 77% yield) as a colorless oil. $^1$H NMR (300 MHz, CDCl$_3$) δ 7.36 (t, J=1.5 Hz, 5H), 7.26 (s, 1H), 5.30 (m, 1H), 5.28-5.10 (m, 2H), 4.32 (s, 1H), 3.30 (s, 1H), 1.47 (s, 9H), 1.02 (d, J=6.7 Hz, 3H). LC-MS: 309 [M+H]$^+$ Example 4

Synthesis of 2-tert-butoxycarbonylamino-3-(2-ethoxycarbonyl-2-methyl-propoxysulfonyl amino)-butyric acid benzyl ester (4)

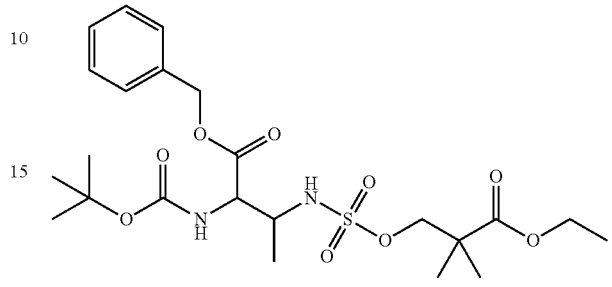

To a solution of 3-amino-2-tert-butoxycarbonylamino-butyric acid benzyl ester (3) (4.09 g, 13.3 mmol, 1.0 eq) in 1,2-dichloroethane (DCE) (50 mL) was added a saturated aqueous solution of sodium bicarbonate (50 mL). To the mixture was added ethyl 3-((chlorosulfonyl)oxy)-2,2-dimethylpropanoate (6.49 g, 26.2 mmol, 2.0 eq) and the mixture was stirred rapidly at 45° C. for 20 h. The reaction mixture was cooled to 25° C. and the layers were separated. The organic layer was dried with anhydrous sodium sulfate and concentrated to dryness. The residue was purified by flash column chromatography (silica, hexanes/EtOAc=3:1) to give the title compound (4) (5.07 g, 74% yield) as a white solid. $^1$H NMR (300 MHz, CDCl$_3$) δ 7.37-7.27 (m, 5H), 6.03-5.96 (m, 1H), 5.52-5.46 (m, 1H), 5.18 (s, 2H), 4.57-4.52 (m, 1H), 4.18-4.07 (m, 4H), 4.01-3.95 (m, 1H), 1.42 (s, 9H), 1.33-1.22 (m, 9H), 1.16 (d, J=6.7 Hz, 3H). $^{13}$C NMR (75 MHz, CDCl$_3$) δ 174.8, 169.6, 134.7, 128.8, 128.7, 128.5, 81.0, 75.3, 67.9, 61.0, 57.7, 53.4, 52.8, 42.6, 28.2, 22.1, 16.6, 14.1.

Example 5

Synthesis of 2-tert-butoxycarbonylamino-3-(2-ethoxycarbonyl-2-methyl-propoxysulfonyl-amino)-butyric acid (5)

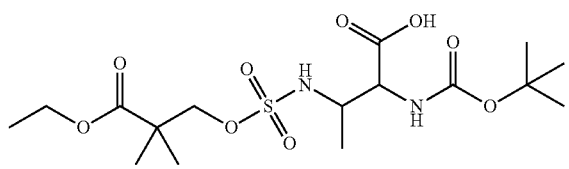 [SMILES: CCOC(=O)C(C)(C)COS(=O)(=O)NC(C)C(NC(=O)OC(C)(C)C)C(=O)O]

To a solution of 2-tert-butoxycarbonylamino-3-(2-ethoxycarbonyl-2-methyl-propoxysulfonyl amino)-butyric acid benzyl ester (4) (4.20 g, 8.14 mmol, 1.0 eq) in ethyl acetate (50 mL) was added Pd/C (420 mg). The suspension was degassed 3 times and refilled with hydrogen. The mixture was stirred at room temperature for 2 h. The reaction mixture was filtered through a pad of Celite®. The filtrate was concentrated to dryness, affording the title compound (5) (3.47 g, 100% yield). $^1$H NMR (300 MHz, CDCl$_3$) δ 6.23-1.18 (m, 1H), 5.68-5.63 (m, 1H), 4.45-4.40 (m, 1H), 4.19-4.05 (m, 4H), 3.97-3.89 (m, 1H), 1.50 (s, 9H), 1.39-

1.22 (m, 12H). ¹³C NMR (75 MHz, acetone-d6) δ 174.3, 170.8, 156.1, 79.0, 74.8, 60.5, 59.8, 57.8, 44.2, 27.6, 21.5, 21.4, 21.4, 16.1, 13.6, 13.6. LC-MS: 427 [M+H]+.

Example 6

Synthesis of 3-(3-tert-butoxycarbonylamino-2-methyl-4-oxo-azetidine-1-sulfonyloxy)-2,2-dimethyl-propionic acid ethyl ester (6)

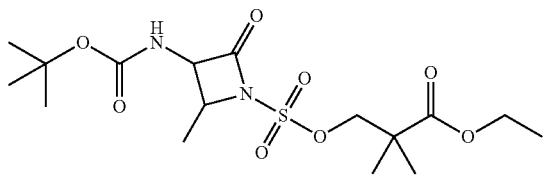 [SMILES: CCOC(=O)C(C)(C)COS(=O)(=O)N1C(=O)C(NC(=O)OC(C)(C)C)C1C]

To a solution of 2-tert-butoxycarbonylamino-3-(2-ethoxycarbonyl-2-methyl-propoxysulfonyl-amino)-butyric acid (5) (3.47 g, 8.14 mmol, 1.0 eq) in acetonitrile (240 mL) was added N,N,N',N'-tetramethylchloroformamidinium hexafluorophosphate (TCFH, 3.43 g, 12.2 mmol, 1.5 eq) and triethylamine (TEA) (2.95 mL, 21.2 mmol, 2.6 eq) at 0° C. The mixture was stirred at 0° C. for 10 min and concentrated to dryness. The residue was diluted to ethyl acetate and washed with water and brine. The organic phase was separated, dried, and concentrated to dryness. The residue was purified by flash column chromatography (silica, hexanes/EtOAc=3:2) to give the title compound (6) (2.97 g, 89% yield). ¹H NMR (300 MHz, acetone-d₆) δ 7.05-6.97 (m, 1H), 4.56-4.51 (m, 1H), 4.49-4.40 (m, 3H), 4.17 (dd, J=7.5, 6.9 Hz, 2H), 1.55 (d, J=6.6 Hz, 3H), 1.42 (s, 9H), 1.33-1.22 (m, 9H). ¹³C NMR (75 MHz, acetone-d₆) δ 174.1, 164.1, 156.1, 79.9, 76.9, 64.6, 60.6, 59.1, 42.4, 27.5, 21.3, 21.1, 16.7, 13.5. LC-MS: 409 [M+H]+. ¹H NMR (300 MHz, CDCl₃) δ 5.82 (d, J=8.7 Hz, 1H), 4.54 (d, J=10.2 Hz, 1H), 4.45 (dd, J=8.9 Hz, 3.5 Hz, 1H), 4.24-4.11 (m, 4H), 1.58 (d, J=5.7 Hz, 3H), 1.42 (s, 9H), 1.29-1.24 (m, 9H). ¹³C NMR (75 MHz, CDCl₃) δ 175.6, 165.2, 154.6, 81.0, 77.2, 64.5, 61.6, 60.7, 42.8, 28.3, 22.1, 21.8, 18.0, 14.1.

Example 7

Synthesis of 3-(3-amino-2-methyl-4-oxo-azetidine-1-sulfonyloxy)-2,2-dimethyl-propionic acid ethyl ester methanesulfonic acid Salt (7)

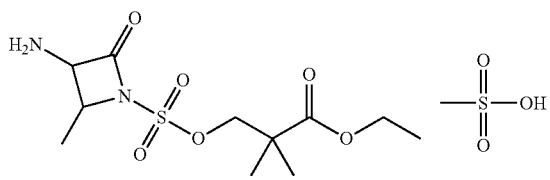

3-(3-tert-Butoxycarbonylamino-2-methyl-4-oxo-azetidine-1-sulfonyloxy)-2,2-dimethyl-propionic acid ethyl ester (6) (1.30 g, 3.44 mmol, 1.0 eq) in dichloromethane (15 mL) was treated with methanesulfonic acid (MSA) (330 mg, 3.44 mmol, 1.0 eq) at 25° C. for 20 h. The reaction mixture was concentrated to dryness. The residue (7) was used for next step without further purification. LC-MS: 309 [M+H]+.

Example 8

Synthesis of tetrabutylammonium (2S,3S)-3-(((benzyloxy)carbonyl)amino)-2-methyl-4-oxoazetidine-1-sulfonate (8)

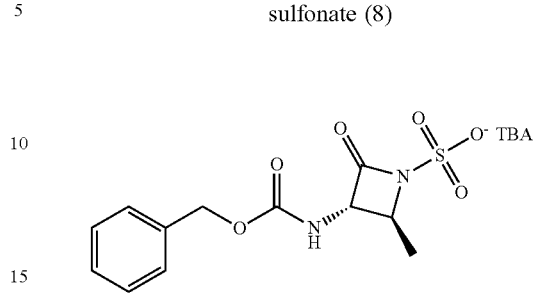

To a solution of (2S,3S)-3-amino-2-methyl-4-oxo-1-azetidinesulfonic acid (55.0 g, 305.2 mmol) in a mixture of EtOH (600 mL) and H₂O (300 mL) was added Et₃N (159.5 mL, 915.7 mmol) followed by benzyloxycarbonyl N-succinimide (83.7 g, 335.8 mmol). The reaction mixture was stirred at 25° C. for 16 hours. Ethanol was removed under vacuum and the residue was diluted with H₂O (200 mL). The aqueous layer was extracted with EtOAc (2×100 mL). The EtOAc was discarded. Tetrabutyl ammonium hydroxide (207.9 g, 320.5 mmol) as 40% w/v in H₂O was added and the resulting aqueous layer was extracted with CHCl₃ (5×150 mL). The organic extract was dried (MgSO₄) and concentered to give the product (8) (160 g, 94% yield) as a solid. ¹H NMR (300 MHz, CDCl₃) δ 7.38-7.31 (m, 5H), 4.31 (d, J=7.2 Hz, 1H), 6.01 (s, 2H) 5.50 (s, 1H), 5.12 (s, 2H), 4.31 (d, J=7.2 Hz, 1H), 3.28-3.22 (m, 8H), 1.62-1.59 (m, 8H), 1.46-1.39 (m, 11H), 1.01-0.96 (m, 12H). ¹³C NMR (75 MHz, CDCl₃) δ 162.9, 155.7, 136.1, 135.7, 128.5, 128.3, 128.2, 128.0, 67.0, 62.7, 59.2, 58.5, 23.9, 19.6, 18.2, 13.7.

Example 9

Synthesis of benzyl ((2S,3S)-2-methyl-4-oxoazetidin-3-yl)carbamate (9)

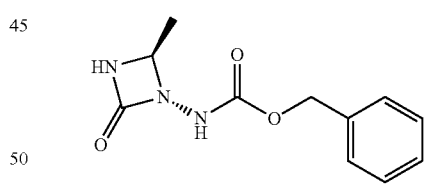

(2S,3S)-3-(((Benzyloxy)carbonyl)amino)-2-methyl-4-oxoazetidine-1-sulfonate tetrabutylamm-onium salt (8) (131 g, 235.7 mmol) was dissolved in dry THF (2.8 L) and H₂O (12.8 mL, 710.5 mmol), and the resulting solution cooled in an ice bath. Trifluoroacetic acid (280 mL) was added dropwise, and the mixture was stirred at 25° C. for 1.5 h. The reaction mixture was concentrated under vacuum, and the residue was diluted with DCM (1.5 L), then chilled with an ice bath. Aqueous NaOH solution (10%) was added slowly to pH 8-9. The organic layer was washed with H₂O, dried (MgSO₄), and concentrated under vacuum. The residue was purified by column chromatography on silica gel using EtOAc/hexanes (1:9 to 1:0) to give the product (9) (30.1 g, 54% yield) as a solid. ¹H NMR (300 MHz, CDCl₃) δ 7.38-7.31 (m, 5H), 6.01 (s, 1H) 5.50 (s, 1H), 5.12 (s, 2H), 4.31 (d, J=7.2 Hz, 1H), 3.74-3.71 (m, 1H), 1.42 (d, J=6 Hz, 3H). $^{13}$C NMR (75 MHz, CDCl$_3$) δ 167.4, 155.9, 136.1, 67.2, 64.7, 54.0, 19.2. LC-MS: m/z=280.1 [M+HCO$_2$H]$^+$

Example 10

Synthesis of (2S,3R)-3-amino-2-(((benzyloxy)carbonyl)amino)butanoic acid HCl Salt (10)

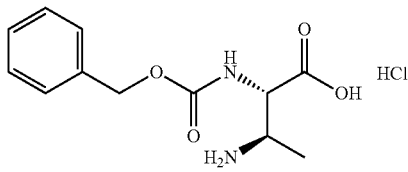 [SMILES: C[C@@H](N)[C@H](NC(=O)OCc1ccccc1)C(=O)O ; Cl]

Benzyl (((2S,3S)-2-methyl-4-oxoazetidin-3-yl)carbamate azetidin-3-yl)carbamate (9) (6.0 g, 25.6 mmol) was dissolved in neat formic acid (50 mL). H$_2$O (50 mL) was added and the resulting mixture was stirred at 25° C. for 18 h. The mixture was concentrated under vacuum to give (2S,3R)-3-amino-2-(((benzyloxy)carbonyl)amino)butanoic formic acid salt as a solid. The formic acid salt was dissolved in MeCN (10 mL). 4N HCl in dioxane (15 mL) was added and the resulting solution was concentrated to dryness under vacuum. Another portion of 4N HCl in dioxane (15 mL) was added and the mixture was stirred for 1 h at 25° C. to provide a solid. Et$_2$O (50 mL) was added and the solid was collected by filtration to give the product (10) (6.8 g, 92% yield). $^1$H NMR (300 MHz, CD$_3$OD) δ 7.59 (d, J=8.7 Hz, 1H), 7.41-7.30 (m, 5H), 5.15 (q, J=21 Hz, 2H), 4.68-4.64 (m, 1H), 3.88-3.84 (m, 1H), 1.25 (d, J=7.2 Hz, 3H). $^{13}$C NMR (75 MHz, CD$_3$OD) δ 171.4, 159.1, 137.8, 129.5, 129.1, 129.0, 68.3, 56.9, 49.9, 14.1. LC-MS: m/z=253.3 [M+H]+.

Example 11

Synthesis of tert-butyl (2S,3R)-3-amino-2-(((benzyloxy)carbonyl)-amino)butanoate (11)

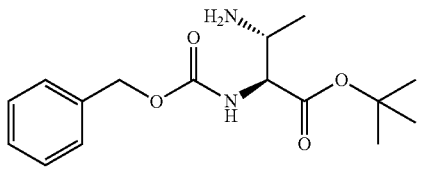 [SMILES: C[C@@H](N)[C@H](NC(=O)OCc1ccccc1)C(=O)OC(C)(C)C]

Method 1.

To a solution of (2S,3S)-3-amino-2-(((benzyloxy)carbonyl)amino)butanoic acid hydrochloride (10) (4.5 g, 15.5 mmol) in 1,4-dioxane (36 mL) at −10° C. was added dropwise concentrated H$_2$SO$_4$ (4.9 ml, 92.8 mmol). The reaction mixture was placed in a dry ice-acetone bath and iso-butylene (36 g, 622.5 mmol) was added. The reaction vessel was capped, and the reaction mixture was stirred at 25° C. for 48 h. Iso-butylene was removed by passing nitrogen through the solution, and the mixture was poured into a mixture of H$_2$O (150 mL) and saturated aqueous Na$_2$CO$_3$ (50 mL). The aqueous layer was extracted with EtOAc (3×100 mL), and the combined organic layers were washed with brine (50 mL), dried (MgSO$_4$) and concentered under vacuum. The residue was purified by column chromatography on silica gel using DCM/MeOH (1:0 to 9:1) to the product (11) (2.83 g, 59% yield) as a clear oil. $^1$H NMR (300 MHz, CDCl$_3$) δ 7.37-7.31 (m, 5H), 5.52 (d, J=6.9 Hz, 1H), 5.11 (s, 2H), 4.28-4.24 (m, 1H), 3.33-3.30 (m, 1H), 1.46 (s, 9H), 1.05 (d, J=6.9 Hz, 3H). $^{13}$C NMR (75 MHz, CDCl$_3$) δ 170.0, 156.7, 136.3, 128.6, 128.3, 128.2, 82.5, 67.1, 60.5, 49.5, 28.1, 18.9. LC-MS: m/z=309.6 [M+H]+.

Method 2.

A reactor equipped with a mechanical stirrer was prepared and flushed with Argon. Under argon, (2S,3S)-3-amino-2-(((benzyloxy)carbonyl)amino)butanoic acid hydrochloride (10) (28.77 g, 0.10 mol) and tert-butyl acetate (288 mL, 2.15 mol, 21.5 eq) were added to the reactor, stirred mechanically, and cooled in an ice bath. H$_2$SO$_4$ (12.1 g, 0.12 mol, 1.20 eq) was dripped in over 10 minutes. The resulting slurry was immersed in a 20° C. bath for 10 minutes, then AcOH (72 mL) was dripped in over 20 min. After 17 h, the homogeneous reaction solution was cooled with an ice bath while dripping in a solution of NaOH (96.8 g) in H$_2$O (450 mL). The resulting solution was extracted with EtOAc (600 mL). The extract was washed with brine, dried (Na$_2$SO$_4$), and concentrated to give the product (11) (14.95 g). $^1$H NMR (300 MHz, CDCl$_3$) δ 7.37-7.31 (m, 5H), 5.52 (d, J=6.9 Hz, 1H), 5.11 (s, 2H), 4.28-4.24 (m, 1H), 3.33-3.30 (m, 1H), 1.46 (s, 9H), 1.05 (d, J=6.9 Hz, 3H). $^{13}$C NMR (75 MHz, CDCl$_3$) δ 170.0, 156.7, 136.3, 128.6, 128.3, 128.2, 82.5, 67.1, 60.5, 49.5, 28.1, 18.9. LC-MS: m/z=309.6 [M+H]+.

Example 12

Synthesis of tert-butyl (2S,3S)-2-(((benzyloxy)carbonyl)amino)-3-(((3-ethoxy-2,2-dimethyl-3-oxopropox sulfonylamino butanoate 12

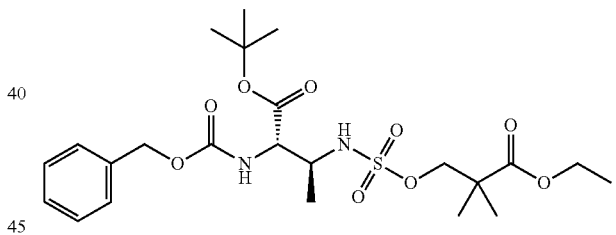

(2S,3S)-tert-Butyl 3-amino-2-(((benzyloxy)carbonyl)amino)butanoate (11) (8.90 g, 28.9 mmol) was dissolved in 1,2-dichloroethane (150 mL) and combined with ethyl 3-((chlorosulfonyl)oxy)-2,2-dimethylpropanoate (10.40 g, 37.4 mmol, 1.3 eq). The solution was combined in a round-bottomed flask with 200 mL of saturated aq. sodium bicarbonate. A stir bar was added, and the flask sealed with a rubber septum into which a needle connected to a balloon containing argon was introduced. The mixture was heated in a 40° C. and stirred rapidly for 46 h. Stirring was stopped, the phases were partitioned, and the aq. phase was extracted with DCM (50 mL). The organic phases were combined, dried with sodium sulfate, and concentrated to an oil (17.0 g). The oil was purified by column chromatography on silica gel (330-g column) using Et$_2$O/Hexanes (1:9 to 2:3) as eluent while monitoring for absorbances at 210 nM, to give pure product (6.40 g), together with impure fractions (3.15 g). A significant amount of non-transformed starting material remained on top of the column. This was recovered by washing the column with MeOH/DCM (1:9) as eluent to give starting material (2.27 g). The impure fractions (3.15 g)

from the column were re-purified to provide additional pure product (12) (2.17 g). The yield of this reaction is 77%. $^1$H NMR (300 MHz, CDCl$_3$) δ 7.38-7.33 (m, 5H), 6.02 (d, J=7.5 Hz, 1H), 5.73 (d, J=5.7 Hz, 1H), 5.13 (s, 2H), 4.50 (dd, J=7.1, 5.7 Hz, 1H), 4.20-4.11 (m, 4H), 3.99-3.95 (m, 1H), 1.47 (s, 9H), 1.27-1.23 (m, 9H), 1.17 (d, J=6.6 Hz, 3H). $^{13}$C NMR (75 MHz, CDCl$_3$) δ 174.9, 168.5, 157.3, 135.8, 128.7, 128.5, 128.4, 84.0, 75.4, 67.8, 61.2, 58.5, 53.0, 42.8, 28.0, 22.2, 16.5, 14.2. LC-MS: 517.0 [M+H]+.

Example 13

Synthesis of 3-(3-tert-butoxycarbonylamino-2-methyl-4-oxo-azetidine-1-sulfonyloxy)-2,2-dimethyl-propionic acid ethyl ester (13)

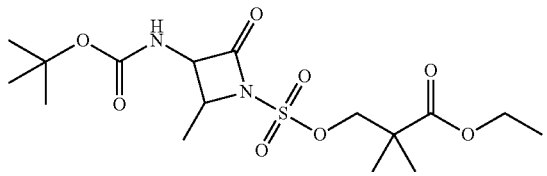 [SMILES: CCOC(=O)C(C)(C)COS(=O)(=O)N1C(=O)C(NC(=O)OC(C)(C)C)C1C]

Into a reactor equipped with a bubbler and an inlet of argon was added tert-butyl (2S,3S)-2-(((benzyloxy)carbonyl)amino)-3-(((3-ethoxy-2,2-dimethyl-3-oxopropoxy)sulfonyl)amino)butanoate (12) (15.29 g, 30.0 mmol). An argon atmosphere was established and anhydrous MeCN (460 mL) was added, stirring to dissolve. The resulting solution was cooled in an ice bath while 4 M HCl in 1,4-dioxane (153 mL, 612 mmol, 20.7 eq) was added dropwise over 20 min. The reaction mixture was heated at 40° C. and stirred for 2 h while passing a constant stream of argon through the reactor for the duration of the reaction. The solution was concentrated on a rotary evaporator then re-concentrated with MeCN (150 mL) and re-evaporated. This procedure was repeated 4 time. The crude, de-tert-butylated product (13a) (15.51 g) was used in the next step without further purification. $^1$H NMR (300 MHz, CDCl$_3$) δ 7.38-7.32 (m, 5H), 6.07 (d, J=7.5 Hz, 1H), 5.91 (d, J=6.6 Hz, 1H), 5.14 (s, 2H), 4.63-4.61 (m, 1H), 4.24-4.05 (m, 4H), 3.93 (m, 1H), 1.30-1.24 (m, 12H). LCMS: 460.97 [M+H]+.

The crude de-tert-butylated product (13a) (10.38 g used in this step) was combined with 10% palladium-on-carbon (50% w/w with H$_2$O) (2.33 g) and MeOH (120 mL) in a round-bottomed flask equipped with a stir bar. The mixture was placed under an atmosphere of hydrogen and the solution stirred for 1 h. The mixture was filtered and the filter cake was washed with MeOH (80 mL). The filtrate was concentrated under vacuum and dried further in a vacuum oven set to 60° C. to give a crude amino-acid product (13) (7.21 g) that was used without further purification. $^1$H NMR (300 MHz, d$_6$-DMSO) δ 7.97 (s, 3H), 4.12-3.97 (m, 4H), 3.87-3.84 (m, 1H), 3.45 (d, J=1.8 Hz, 1H), 1.18-1.14 (m, 9H), 1.07 (d, J=6.9 Hz, 3H). $^{13}$C NMR (75 MHz, d$_6$-DMSO) δ 174.3, 169.0, 74.5, 60.6, 58.4, 50.3, 42.2, 21.8, 21.7, 14.7, 14.0. LC-MS (ESI): 327.2 [M+H]+.

This crude amino-acid product (13) (7.38 g) was combined with di-tert-butyl dicarbonate and tetrahydrofuran (120 mL). To this stirred solution was added Et$_3$N (7.9 mL) and a balloon of argon was placed above the reaction. The mixture was stirred at 40° C. for 4 h. The mixture was concentrated under vacuum, then mixed with H$_2$O (150 mL) and extracted with hexanes (150 mL). The aqueous phase was combined with EtOAc (150 mL) and stirred vigorously while 7.90 g of citric acid was added in one portion. The aqueous and organic layers were partitioned, and the aqueous phase was extracted with EtOAc (150 mL). The combined organic layers were dried (Na$_2$SO$_4$), filtered and concentrated under vacuum. The product was dried further in a vacuum oven (set at 55° C.) to give the product (9.0 g) that was used in the next step without further purification. LC-MS: 426.7 [M+H]+. The crude Boc-amino acid from above (5.18 g of the sample) was dissolved in anhydrous MeCN (300 mL) and placed under an atmosphere of argon. The solution was stirred and cooled in an ice-water bath for 5 min, then N,N,N',N'-tetramethylchloroformamidinium hexafluorophosphate, TCFH, 4.77 g, (17.0 mmol) was added in one portion. The mixture was stirred in the ice bath for 30 min, then at 25° C. for an additional 15 min. The mixture was concentrated under vacuum. The residue was mixed with H$_2$O (40 mL) and extracted with EtOAc (3×50 mL). The combined organic extracts were dried (Na$_2$SO$_4$), filtered, and concentrated under vacuum. This material was purified by column chromatography on silica gel (120 g column) using EtOAc/hexanes (0:1 to 1:0) as eluent to give the product (13) (3.78 g, 79% yield over 4 steps) after drying in a vacuum oven (set at 55° C.). $^1$H NMR (300 MHz, d$_6$-DMSO) δ 7.97 (s, 3H), 4.12-3.97 (m, 4H), 3.87-3.84 (m, 1H), 3.45 (d, J=1.8 Hz, 1H), 1.18-1.14 (m, 9H), 1.07 (d, J=6.9 Hz, 3H). $^{13}$C NMR (75 MHz, d$_6$-DMSO) δ 174.3, 169.0, 74.5, 60.6, 58.4, 50.3, 42.2, 21.8, 21.7, 14.7, 14.0. LC-MS (ESI): 327.2 [M+H]+.

Example 14

Preparation of 2-[(2-amino-thiazol-4-yl)-(9H-fluoren-9-ylmethoxycarbonyl)-methyleneaminooxy]-2-methyl-propionic acid tert-butyl ester (14)

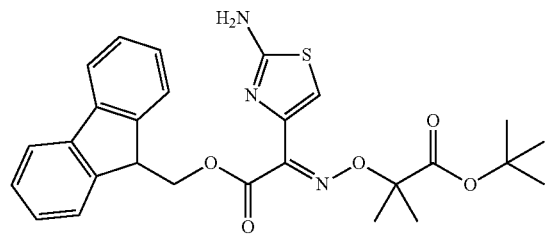 [SMILES: CC(C)(C)OC(=O)C(C)(C)O/N=C(/C(=O)OCC1c2ccccc2-c2ccccc21)c1csc(N)n1]

To a suspension of 2-[(2-amino-thiazol-4-yl)-carboxymethyleneaminooxy]-2-methyl-propionic acid tert-butyl ester (B) (19.1 g, 57.9 mmol, 1.0 eq) in dichloromethane (200 mL) was added (9H-fluoren-9-yl)-methanol (C) (9.91 g, 57.9 mmol, 1.0 eq), 1-ethyl-3-(3-dimethylaminopropyl)carbondiimide (EDCI) (16.6 g, 86.9 mmol, 1.5 eq) and pyridine (14.0 mL, 174 mmol, 3.0 eq). The clear solution was stirred at 25° C. as a solid started to form. After 2-3 h, the mixture was filtered and the solid was rinsed with DCM (30 mL), to provide the title compound (14) (27.3 g, 93% yield) as white solid. $^1$H NMR (300 MHz, CDCl$_3$) δ 7.78 (d, J=7.5 Hz, 2H), 7.72 (d, J=7.8 Hz, 2H), 7.38 (t, J=7.5 Hz, 2H), 7.35 (t, J=7.5 Hz, 2H), 6.93 (br. s, 2H), 6.41 (s, 1H), 4.62 (d, J=6.9 Hz, 2H), 4.33 (t, J=7.2 Hz, 1H), 1.58 (s, 6H), 1.56 (s, 9H). $^1$H NMR (300 MHz, d$_6$-DMSO), δ 7.88 (d, J=7.2 Hz, 2H), 7.73 (d, J=7.8 Hz, 2H), 7.41 (t, J=7.4 Hz, 2H), 7.33-7.30 (m, 4H), 6.55 (s, 1H), 4.64 (d, J=6.3 Hz, 2H), 4.32 (t, J=6.5 Hz, 1H), 1.35 (s, 15H). $^{13}$C NMR (75 MHz, d$_6$-DMSO), δ 172.1, 169.3, 162.9, 147.0, 143.8, 141.5, 141.2, 128.3, 127.6, 125.7, 120.7, 109.5, 82.9, 81.0, 67.0, 46.6, 28.0, 24.0. LC/MS: 508.0 [M+H]+

Example 15

Preparation of 2-{(9H-fluoren-9-ylmethoxycarbonyl)-[2-(2,2,2-trifluoro-acetylamino)-thiazol-4-yl]-methyleneaminooxy}-2-methyl-propionic acid TFA Salt (15)

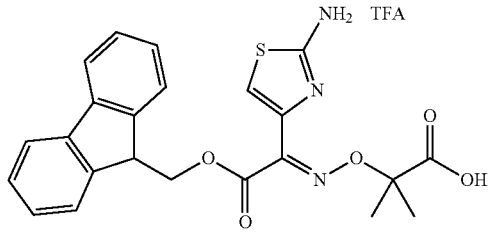 [SMILES: CC(C)(O/N=C(/C(=O)OCC1c2ccccc2-c2ccccc21)c1csc(N)n1)C(=O)O ; "TFA"]

A solution of 2-[(2-amino-thiazol-4-yl)-(9H-fluoren-9-ylmethoxycarbonyl)-methyleneaminooxy]-2-methyl-propionic acid tert-butyl ester (14) (27.3 g, 53.8 mmol) in trifluoroacetic acid (50 mL) was stirred at 25° C. for 2 h. The reaction mixture was concentrated to dryness. The residue was triturated with diethyl ether (200 mL) and filtered to afford the title compound (15) (29.3 g, 100% yield) as a white solid. $^1$H NMR (300 MHz, CDCl$_3$) δ 7.72 (d, J=7.5 Hz, 2H), 7.62 (d, J=7.5 Hz, 2H), 7.34 (t, J=7.5 Hz, 2H), 7.28 (t, J=7.5 Hz, 2H), 6.08 (s, 1H), 4.71 (d, J=6.6 Hz, 2H), 4.28 (t, J=6.6 Hz, 1H), 1.56 (s, 6H). $^1$H NMR (300 MHz, d$_6$-DMSO) δ 7.88 (d, J=7.5 Hz, 2H), 7.73 (d, J=7.5 Hz, 2H), 7.41 (t, J=7.4 Hz, 2H), 7.31 (t, J=7.4 Hz, 2H), 6.54 (s, 1H), 4.66 (d, J=6.6 Hz, 2H), 4.33 (t, J=6.5 Hz, 1H), 1.35 (s, 6H). $^{13}$C NMR (75 MHz, d$_6$-DMSO) δ 174.7, 169.5, 162.6, 146.2, 143.8, 141.2, 140.2, 128.3, 127.7, 125.7, 120.6, 110.3, 82.6, 67.1, 46.6, 24.1. LC/MS: 452.2 [M+H]$^+$

Example 16

Preparation of 2-[(2-amino-thiazol-4-yl)-(9H-fluoren-9-ylmethoxycarbonyl)-methyleneaminooxy]-2-methyl-propionic acid ethyl ester (16)

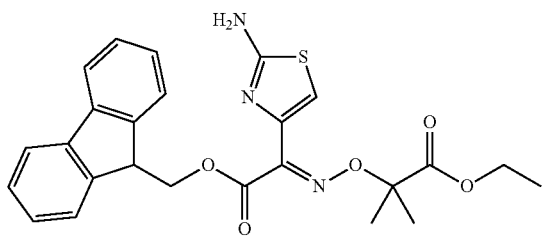 [SMILES: CCOC(=O)C(C)(C)O/N=C(/C(=O)OCC1c2ccccc2-c2ccccc21)c1csc(N)n1]

To a suspension of 2-{(9H-fluoren-9-ylmethoxycarbonyl)-[2-(2,2,2-trifluoro-acetylamino)-thiazol-4-yl]-methyleneaminooxy}-2-methyl-propionic acid TFA salt (15) (9.02 g, 16.0 mmol, 1.0 eq) in dichloromethane (200 mL) and ethanol (5 mL) at 0° C. was added EDCI (4.60 g, 24.0 mmol, 1.5 eq) and pyridine (6.47 mL, 80.0 mmol, 5.0 eq). The clear solution was allowed to warm to 25° C. and stirred for 18 h. The mixture was washed with saturated sodium bicarbonate and water. The organic phase was separated, dried, and concentrated to dryness. The residue was purified by flash column chromatography (silica, Hexanes/EtOAc=2:1) to afford the title compound (16) (3.50 g, 46% yield). $^1$H NMR (300 MHz, CDCl$_3$) δ 7.76 (d, J=7.5 Hz, 2H), 7.72 (d, J=7.5 Hz, 2H), 7.41 (t, J=7.5 Hz, 2H), 7.34 (t, J=7.5 Hz, 2H), 6.58 (s, 1H), 6.22 (br. s, 2H), 4.62 (d, J=6.9 Hz, 2H), 4.31 (t, J=7.2 Hz, 1H), 4.22 (dd, J=7.5, 6.9 Hz, 2H), 1.56 (s, 6H), 1.24 (t, J=7.5 Hz, 3H).

Example 17

Preparation of 2-[(2-amino-thiazol-4-yl)-carboxymethyleneaminooxy]-2-methyl-propionic acid ethyl ester (17)

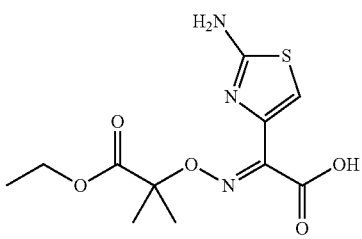 [SMILES: CCOC(=O)C(C)(C)O/N=C(/C(=O)O)c1csc(N)n1]

To a solution of 2-[(2-amino-thiazol-4-yl)-(9H-fluoren-9-ylmethoxycarbonyl)-methyleneaminooxy]-2-methyl-propionic acid ethyl ester (16) (1.84 g, 3.84 mmol, 1.0 eq) in dichloromethane (20 mL) was treated with piperidine (654 mg, 7.68 mmol, 2.0 eq). The reaction mixture was stirred at 25° C. for 3 h. The reaction mixture was concentrated to dryness. The residue was purified by prep-HPLC to give the title compound (17) (1.17 g, 73% yield) as a white solid. $^1$H NMR (300 MHz, CDCl$_3$) δ 6.78 (s, 1H), 4.16 (dd, J=7.5, 6.9 Hz, 2H), 1.57 (s, 6H), 1.24 (t, J=7.5 Hz, 3H).

Example 18

Synthesis of 2-(((Z)-(1-(2-aminothiazol-4-yl)-2-(((2S,3S)-1-((3-ethoxy-2,2-dimethyl-3-oxopropoxy)sulfonyl)-2-methyl-4-oxoazetidin-3-yl)amino)-2-oxoethylidene)amino)oxy)-2-methylpropanoic acid TFA Salt (18)

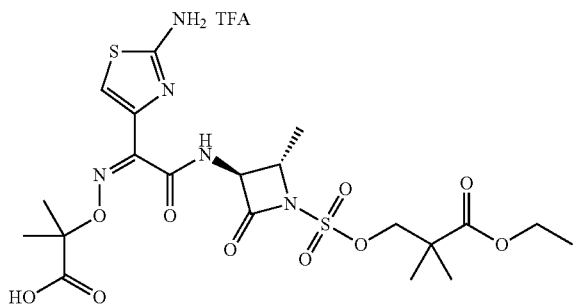 [SMILES: CCOC(=O)C(C)(C)COS(=O)(=O)N1C(=O)[C@@H](NC(=O)/C(=N\OC(C)(C)C(=O)O)c2csc(N)n2)[C@@H]1C]

Method 1.
To a solution of 3-(3-amino-2-methyl-4-oxo-azetidine-1-sulfonyloxy)-2,2-dimethyl-propionic acid ethyl ester methane sulfonic acid salt (7) (1.06 g, 3.44 mmol, 1.0 eq) and 2-[(2-amino-thiazol-4-yl)-carboxy-methyleneaminooxy]-2-methyl-propionic acid tert-butyl ester (B) (1.13 g, 3.44 mmol, 1.0 eq) in dichloromethane (140 mL) was added EDCI (988 mg, 5.16 mmol, 1.5 eq) at 0° C. for 10 min. The reaction was concentrated to dryness. The residue was purified by prep-HPLC to give the title compound (18) (783 mg, 37% yield) as a white solid. $^1$H NMR (300 MHz, CDCl$_3$) δ 9.15 (d, J=6.9 Hz, 1H), 7.35 (s, 1H), 4.57-4.41 (m, 4H), 4.16 (dd, J=7.2, 6.9 Hz, 2H), 1.72-1.68 (m, 9H), 1.46

(s, 9H), 1.28-1.24 (m, 9H). $^{13}$C NMR (75 MHz, CDCl$_3$) δ 175.0, 173.7, 170.6, 162.6, 159.6, 141.5, 132.5, 117.8, 113.9, 110.2, 85.6, 83.4, 63.6, 61.5, 59.1, 43.1, 27.9, 23.7, 23.4, 22.0, 18.0, 14.2.

Method 2.

To a solution β-lactam methane sulfonic acid salt (7) (1.74 mmol, 0.3 M in DCM) at 0° C. were added (Z)-2-(2-aminothiazol-4-yl)-2-(((1-(tert-butoxy)-2-methyl-1-oxopropan-2-yl)oxy)imino)acetic acid (17) (573 mg, 1.74 mmol, 1.0 eq) and a solution of EDCI (500 mg, 2.61 mmol, 1.5 eq) in DCM (1.5 mL). The reaction was stirred at 25° C. for 30 min to provide the tert-butoxy protected β-lactam MSA salt (18a). The reaction mixture was slowly added to a solution of TFA/DCM (15/100, 8.7 mL/58 mL) at 25° C. The reaction was stirred for 2-3 h and monitored by LCMS. When completed, the reaction was concentrated in vacuo and the residue dissolved in MeCN and purified by prep-HPLC in 10-100% MeCN/H$_2$O with 0.1% TFA (30 min, flow rate 20 mL/min) to give the final product (18) (0.77 g, 71% yield for 3 steps) as white solid. $^1$H NMR (300 MHz, chloroform-d) δ 8.91 (s, 1H), 7.83 (s, 1H), 7.04 (s, 1H), 4.51-4.46 (m, 1H), 4.40 (dd, J=27.7, 9.1 Hz, 2H), 4.14 (q, J=7.1 Hz, 2H), 1.61 (d, J=9.9 Hz, 9H), 1.31-1.19 (m, 9H). $^{13}$C NMR (75 MHz, CDCl$_3$) δ 176.7, 175.2, 170.5, 163.4, 159.7, 141.4, 131.4, 110.8, 85.2, 77.7, 77.4, 63.3, 61.7, 59.6, 42.9, 41.0, 23.6, 23.3, 21.9, 17.7, 14.1. LC-MS: 564 [M+H]$^+$ Example 19

Preparation of ethyl 3-((((2S,3S)-3-((Z)-2-(2-aminothiazol-4-yl)-2-(((1-ethoxy-2-methyl-1-oxopropan-2-yl)oxy)imino)acetamido)-2-methyl-4-oxoazetidin-1-yl)sulfonyl)oxy)-2,2-dimethylpropanoate TFA Salt (19)

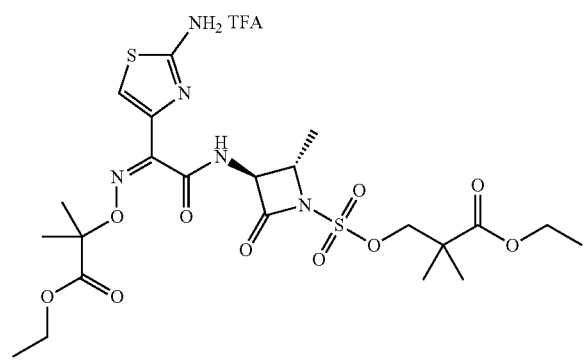 [SMILES: CCOC(=O)C(C)(C)COS(=O)(=O)N1C(=O)[C@@H](NC(=O)/C(=N\OC(C)(C)C(=O)OCC)c2csc(N)n2)[C@@H]1C]

To a solution of 3-(3-amino-2-methyl-4-oxo-azetidine-1-sulfonyloxy)-2,2-dimethyl-propionic acid ethyl ester (7) (1.19 g, 2.95 mmol, 1.0 eq) and 2-[(2-amino-thiazol-4-yl)-carboxy-methyleneaminooxy]-2-methyl-propionic acid ethyl ester (17) (1.22 g, 2.95 mmol, 1.0 eq) in dichloromethane (100 mL) was added EDCI (847 mg, 4.43 mmol, 1.5 eq) at 0° C. The reaction was stirred for 10 min and concentrated to dryness. The residue was purified by prep-HPLC to give the title compound (19) (1.20 g, 58% yield) as a white solid. $^1$H NMR (300 MHz, CDCl$_3$) δ 9.38-9.25 (br. s, 2H), 9.12 (d, J=6.9 Hz, 1H), 7.33 (s, 1H), 4.53-4.40 (m, 4H), 4.25-4.11 (m, 4H), 1.73 (s, 3H), 1.65 (d, J=6.9 Hz, 3H), 1.28-1.23 (m, 6H). $^{13}$C NMR (75 MHz, CDCl$_3$) δ 174.9, 174.4, 170.7, 162.7, 159.6, 141.7, 132.5, 117.9, 114.1, 110.2, 85.3, 63.5, 62.3, 61.5, 59.2, 42.9, 23.7, 22.0, 17.9, 14.2, 14.1. LCMS: 592 [M+1]$^+$.

Example 20

Synthesis of benzyl (Z)-2-(((2-((9H-fluoren-9-yl)methoxy)-1-(2-aminothiazol-4-yl)-2-oxoethylidene)amino)oxy)-2-methylpropanoate (20)

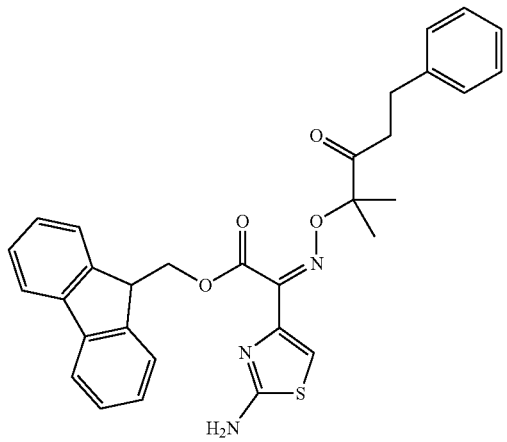 [SMILES: CC(C)(O/N=C(\C(=O)OCC1c2ccccc2-c2ccccc21)c1csc(N)n1)C(=O)CCc1ccccc1]

To a suspension of (Z)-2-(((2-((9H-fluoren-9-yl)methoxy)-1-(2-aminothiazol-4-yl)-2-oxoethylidene)amino)oxy)-2-methylpropanoic acid TFA salt (15) (2.0 g, 3.5 mmol, 1.0 eq), benzyl alcohol (2.1 mL, 35.4 mmol, 10.0 equiv.), DCM (10.5 mL) and DMAP (0.14 g, 1.1 mmol, 0.3 equiv.) was added EDCI (1.04 g, 5.3 mmol, 1.5 equiv.) in DCM (5 mL) at 0° C. The mixture was allowed to warm to 25° C. overnight. DCM was partially removed and the resulting colorless oil was purified by column chromatography on silica gel using EtOAc/hexanes (0:1 to 1:0) as eluent to give the title compound (20) with a minor impurity (0.85 g, 44% yield). $^1$H NMR (300 MHz, CDCl$_3$) δ 7.77-7.66 (m, 4H), 7.39 (t, J=6.9 Hz, 2H), 7.31-7.19 (m, 5H, overlapped with CDCl$_3$), 6.47 (s, 1H), 6.16 (br. s, 2H), 5.21 (s, 2H), 4.63 (d, J=6.9 Hz, 2H), 4.30 (t, J=7.1 Hz, 1H), 1.55 (s, 6H). $^{13}$C NMR (75 MHz, CDCl$_3$), δ 171.0, 167.5, 167.1, 140.4, 132.1, 131.8, 130.6, 129.5, 125.8, 83.7, 62.0, 61.2, 60.2, 47.2, 36.9, 34.0, 24.1, 23.8, 21.9, 20.8, 17.5.

Example 21

Synthesis of (Z)-2-(2-aminothiazol-4-yl)-2-(((1-(benzyloxy)-2-methyl-1-oxopropan-2-yl)oxy)imino)acetic acid TEA Salt (21)

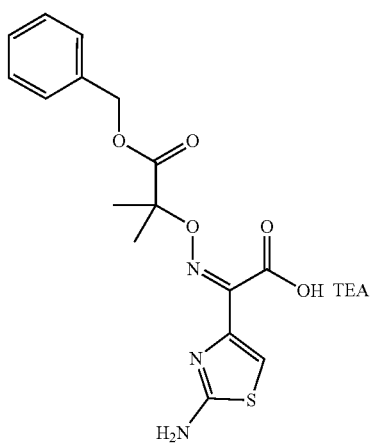 [SMILES: CC(C)(O/N=C(\C(=O)O)c1csc(N)n1)C(=O)OCc1ccccc1]

Benzyl (Z)-2-(((2-((9H-fluoren-9-yl)methoxy)-1-(2-aminothiazol-4-yl)-2-oxoethylidene)amino)oxy)-2-methylpropanoate (20) (8.44 g, 15.6 mmol, 1.0 equiv.) was dissolved in DCM (120 mL), then Et₃N (4.9 mL, 35.2 mmol, 2.3 equiv.) was added in one portion. The mixture was stirred at 40° C. for 3 h and then at 25° C. overnight. The reaction mixture was concentrated, and the residue was sonicated with Et₂O. The solid was filtered and dried in an oven at 40° C. overnight to afford the title compound (21) as an off-white powder (6.39 g, 88% yield). ¹H NMR (300 MHz, CDCl₃) δ 7.34-7.23 (m, 5H), 6.95 (br. s, 2H), 6.69 (s, 1H), 5.18 (s, 2H), 3.01 (q, J=7.0 Hz, 6H), 1.52 (s, 6H), 1.22 (t, J=7.0 Hz, 9H). ¹³C NMR (300 MHz, CDCl₃) δ 175.4, 169.5, 167.9, 154.2, 143.8, 136.0, 128.5, 128.0, 109.8, 81.6, 66.8, 45.1, 24.2, 8.6.

Example 22

Synthesis of ethyl 3-(((((2S,3S)-3-((Z)-2-(2-aminothiazol-4-yl)-2-(((1-(benzyloxy)-2-methyl-1-oxopropan-2-yl)oxy)imino)acetamido)-2-methyl-4-oxoazetidin-1-yl)sulfonyloxy)-2,2-dimethylpropanoate TFA Salt (22)

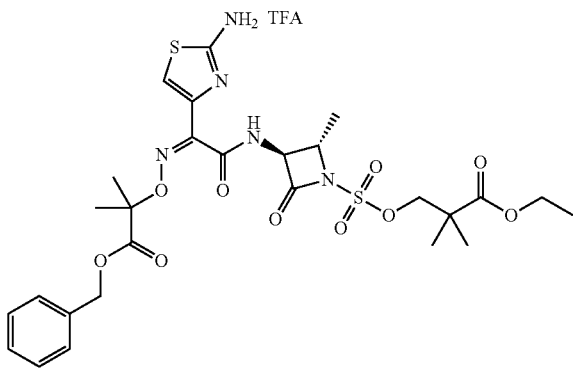 [SMILES: CCOC(=O)C(C)(C)COS(=O)(=O)N1C(=O)[C@@H](NC(=O)/C(=N\OC(C)(C)C(=O)OCc2ccccc2)c2csc(N)n2)[C@@H]1C]

To a solution of 3-(3-amino-2-methyl-4-oxo-azetidine-1-sulfonyloxy)-2,2-dimethyl-propionic acid ethyl ester (7 MSA salt) (1.49 g, 3.70 mmol, 1.0 eq) and 2-[(2-aminothiazol-4-yl)-carboxy-methyleneaminooxy]-2-methyl-propionic acid benzyl ester (21 TEA salt) (1.72 g, 3.70 mmol, 1.0 eq) in dichloromethane (150 mL) was added EDCI (1.06 g, 5.55 mmol, 1.5 eq) at 0° C. for 10 min. The reaction was concentrated to dryness. The residue was purified by prep-HPLC to give the title compound (22) (1.94 g, 68%) as a white solid. ¹H NMR (300 MHz, CDCl₃) δ 9.58-9.43 (br. s, 2H), 8.74 (d, J=7.8 Hz, 1H), 7.39-7.31 (m, 6H), 5.19 (s, 2H), 4.52-4.38 (m, 3H), 4.25-4.22 (m, 1H), 4.16 (dd, J=7.5, 6.9 Hz, 2H), 1.75 (s, 3H), 1.72 (s, 3H), 1.59 (d, J=5.7 Hz, 3H), 1.27-1.23 (m, 9H). ¹³C NMR (75 MHz, CDCl₃) δ 175.1, 173.7, 170.5, 162.7, 159.4, 141.2, 135.1, 131.9, 128.9, 128.7, 128.3, 117.7, 113.9, 110.5, 85.5, 67.8, 63.4, 61.6, 59.0, 46.4, 42.9, 23.6, 23.3, 21.9, 17.8, 14.1. LCMS: 654 [M+H]⁺.

Example 23

Synthesis of (Z)-2-methoxyethyl 2-(((2-((9H-fluoren-9-yl)methoxy)-1-(2-aminothiazol-4-yl)-2-oxoethylidene)amino)oxy)-2-methylpropanoate (23)

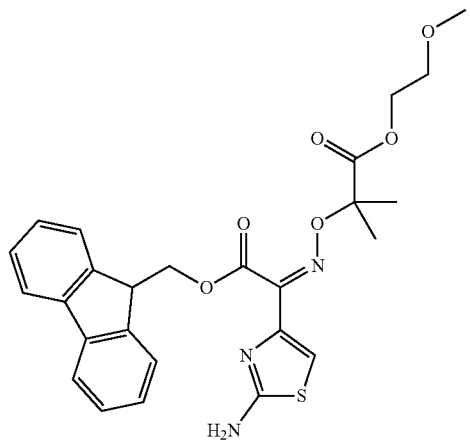 [SMILES: COCCOC(=O)C(C)(C)O/N=C(\C(=O)OCC1c2ccccc2-c2ccccc21)c1csc(N)n1]

To a solution of (Z)-2-(((2-((9H-fluoren-9-yl)methoxy)-1-(2-aminothiazol-4-yl)-2-oxoethylidene)amino)oxy)-2-methylpropanoic acid TFA salt (15) (1.0 g, 1.8 mmol, 1.0 eq.) and 2-methoxyethanol (1.04 mL, 17.7 mmol, 10.0 eq.) in DCM (5.3 mL) was added EDCI (0.52 g, 2.7 mmol, 1.5 eq.) and DMAP (0.11 g, 0.9 mmol, 0.5 eq.) at a temperature of 0° C. After stirring at 0° C. for 10 min, the reaction mixture was warmed to 25° C. and stirred overnight. The reaction mixture was diluted with DCM and washed with water and brine, and then dried (Na₂SO₄), filtered, and concentrated under vacuum. The residue was purified by column chromatography on silica get using EtOAc/hexanes (0:1 to 1:0) as eluent (2 columns) to give the product (23) (370 mg). ¹H NMR (300 MHz, CDCl₃) δ 7.77 (d, J=7.2 Hz, 2H), 7.71 (d, J=6.9 Hz, 2H), 7.41 (t, J=7.1 Hz, 2H), 7.32 (t, J=7.4 Hz, 2H), 6.55 (s, 2H), 6.47 (s, 1H), 4.65 (d, J=7.2 Hz, 2H), 4.32-4.30 (m, 3H), 3.58 (t, J=8.7 Hz, 2H), 3.28 (s, 3H), 1.54 (s, 6H). ¹³C NMR (75 MHz, CDCl₃) δ 174.4, 169.9, 162.8, 146.9, 143.4, 141.5, 141.3, 128.0, 127.2, 125.4, 120.0, 110.8, 83.0, 70.3, 67.4, 64.4, 58.9, 46.7, 23.8. LCMS: 510.2 [M+H]⁺.

Example 24

Synthesis of (Z)-10-(2-aminothiazol-4-yl)-7,7-dimethyl-6-oxo-2,5,8-trioxa-9-azaundec-9-en-11-oic acid TEA Salt (24)

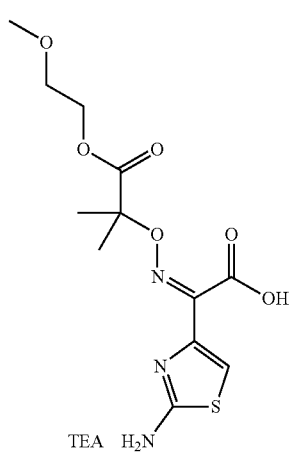 [SMILES: COCCOC(=O)C(C)(C)O/N=C(\C(=O)O)c1csc(N)n1]

(Z)-2-Methoxyethyl 2-(((2-((9H-fluoren-9-yl)methoxy)-1-(2-aminothiazol-4-yl)-2-oxoethylidene)amino)oxy)-2-methylpropanoate (23) (9.0 g, 17.7 mmol, 1.0 eq.) was dissolved in DCM (128 mL) and Et₃N (4.9 mL, 35.3 mmol, 2.0 eq.). The mixture was stirred at 40° C. for 3 h and then stirred at 25° C. overnight. The reaction mixture was concentrated under vacuum, the residue sonicated with Et₂O, and filtered to afford the title compound (24) as the TEA salt (6.2 g, 81% yield). ¹H NMR (300 MHz, d₆-DMSO) δ 7.15 (br. s, 2H), 6.64 (s, 1H), 4.16 (t, J=4.8 Hz, 2H), 3.51 (t, J=4.7 Hz, 2H), 3.23 (s, 3H), 3.03 (q, J=7.2 Hz, 6H), 1.38 (s, 6H), 1.17 (t, J=6.9 Hz, 9H). ¹³C NMR (75 MHz, d₆-DMSO) δ 173.8, 168.5, 165.5, 144.1, 109.2, 81.1, 70.1, 64.0, 58.6, 45.5, 35.0, 24.4, 8.9. LCMS: 332.1 [M+H]⁺.

Example 25

Synthesis of ethyl 3-(((((2S,3S)-3-((Z)-10-(2-aminothiazol-4-yl)-7,7-dimethyl-6-oxo-2,5,8-trioxa-9-azaundec-9-en-11-amido)-2-methyl-4-oxoazetidin-1-yl)sulfonyl)oxy)-2,2-dimethylpropanoate (25)

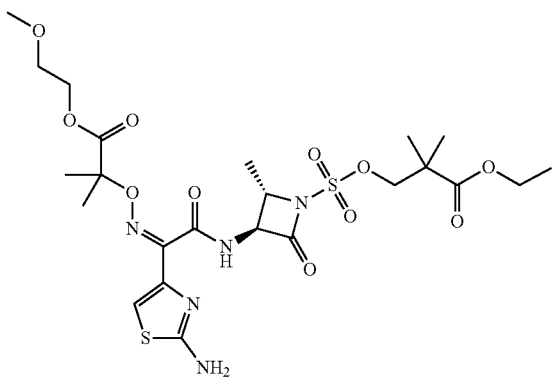 [SMILES: CCOC(=O)C(C)(C)COS(=O)(=O)N1C(=O)[C@@H](NC(=O)/C(=N\OC(C)(C)C(=O)OCCOC)c2csc(N)n2)[C@@H]1C]

To a solution of 3-(3-amino-2-methyl-4-oxo-azetidine-1-sulfonyloxy)-2,2-dimethyl-propionic acid ethyl ester (7 MSA Salt) (1.49 g, 3.70 mmol, 1.0 eq) and 2-[(2-aminothiazol-4-yl)-carboxy-methyleneaminooxy]-2-methyl-propionic acid 2-methoxy-ethyl ester (25 TEA salt) (1.72 g, 3.70 mmol, 1.0 eq) in dichloromethane (150 mL) was added EDCI (1.06 g, 5.55 mmol, 1.5 eq) at 0° C. The reaction mixture was stirred for 10 min and then concentrated to dryness. The residue was purified by prep-HPLC to give the title compound (25) (1.45 g, 53% yield) as a white solid. ¹H NMR (300 MHz, CDCl₃) δ 9.55-9.39 (br. s, 2H), 8.75 (d, J=6.9 Hz, 1H), 7.19 (s, 1H), 4.52-4.38 (m, 4H), 4.32-4.28 (m, 2H), 4.16 (dd, J=7.2, 6.9 Hz, 2H), 3.60 (t, J=4.5 Hz, 2H), 3.35 (s, 3H), 1.72 (s, 3H), 1.68 (s, 3H), 1.63 (d, J=5.7 Hz, 3H), 1.27-1.23 (m, 9H). ¹³C NMR (75 MHz, CDCl₃) δ 174.9, 173.8, 170.7, 162.8, 159.7, 141.7, 132.0, 117.9, 114.1, 110.3, 85.2, 70.2, 64.5, 63.4, 61.5, 59.1, 58.8, 42.8, 23.6, 23.3, 22.0, 17.8, 14.1. LCMS: 622 [M+H]⁺

Example 26

Synthesis of hexyl (Z)-2-(((2-((9H-fluoren-9-yl)methoxy)-1-(2-aminothiazol-4-yl)-2-oxoethylidene)amino)oxy)-2-methylpropanoate (26)

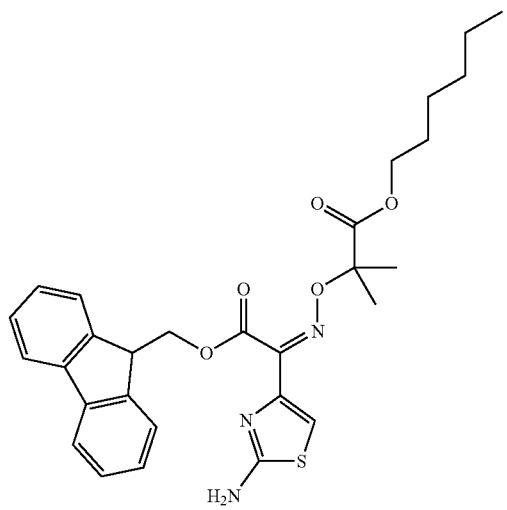 [SMILES: CCCCCCOC(=O)C(C)(C)O/N=C(\C(=O)OCC1c2ccccc2-c2ccccc21)c1csc(N)n1]

(Z)-2-(((2-((9H-Fluoren-9-yl)methoxy)-1-(2-aminothiazol-4-yl)-2-oxoethylidene)amino)oxy)-2-methylpropanoic acid TFA salt (15) (15.0 g, 26.5 mmol, 1.0 eq), 1-hexanol (15.5 mL, 265.2 mmol, 10.0 eq), and DMAP (1.04 g, 8.5 mmol, 0.3 eq) were suspended in DCM (225 mL) and cooled to a temperature from −15° C. to −10° C. for 10 min. EDCI (15.6 g, 79.6 mmol, 3.0 eq) was added to the reaction mixture. The reaction mixture was stirred at −15° C. to −10° C. for 3 h. The reaction was concentrated to a small volume and adsorbed onto silica gel (30 g). The crude product was purified by column chromatography on silica gel (330 g cartridge) using EtOAc/hexanes (0:1 to 1:0) as eluent to give the title compound (26) as a solid (7.68 g, 54% yield). ¹H NMR (300 MHz, CDCl₃) δ 7.79 (d, J=7.5 Hz, 2H), 7.72 (d, J=7.5 Hz, 2H), 7.42 (t, J=7.8 Hz, 2H), 7.32 (t, J=7.8 Hz, 2H), 7.17 (br. s, 2H), 6.38 (s, 1H) 4.67 (d, J=7.2 Hz, 2H), 4.32 (t, J=6.9 Hz, 1H), 4.19 (t, J=6.3 Hz, 2H), 1.55-1.67 (m, 3H), 1.52 (s, 6H), 1.26-1.33 (m, 2H), 1.15-1.98 (m, 4H), 0.76-0.81 (m, 3H). LCMS: 536 [M+H]⁺.

Example 27

Synthesis of (Z)-2-(2-aminothiazol-4-yl)-2-(((1-(hexyloxy)-2-methyl-1-oxopropan-2-yl)oxy)imino)acetate TEA Salt (27)

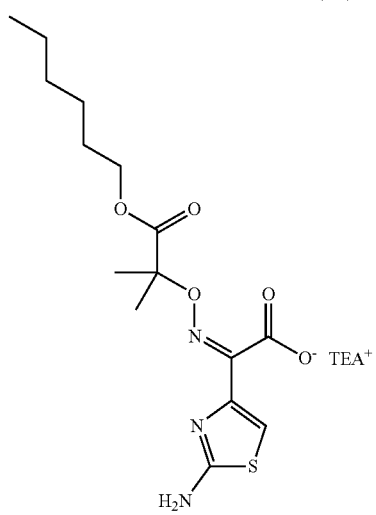

Hexyl (Z)-2-(((2-((9H-fluoren-9-yl)methoxy)-1-(2-aminothiazol-4-yl)-2-oxoethylidene)amino)oxy)-2-methylpropanoate (26) (8.68 g, 16.2 mmol, 1.0 eq) was dissolved in DCM (125 mL) and Et₃N (4.75 mL, 34.1 mmol, 2.0 eq). The mixture was stirred at 40° C. for 3 h. The reaction mixture was concentrated under vacuum and the residue was sonicated with Et₂O (200 mL). The solid was collected by filtration and then rinsed with fresh Et₂O (2×50 mL) to afford the product (27) (6.54 g, 88% yield) as a solid. ¹H NMR (300 MHz, d₆-DMSO) δ 8.0 (br. s, 2H), 6.67 (s, 1H), 4.1 (t, J=7.2 Hz, 2H), 3.07 (q, J=7.2 Hz, 6H), 1.58-1.62 (m, 4H), 1.49 (s, 6H), 1.2-1.4 (m, 14H), 0.85 (t, J=6.6 Hz, 3H). ¹³C NMR (75 MHz, d₆-DMSO) δ 175.0, 169.9, 166.8, 150.8, 141.7, 108.8, 82.0, 65.3, 45.4, 31.4, 28.5, 25.5, 24.1, 22.5, 14.0, 8.5. LCMS: 358 [M+H]⁺.

Example 28

Synthesis of ethyl 3-((((2S,3S)-3-((Z)-2-(2-aminothiazol-4-yl)-2-(((1-(hexyloxy)-2-methyl-1-oxopropan-2-yl)oxy)imino)acetamido)-2-methyl-4-oxoazetidin-1-yl)sulfonyl)oxy)-2,2-dimethylpropanoate (28)

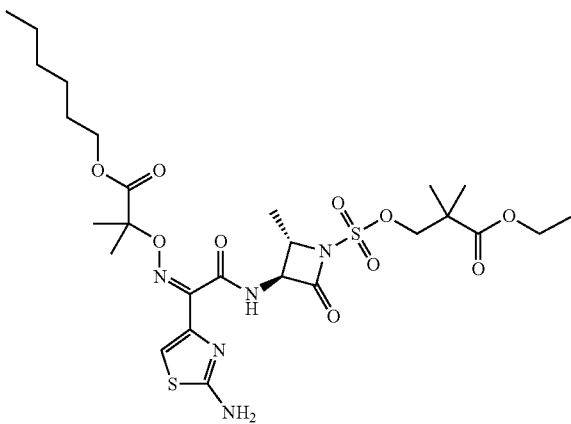 [SMILES: CCCCCCOC(=O)C(C)(C)O/N=C(\C(=O)N[C@@H]1C(=O)N(S(=O)(=O)OCC(C)(C)C(=O)OCC)[C@H]1C)c1csc(N)n1]

To a solution of 3-(3-amino-2-methyl-4-oxo-azetidine-1-sulfonyloxy)-2,2-dimethyl-propionic acid ethyl ester MSA salt (7) (1.06 g, 2.50 mmol, 1.0 eq) and 2-[(2-amino-thiazol-4-yl)-carboxy-methyleneaminooxy]-2-methyl-propionic acid hexyl ester TEA salt (27) (1.15 g, 2.50 mmol, 1.0 eq) in DCM (100 mL) was added EDCI (718 mg, 3.75 mmol, 1.5 eq) at 0° C. The reaction mixture was stirred for 10 min and then concentrated to dryness. The residue was purified by prep-HPLC to give the title compound (28) (1.25 g, 66% yield) as a white solid. ¹H NMR (300 MHz, CDCl₃) δ 9.58-9.49 (br. s, 2H), 8.93 (d, J=6.9 Hz, 1H), 7.18 (s, 1H), 4.50-4.38 (m, 4H), 4.17-4.11 (q, 4H), 1.69-1.62 (m, 13H), 1.29-1.22 (m, 13H), 0.88 (t, J=7.5 Hz, 3H). ¹³C NMR (75 MHz, CDCl₃) δ 174.9, 174.4, 170.7, 162.6, 159.6, 141.7, 132.3, 117.9, 114.1, 110.3, 85.3, 66.3, 63.6, 61.5, 59.1, 42.9, 31.4, 28.5, 25.5, 23.7, 23.3, 22.6, 22.0, 21.0, 17.9, 14.1. LCMS: 648 [M+H]⁺

Example 29

Synthesis of (5-methyl-2-oxo-1,3-dioxol-4-yl)methyl (Z)-2-(((2-((9H-fluoren-9-yl)methoxy)-1-(2-aminothiazol-4-yl)-2-oxoethylidene)amino)oxy)-2-methylpropanoate (29)

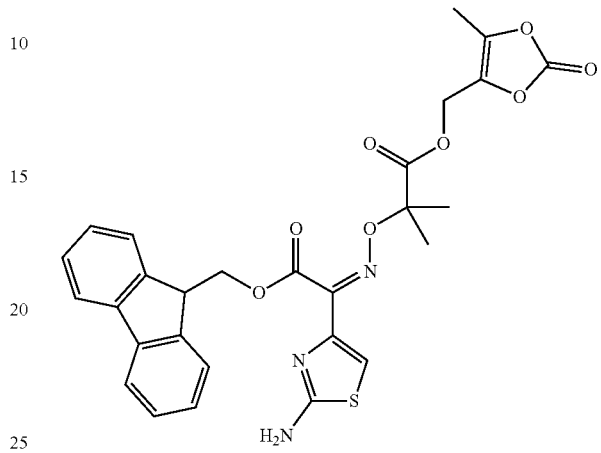

To a suspension of (Z)-2-(((2-((9H-fluoren-9-yl)methoxy)-1-(2-aminothiazol-4-yl)-2-oxoethylidene)amino)oxy)-2-methylpropanoic acid MSA salt (15) (11.1 g, 24.6 mmol, 1.0 eq) and in dry DCM (114 mL), 4-(hydroxymethyl)-5-methyl-1,3-dioxol-2-one (14.5 mL, 245.8 mmol, 10.0 eq) and DMAP (17 mg) were added at 0° C. The reaction mixture was allowed to warm to 25° C. and stirred overnight. The reaction mixture was concentrated under vacuum and the residue was diluted with EtOAc and washed with H₂O and brine, and then dried (Na₂SO₄), filtered, and concentrated under vacuum. The resulting residue was dissolved in DCM and dry-loaded on to silica gel and purified by column chromatography using EtOAc/hexanes (0:1 to 3:2) as eluent to give the impure product (29) that was used directly in the next step.

Example 30

Synthesis of (Z)-2-(2-aminothiazol-4-yl)-2-(((2-methyl-1-((5-methyl-2-oxo-1,3-dioxol-4-yl)methoxy)-1-oxopropan-2-yl)oxy)imino)acetic acid (30)

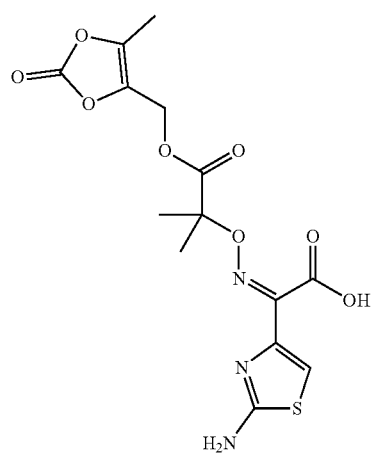 [SMILES: Cc1oc(=O)oc1COC(=O)C(C)(C)O/N=C(\C(=O)O)c1csc(N)n1]

(5-Methyl-2-oxo-1,3-dioxol-4-yl)methyl (Z)-2-(((2-((9H-fluoren-9-yl)methoxy)-1-(2-aminothiazol-4-yl)-2-oxoethylidene)amino)oxy)-2-methylpropanoate (29) (4.9 g, 8.7 mmol, 1.0 eq) was dissolved in DCM (70 mL) and Et₃N (2.7 mL, 19.2 mmol, 2.2 eq). The mixture was stirred at 40° C. for 2 h and then stirred at 25° C. for 2 h. Completion of the reaction was monitored using LCMS. The reaction mixture was concentrated under vacuum and the residue was stirred with Et₂O overnight and then filtered to afford the title compound (30) (impure) as a TEA salt (3.2 g). The yellow solid was dissolved in ACN/H₂O (2:1) and purified by reverse-phase HPLC to give the product (30) as a solid. ¹H-NMR (300 MHz, d-DMSO), δ 7.26 (br. s, 2H), 6.79 (s, 1H), 5.02 (s, 2H), 2.12 (s, 3H), 1.44 (s, 6H). LCMS: 386.1 [M+H]⁺.

Finally, it should be noted that there are alternative ways of implementing the embodiments disclosed herein. Accordingly, the present embodiments are to be considered as illustrative and not restrictive, and the claims are not to be limited to the details given herein but may be modified within the scope and equivalents thereof.

What is claimed is:

1. A method of synthesizing an aztreonam derivative of Formula (1a):

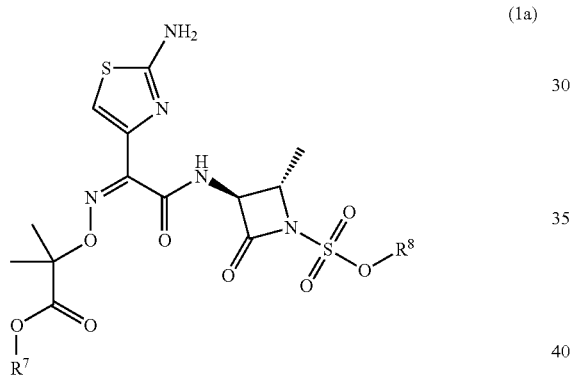

(1a)

or a pharmaceutically acceptable salt thereof, wherein,
R⁷ is selected from C₁₋₈ alkyl, C₁₋₈ heteroalkyl, C₅₋₈ cycloalkyl, C₅₋₈ heterocycloalkyl, C₅₋₁₀ cycloalkylalkyl, C₅₋₁₀ heterocycloalkylalkyl, C₆₋₈ aryl, C₅₋₈ heteroaryl, C₇₋₁₀ arylalkyl, C₅₋₁₀ heteroarylalkyl, substituted C₁₋₈ alkyl, substituted C₁₋₈ heteroalkyl, substituted C₅₋₈ cycloalkyl, substituted C₅₋₈ heterocycloalkyl, substituted C₅₋₁₀ cycloalkylalkyl, substituted C₅₋₁₀ heterocycloalkylalkyl, substituted C₆₋₈ aryl, substituted C₅₋₈ heteroaryl, substituted C₇₋₁₀ arylalkyl, and substituted C₅₋₁₀ heteroarylalkyl; and
R⁸ is selected from C₁₋₂₀ alkyl, C₁₋₂₀ alkanecycloalkyl, C₁₋₂₀ alkanearyl, C₁₋₂₀ heteroalkyl, C₁₋₂₀ heteroalkanecycloalkyl, C₁₋₂₀ heteroalkanearyl, substituted C₁₋₂₀ alkyl, substituted C₁₋₂₀ alkanecycloalkyl, substituted C₁₋₂₀ alkanearyl, substituted C₁₋₂₀ heteroalkyl, substituted C₁₋₂₀ heteroalkanecycloalkyl, and substituted C₁₋₂₀ heteroalkanearyl;
comprising (a) reacting an organyl 3-amino-2-methyl-4-oxoazetidine-1-sulfonate salt with a 2-[(2-amino-thiazol-4-yl)-carboxy-methyleneaminooxy]-2-methyl-propionic acid ester in the presence of a carboxyl activating agent to provide the corresponding aztreonam sulfonyloxy organyl ester salt having the structure of Formula (1a), wherein, the organyl 3-amino-2-methyl-4-oxoazetidine-1-sulfonate salt has the structure of Formula (5a):

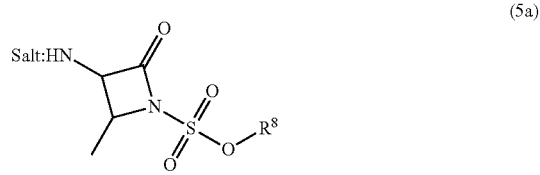

(5a)

wherein,
R⁸ is selected from C₁₋₂₀ alkyl, C₁₋₂₀ alkanecycloalkyl, C₁₋₂₀ alkanearyl, C₁₋₂₀ heteroalkyl, C₁₋₂₀ heteroalkanecycloalkyl, C₁₋₂₀ heteroalkanearyl, substituted C₁₋₂₀ alkyl, substituted C₁₋₂₀ alkanecycloalkyl, substituted C₁₋₂₀ alkanearyl, substituted C₁₋₂₀ heteroalkyl, substituted C₁₋₂₀ heteroalkanecycloalkyl, and substituted C₁₋₂₀ heteroalkanearyl; and the 2-[(2-amino-thiazol-4-yl)-carboxy-methyleneaminooxy]-2-methyl-propionic acid ester has the structure of Formula (7):

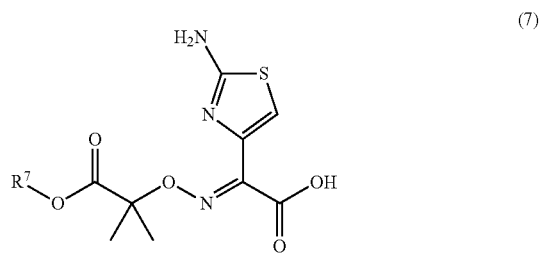

(7)

wherein,
R⁷ is selected from C₁₋₈ alkyl, C₁₋₈ heteroalkyl, C₅₋₈ cycloalkyl, C₅₋₈ heterocycloalkyl, C₅₋₁₀ cycloalkylalkyl, C₅₋₁₀ heterocycloalkylalkyl, C₆₋₈ aryl, C₅₋₈ heteroaryl, C₇₋₁₀ arylalkyl, C₅₋₁₀ heteroarylalkyl, substituted C₁₋₈ alkyl, substituted C₁₋₈ heteroalkyl, substituted C₅₋₈ cycloalkyl, substituted C₅₋₈ heterocycloalkyl, substituted C₅₋₁₀ cycloalkylalkyl, substituted C₅₋₁₀ heterocycloalkylalkyl, substituted C₆₋₈ aryl, substituted C₅₋₈ heteroaryl, substituted C₇₋₁₀ arylalkyl, and substituted C₅₋₁₀ heteroarylalkyl.

2. The method of claim 1, wherein,
the carboxyl activating agent is selected from N-(3-dimethylaminopropyl)-N'-ethylcarbodiimide hydrochloride (EDCI), 1-[bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), N,N,N',N'-tetramethyl-O-(benzotriazol-1-yl) uronium tetrafluoroborate (TBTU), 1-propanephosphonic anhydride solution, 2,4,6-tripropyl-1,3,5,2,4,6-trioxatriphosphorinane-2,4,6-trioxide (T3P), or a combination of any of the foregoing; and
the pharmaceutically acceptable salt comprises the methanesulfonic acid salt, the triethylamine salt, the trifluoroacetic acid salt, or a combination of any of the foregoing.

3. The method of claim 1, wherein $R^8$ is a neopentyl group having the structure of Formula (2):

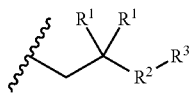
(2)

wherein,
- each $R^1$ is independently $C_{1-6}$ alkyl, or each $R^1$ and the geminal carbon atom to which each $R^1$ is bonded forms a $C_{3-6}$ cycloalkyl ring, a $C_{3-6}$ heterocycloalkyl ring, a substituted $C_{3-6}$ cycloalkyl ring, or a substituted $C_{3-6}$ heterocycloalkyl ring;
- $R^2$ is selected from a single bond, $C_{1-6}$ alkanediyl, $C_{1-6}$ heteroalkanediyl, $C_{5-6}$ cycloalkanediyl, $C_{5-6}$ heterocycloalkanediyl, $C_6$ arenediyl, $C_{5-6}$ heteroarenediyl, substituted $C_{1-6}$ alkanediyl, substituted $C_{1-6}$ heteroalkanediyl, substituted $C_{5-6}$ cycloalkanediyl, substituted $C_{5-6}$ heterocycloalkanediyl, substituted $C_6$ arenediyl, and substituted $C_{5-6}$ heteroarenediyl; and
- $R^3$ is selected from $C_{1-6}$ alkyl, —O—C(O)—$R^4$, —S—C(O)—$R^4$, —NH—C(O)—$R^4$, —O—C(O)—O—$R^4$, —S—C(O)—O—$R^4$, —NH—C(O)—O—$R^4$, —C(O)—O—$R^4$, —C(O)—S—$R^4$, —C(O)—NH—$R^4$, —O—C(O)—S—$R^4$, —O—C(O)—NH—$R^4$, —S—S—$R^4$, —S—$R^4$, —NH—$R^4$, —CH(—NH$_2$)(—$R^4$), $C_{5-6}$ heterocycloalkyl, $C_{5-6}$ heteroaryl, substituted $C_{5-6}$ cycloalkyl, substituted $C_{5-6}$ heterocycloalkyl, substituted $C_{5-6}$ aryl, and substituted $C_{5-6}$ heteroaryl, wherein,
  - $R^4$ is selected from hydrogen, $C_{1-8}$ alkyl, $C_{1-8}$ heteroalkyl, $C_{5-8}$ cycloalkyl, $C_{5-8}$ heterocycloalkyl, $C_{5-10}$ cycloalkylalkyl, $C_{5-10}$ heterocycloalkylalkyl, $C_{6-8}$ aryl, $C_{5-8}$ heteroaryl, $C_{7-10}$ arylalkyl, $C_{5-10}$ heteroarylalkyl, substituted $C_{1-8}$ alkyl, substituted $C_{1-8}$ heteroalkyl, substituted $C_{5-8}$ cycloalkyl, substituted $C_{5-8}$ heterocycloalkyl, substituted $C_{5-10}$ cycloalkylalkyl, substituted $C_{5-10}$ heterocycloalkylalkyl, substituted $C_{6-8}$ aryl, substituted $C_{5-8}$ heteroaryl, substituted $C_{7-10}$ arylalkyl, and substituted $C_{5-10}$ heteroarylalkyl.

4. The method of claim 1, wherein reacting comprises reacting at a temperature from −10° C. to 10° C.

5. A method of synthesizing an aztreonam derivative of Formula (1a), comprising:

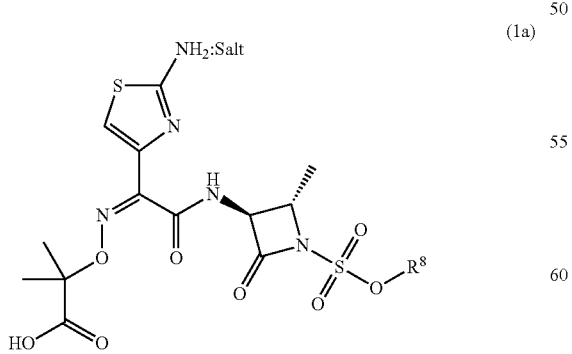
(1a)

or a pharmaceutically acceptable salt thereof, wherein, $R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; and (a) reacting an organyl 3-amino-2-methyl-4-oxoazetidine-1-sulfonate salt with a 2-[(2-amino-thiazol-4-yl)-carboxy-methyleneaminooxy]-2-methyl-propionic acid tert-butyl ester in the presence of a carboxyl coupling agent to provide the corresponding tert-butoxy protected salt; and (b) treating the tert-butoxy protected salt with an acid to provide the corresponding aztreonam sulfonyloxy organyl ester salt, wherein,
the organyl 3-amino-2-methyl-4-oxoazetidine-1-sulfonate salt has the structure of Formula (5a):

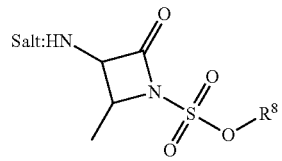
(5a)

wherein,
$R^8$ is selected from $C_{1-20}$ alkyl, $C_{1-20}$ alkanecycloalkyl, $C_{1-20}$ alkanearyl, $C_{1-20}$ heteroalkyl, $C_{1-20}$ heteroalkanecycloalkyl, $C_{1-20}$ heteroalkanearyl, substituted $C_{1-20}$ alkyl, substituted $C_{1-20}$ alkanecycloalkyl, substituted $C_{1-20}$ alkanearyl, substituted $C_{1-20}$ heteroalkyl, substituted $C_{1-20}$ heteroalkanecycloalkyl, and substituted $C_{1-20}$ heteroalkanearyl; and the 2-[(2-amino-thiazol-4-yl)-carboxy-methyleneaminooxy]-2-methyl-propionic acid tert-butyl ester (7a) has the structure of Formula (7a):

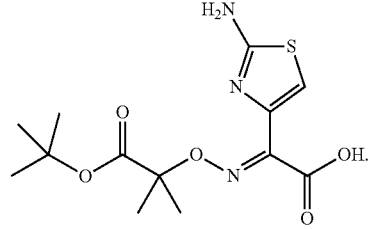
(7a)

6. The method of claim 5, wherein,
the carboxyl activating agent is selected from N-(3-dimethylaminopropyl)-N'-ethylcarbodiimide hydrochloride (EDCI), 1-[bis(dimethylamino)methylene]-1H-1,2,3-triazolo[4,5-b]pyridinium 3-oxide hexafluorophosphate (HATU), 2-(1H-benzotriazol-1-yl)-1,1,3,3-tetramethyluronium hexafluorophosphate (HBTU), N,N,N',N'-tetramethyl-O-(benzotriazol-1-yl)uronium tetrafluoroborate (TBTU), 1-propanephosphonic anhydride solution, 2,4,6-tripropyl-1,3,5,2,4,6-trioxatriphosphorinane-2,4,6-trioxide (T3P), or a combination of any of the foregoing; and
the pharmaceutically acceptable salt comprises the methanesulfonic acid salt, the triethylamine salt, the trifluoroacetic acid salt, or a combination of any of the foregoing.

* * * * *